US007939721B2

(12) United States Patent
Arnevik et al.

(10) Patent No.: US 7,939,721 B2
(45) Date of Patent: *May 10, 2011

(54) CROPPING SYSTEMS FOR MANAGING WEEDS

(75) Inventors: Cindy L. Arnevik, Troy, MO (US); Ronald J. Brinker, Ellisville, MO (US); Greg Elmore, Ellisville, MO (US); James C. Graham, Creve Coecer, MO (US); Robert D. Sammons, New Melle, MO (US); Michelle Starke, O'Fallon, MO (US); Richard D. Voth, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 766 days.

This patent is subject to a terminal disclaimer.

(21) Appl. No.: 11/758,660

(22) Filed: Jun. 5, 2007

(65) Prior Publication Data
US 2008/0305952 A1 Dec. 11, 2008

Related U.S. Application Data

(60) Provisional application No. 60/862,907, filed on Oct. 25, 2006.

(51) Int. Cl.
C12N 15/82 (2006.01)
(52) U.S. Cl. ....................................................... 800/300
(58) Field of Classification Search .................. None
See application file for complete search history.

(56) References Cited

U.S. PATENT DOCUMENTS

| 4,816,403 | A | 3/1989 | Roy | 435/253.3 |
|---|---|---|---|---|
| 5,094,945 | A | 3/1992 | Comai | 435/172.3 |
| 5,463,175 | A | 10/1995 | Barry et al. | 800/205 |
| 5,627,061 | A | 5/1997 | Barry et al. | 435/172.3 |
| 5,656,422 | A | 8/1997 | Crawford et al. | 435/4 |
| 5,670,454 | A | 9/1997 | Grossmann et al. | 504/244 |
| 6,040,497 | A | 3/2000 | Spencer et al. | 800/288 |
| 6,376,754 | B1 * | 4/2002 | Schillinger et al. | 800/312 |
| 6,586,367 | B2 | 7/2003 | Lee et al. | 504/127 |
| 7,022,896 | B1 | 4/2006 | Weeks et al. | 800/300 |
| RE39,247 | E | 8/2006 | Barry et al. | 800/300 |
| 7,105,724 | B2 | 9/2006 | Weeks et al. | 800/300 |
| 7,405,347 | B2 | 7/2008 | Hammer et al. | 800/300 |
| 2003/0041357 | A1 * | 2/2003 | Jepson et al. | 800/300 |
| 2003/0083480 | A1 | 5/2003 | Castle et al. | 800/300 |
| 2003/0115626 | A1 | 6/2003 | Weeks et al. | 800/300 |
| 2003/0135879 | A1 | 7/2003 | Weeks et al. | 800/278 |
| 2004/0082770 | A1 * | 4/2004 | Castle et al. | 536/23.2 |
| 2008/0015110 | A1 | 1/2008 | Clemente et al. | 800/300 |
| 2008/0119361 | A1 | 5/2008 | Feng et al. | 504/105 |
| 2008/0120739 | A1 | 5/2008 | Wan et al. | 800/300 |
| 2009/0029861 | A1 | 1/2009 | Feng et al. | 800/300 |
| 2009/0081760 | A1 | 3/2009 | D'Ordine et al. | 435/189 |
| 2009/0105077 | A1 | 4/2009 | Bhatti et al. | 504/206 |

FOREIGN PATENT DOCUMENTS

| CA | 2165036 | 6/1996 |
|---|---|---|
| WO | WO 97/41228 | 11/1997 |
| WO | WO 98/45424 | 10/1998 |
| WO | WO 02/068607 | 9/2002 |
| WO | WO 03/034813 | 5/2003 |
| WO | WO 2004/009761 | 1/2004 |
| WO | WO 2004/074443 | 9/2004 |
| WO | WO 2005/003362 | 1/2005 |
| WO | WO 2005/107437 | 11/2005 |
| WO | WO 2005/107437 A2 * | 11/2005 |
| WO | WO 2007/143690 | 12/2007 |
| WO | WO 2007/146706 | 12/2007 |
| WO | WO 2008/048964 | 4/2008 |
| WO | WO 2008/051633 | 5/2008 |
| WO | WO 2008/105890 | 9/2008 |

OTHER PUBLICATIONS

U.S. Appl. No. 60/811,276, filed Jun. 6, 2006, Feng et al.
Comai et al., "Expression in plants of a mutant aroA gene from *Salmonella typhimurium* confers tolerance to glyphosate," *Nature*, 317:741-744, 1985.
DeBlock et al., "Engineering herbicide resistance in plants by expression of a detoxifying enzyme," *The EMBO J.*, 6(9):2513-2518, 1987.
Herman et al., "A three-component dicamba 0-demethylase from *Pseudomonas maltophilia*, strain DI-6," *The J. of Biological Chemistry*, 280(26):24759-24767, 2005.
Padgette et al., "Development, identification and characterization of a glyphosate-tolerant soybean line," *Crop Sci.*, 35:1451-1461, 1995.
Stalker et al., "Herbicide resistance in transgenic plants expressing a bacterial detoxification gene," *Science*, 242:419-423, 1988.
Streber et al., "Transgenic tobacco plants expressing a bacterial detoxifying enzyme are resistant to 2, 4-D," *Bio/Technology*, 7:811-816, 1989.
Wang et al., "A three-component enzyme system catalyzes the O demethylation of the herbicide dicamba in *Pseudomonas maltophilia* DI-6," *Appl.Enviro. Microbiol.*, 63(4):1623-1626, 1997.
Wang, Characterization of cellular and enzymatic degradation of dicamba by *Pseudomonas maltophilia*, strain DI-6, Ph.D. Thesis, University of Nebraska-Lincoln, 1996.
Khalil et al., "Plasmid-mediated catabolism of dicamba by *Pseudomonsas* species strain PXM," *Microbios*, 102:183-191, 2000.
Spencer et al., "Segregation of transgenes in maize," *Plant Molecular Biology*, 18:201-210, 1992.
Weeks et al., "Characterization of a bacterial system capable of degrading dicamba and evaluation of its potential in the development of herbicide-tolerant crops," *J. of Cellular Biochemistry*, Supplement 18A:91, 1994.

(Continued)

Primary Examiner — David H Kruse
(74) Attorney, Agent, or Firm — SNR Denton US LLP; Pamela J. Sisson, Esq.

(57) ABSTRACT

The invention provides cropping systems for managing weeds in crop environments. The cropping systems comprise, in one embodiment, transgenic plants that display tolerance to an auxin-like herbicide such as dicamba. Method for minimizing the development of herbicide resistant weeds are also provided.

42 Claims, No Drawings

OTHER PUBLICATIONS

"Banvel Herbicide," In: Crop Protection Reference, 11th Edition, pp. 1803-1821, 1995.

U.S. Appl. No. 12/440,173, filed Mar. 5, 2009, Bhatti et al.

U.S. Appl. No. 12/875,747, filed Sep. 3, 2010, Weeks et al.

Al-Khatib et al., "Foliar absorption and translocation of dicamba from aqueous solution and dicamba-treated soil deposits," *Weed Technology*, 6:57-61, 1992.

Baker, "Response of cotton (*Gossypium hirsutum*) to preplant-applied hormone-type herbicides," *Weed Technology*, 7:150-153, 1993.

Batie et al., "Phthalate dioxygenase reductase and related flavin-iron-sulfur containing electron transferases," In: Chemistry and Biochemistry of Flavoproteins, Muller (Ed.), CRC Press, Boca Raton, FL, pp. 543-556, 1992.

Batie et al., "Purification and characterization of phthalate oxygenase and phthalate oxygenase reductase from *Pseudomonas cepacia*," *J. of Bio. Chem.*, 262(4):1510-1518, 1987.

Bernhardt et al., "A 4-methoxybenzoate O-demethylase from *Pseudomonas putida*. A new type of monoxygenase system," *Eur. J. Biochem.*, 57(1):241-256, 1975.

Butler et al., "Structure-function analysis of the bacterial aromatic ring-hydroxylating dioxygenases," *Advances in Microbial Physiology*, 38:47-85, 1997.

Dehmel et al., "Cloning, nucleotide sequence and expression of the gene encoding a novel dioxygenase involved in metabolism of carboxydiphenyl ethers in *Pseudomonas pseudoalcaligenes* POB310," *Arch. Microbiol.*, 163:35-41, 1995.

Fogarty et al., "Microbiological degradation of the herbicide dicamba," *J. of Industrial Microbiology*, 14:365-370, 1995.

Fukumori et al., "Purification and characterization of 2,-dichlorophenoxyacetate/α-ketoglutarate dioxygenase," *J. Biol. Chem.*, 268:24311-24317, 1993.

Gibson et al., "Aromatic hydrocarbon dioxygenases in environmental biotechnology," *Current Opinion in Biotechnology*, 11:236-243, 2000.

Gurbiel et al., "Active site structure of Rieske-type prteins: electron nuclear double resonance studies of isotopically labeled phthalate dioxygenase from *Pseudomonas cepacia* and Rieske protein from *Rhodobacter capsulatus* and molecular modeling studies of a Rieske center," *Biochemistry*, 35(24):7834-7845, 1996 (Abstract).

Krueger et al., "Use of dicamba-degrading microorganisms to protect dicamba susceptible plant species," *J. of Agri. and Food Chem.*, 39(5):1000-1003, 1991.

Magnusson et al., "Tolerance of soybean (*Glycine max*) and sunflower (*Helianthus annuus*) to fall-applied dicamba," *Weed Sci.*, 35:846-852, 1987.

Markus et al., "Purification and some properties of component A of the 4-chlorophenylacetate 3,4-dioxygenase from *Pseudomonas* species strain CBS," *J. of Biol. Chem.*, 261(27):12883-12888, 1986.

Mason et al., "The electron-transport proteins of hydroxylating bacterial dioxygenases," *Ann. Rev. of Microbiology*, 46:277-305, 1992.

Peniuk et al., "Physiological investigations into the resistance of a wild mustard (*Sinapis arvensis* L.) biotype to auxinic herbicides," *Weed Research*, 33:431-440, 1993.

Sarpe et al., "Researches on resistance of maize hybrids and inbred lines to the herbicides based on 2,4-D and dicamba," *Fragmenta Herbologica Jugoslavica*, 16(1-2):299-305, 1987.

Schroeder et al., "Soft red winter wheat (*Triticum aestivum*) response to dicamba and dicamba plus 2,4-D," *Weed Technology*, 3:67-71, 1989.

Sprague, "Avoid herbicide spray tank contamination," *IPM News*, ipmnews.msu.edu/fieldcrop/tabid/56, Mar. 24, 2010.

Thompson et al., "Soybean tolerance to early preplant applications of 2,4-D ester, 2,4-D amine, and dicamba," *Weed Technology*, 21:882-885, 2007.

Office Action regarding U.S. Appl. No. 11/758,653 dated Dec. 29, 2009.

Amendment and Response to Office Action regarding U.S. Appl. No. 11/758,653, dated Mar. 29, 2010.

Final Office Action regarding U.S. Appl. No. 11/758,653, dated Jun. 24, 2010.

Amendment and Response to Final Office Action regarding U.S. Appl. No. 11/758,653, dated Aug. 16, 2010.

Office Action regarding U.S. Appl. No. 11/758,656 dated Sep. 15, 2009.

Response to Office Action regarding U.S. Appl. No. 11/758,656 dated Dec. 17, 2009.

Final Office Action regarding U.S. Appl. No. 11/758,656, dated Apr. 14, 2010.

Declaration of Yuechun Wan Under 37 C.F.R. §1.132, dated Aug. 11, 2010.

Notice of Allowance regarding U.S. Appl. No. 11/758,656, dated Oct. 4, 2010.

Office Action regarding U.S. Appl. No. 11/758,657 dated Sep. 2, 2009.

Response to Office Action regarding U.S. Appl. No. 11/758,657 dated Jan. 4, 2010.

Final Office Action regarding U.S. Appl. No. 11/758,657, dated Apr. 14, 2010.

Response to Final Office Action regarding U.S. Appl. No. 11/758,657, dated Jul. 14, 2010.

Notice of Allowance regarding U.S. Appl. No. 11/758,657, dated Sep. 10, 2010.

Office Action regarding U.S. Appl. No. 11/758,659 dated Nov. 24, 2009.

Amendment and Response to Office Action regarding U.S. Appl. No. 11/758,659, dated May 24, 2010.

Notice of Allowance regarding U.S. Appl. No. 11/758,659, dated Aug. 3, 2010.

Office Action regarding U.S. Appl. No. 10/330,662 dated Apr. 18, 2006.

Interview Summary regarding U.S. Appl. No. 10/330,662, dated Sep. 13, 2006.

Declaration of Donald P. Weeks regarding U.S. Appl. No. 10/330,662, dated Oct. 18, 2006.

Amendment and Response to Office Action regarding U.S. Appl. No. 10/330,662, dated Oct. 18, 2006.

Terminal Disclaimer filed in U.S. Appl. No. 10/330,662, dated Oct. 18, 2006.

Final Office Action regarding U.S. Appl. No. 10/330,662, dated Jan. 10, 2007.

Amendment and Response to Office Action regarding U.S. Appl. No. 10/330,662, dated Jul. 9, 2007.

Amendment regarding U.S. Appl. No. 10/330,662, dated Jul. 20, 2007.

Office Action regarding U.S. Appl. No. 10/330,662, dated Sep. 21, 2007.

Declaration of Donald P. Weeks regarding U.S. Appl. No. 10/330,662, dated Feb. 20, 2008.

Amendment and Response to Office Action regarding U.S. Appl. No. 10/330,662, dated Mar. 20, 2008.

Office Action regarding U.S. Appl. No. 10/330,662, dated Jul. 9, 2008.

Amendment and Remarks regarding U.S. Appl. No. 10/330,662, dated Jan. 9, 2009.

Final Office Action regarding U.S. Appl. No. 10/330,662, dated Apr. 24, 2009.

Amendment and Remarks regarding U.S. Appl. No. 10/330,662, dated Sep. 24, 2009.

Office Action regarding U.S. Appl. No. 10/330,662, dated Jan. 11, 2010.

Interview Summary regarding U.S. Appl. No. 10/330,662, dated Mar. 19, 2010.

Amendment and Remarks regarding U.S. Appl. No. 10/330,662, dated May 4, 2010.

Notice of Allowance regarding U.S. Appl. No. 10/330,662, dated Jul. 12, 2010.

Notice of Allowance regarding U.S. Appl. No. 11/758,653, dated Oct. 5, 2010.

Office action dated Dec. 22, 2010, in Honduran Patent Application No. 2009-00795.

English translation of office action dated Dec. 22, 2010, in Honduran Patent Application No. 2009-00795.

* cited by examiner

CROPPING SYSTEMS FOR MANAGING WEEDS

This application claims the priority of U.S. Provisional Patent Application 60/862,907, filed Oct. 25, 2006, the disclosure of which is incorporated herein by reference in its entirety.

BACKGROUND OF THE INVENTION

1. Field of the Invention

The invention relates generally to the field of weed management. More specifically, the invention relates to methods for pre-emergent and post-emergent herbicide use for controlling weeds in combination with transgenic crops tolerant to one or more herbicides.

2. Description of the Related Art

Weeds cost farmers billions of dollars annually in crop losses and the expense of efforts to keep weeds under control. Weeds also serve as hosts for crop diseases and insect pests. The losses caused by weeds in agricultural production environments include decreases in crop yield, reduced crop quality, increased irrigation costs, increased harvesting costs, decreased land value, injury to livestock, and crop damage from insects and diseases harbored by the weeds. The damage caused can be significant. For example, it is estimated that between 1972 and 1976 corn yields were reduced by about 10% due to weeds (Chandler, 1981).

Chemical herbicides have provided an effective method of weed control over the years. Herbicides can generally be applied pre-emergence and/or post-emergence. Pre-emergence herbicides are applied in a field before a crop emerges from the soil. Such applications are typically applied to the soil before or soon after planting the crop. Such applications may kill weeds that are growing in the field prior to the emergence of the crop, and may also prevent or reduce germination of weed seeds that are present in the soil. Post-emergence herbicides are typically used to kill weeds after a crop has emerged in the field. Such applications may kill weeds in the field and prevent or reduce future weed seed production and germination.

One weed control strategy is to apply an herbicide such as dicamba to a field before sowing seeds. However, after applying the herbicide to a field, a farmer has to wait at least several weeks before sowing the field with crop seeds such that the herbicide has killed most of the weeds and has degraded so as not injure the sown crop. For example, plants are especially sensitive to dicamba and it has been recommended that dicamba formulations such as Banvel™, Clarity™, or Sterling™ be applied, for instance, 30 days prior to planting for controlling weeds.

Another method that has been successfully used to manage weeds combines herbicide treatments with crops that are tolerant to the herbicide. In this manner, a herbicide that would normally injure a crop can be applied before and during growth of the crop without causing damage. Thus, weeds may be effectively controlled and new weed control options are made available to the grower.

In recent years, the availability of transgenic crops having traits providing tolerance to a herbicide or herbicides with one mode of action has simplified weed management for growers. For example, crops tolerant to 2,4-dichlorophenoxyacetic acid (Streber and Willmitzer, 1989), bromoxynil (Stalker et al., 1988), glyphosate (Comai et al., 1985) and phosphinothricin (De Block et al., 1987) have been developed. However, this strategy has increased the possibility of selection for and spread of weed biotypes resistant to a particular herbicide in a particular cropping system. Therefore, there is a need in the art for inventing cropping systems that use transgenic crops providing tolerance to one or more herbicides for managing weeds i.e., for managing current herbicide resistant weeds, for managing tough weeds, for managing volunteer plants, and for minimizing the development of herbicide resistant weeds in the future.

It is also known in the art that the risk of developing resistant weeds is higher with certain types of herbicides and lower with certain other types. For the following discussion, herbicides are classified according to their modes-of-action based on the HRAC or WSSA schemes (Table 2). For example, the risk of developing resistant weeds is thought to be higher with herbicides belonging to groups such as acetolactate synthase (ALS) inhibitors (Group 2 or B) and acetyl CoA carboxylase (ACCase) inhibitors (Group 1 or A). The risk of developing resistant weeds is thought to be lower with herbicides belonging to groups such as PS II inhibitors (Group 5 or C1), microtubule assembly inhibitors (Group 3 or K1), and lipid synthesis inhibitors (Group or N). The risk of developing resistant weeds is thought to be still lower with herbicides belonging to groups such as synthetic auxins (Group 4 or O), glycines (Group 9 or G), and inhibitors of glutamine synthetase (Group 10 or H) (Légère et al., 2006.). Hence it is desirable to develop cropping systems utilizing crops tolerant to low-risk herbicides and their accompanying herbicide treatments for minimizing populations of herbicide resistant weeds.

Dicamba is one member of a class of herbicides commonly referred to as "auxin-like" herbicides or "synthetic auxins." Dicamba has been used as a pre-emergence herbicide (e.g. 14-30 days prior to planting) in dicots and as a pre- and/or post-emergence herbicide in corn, sorghum, small grains, pasture, hay, rangeland, sugarcane, asparagus, turf, and grass seed crops to effectively control annual and perennial broadleaf weeds and several grassy weeds (*Crop Protection Chemicals Reference*, 1995). Unfortunately, dicamba can injure many commercial crops including beans, soybeans, cotton, peas, potatoes, sunflowers, tomatoes, tobacco, and fruit trees, ornamental plants and trees, and other broadleaf plants when it comes into contact with them. Soybean and cotton are particularly sensitive to dicamba. Thus, applications of dicamba must generally occur several weeks before planting of sensitive crops to ensure that residual dicamba is sufficiently cleared from the crop environment before crops emerge.

Recently, sequences encoding a multicomponent dicamba demethylase, including a monooxygenase (DMO), were isolated from *Pseudomonas maltophilia* (U.S. Patent Application Nos: 20030115626; 20030135879; U.S. Pat. No. 7,022,896) which is involved in the conversion of an herbicidal form of the herbicide dicamba (3,6-dichloro-o-anisic acid; a formulation of which is sold, for instance, under the trade name Banvel™) to a non-toxic 3,6-dichlorosalicylic acid (Wang et al., 1997). The inventors reported the transformation of the sequences into tobacco and *Arabidopsis*. The transformed plant tissue was selected on kanamycin and regenerated into a plant. However, herbicide tolerance was not demonstrated or suggested in immature tissues or seedlings or in other plants. Pre-emergence herbicide applications were also not described.

U.S. Pat. No. 6,376,754 describes plants, such as soybean plants, having tolerance to at least two herbicides. Included among these herbicides are glyphosate, glufosinate, and a sulfonylurea (i.e. an acetolactate synthase (ALS) inhibitor) herbicide. U.S. Pat. No. 6,586,367 describes methods to control weeds, and plants with tolerance to glyphosate or glufosinate, which may be treated with glyphosate or glufosinate, and additionally with an amount of an herbicide or herbicides selected from the group consisting of atrazine, dicamba, and other selected herbicides. However plants and cropping systems comprising a genetic trait conferring tolerance to dicamba are not described.

WO2005/107437 discloses combining a first herbicide tolerant gene i.e., a 2,4-D tolerance gene with a second herbicide tolerant gene i.e., a glyphosate tolerance gene or other herbicide tolerant gene. It does not disclose combining a glyphosate tolerant gene with a dicamba tolerant gene and a 2,4-D tolerant gene. Furthermore, it does not disclose cropping systems of the present invention for managing weeds, herbicide resistant weeds, tough to control weeds, herbicide resistant volunteer crop plants, and for minimizing the potential of herbicide resistant weeds in the future. It also does not disclose methods for minimizing development of herbicide resistant weeds in the future by rotating herbicide tolerant crops and use of their corresponding herbicide(s).

SUMMARY OF THE INVENTION

In one aspect, the invention provides a cropping system for managing weed growth in a crop-growing environment comprising: a) planting in a crop growing environment a crop seed that germinates into a crop plant comprising tolerance to an auxin-like herbicide; and b) applying at least a first herbicide treatment to the crop growing environment to control weed growth, wherein the herbicide treatment is selected from the group consisting of the first, second, third, fourth and fifth treatment set forth in Table 3, and wherein the treatment comprises an amount of herbicide effective to control weed growth without significantly damaging the crop seed or crop plant. In specific embodiments, the method may comprise applying at least two, at least three, at least four and/or each of said herbicide treatments.

In one embodiment, a used with a system of the invention plant comprises a transgene conferring herbicide tolerance to glyphosate or 2,4-D. An example of a transgene conferring herbicide tolerance to glyphosate is one encoding a protein selected from the group consisting of glyphosate resistant 5-enolpyruvylshikimate-3-phosphate synthase (EPSPS), glyphosate oxidoreductase (GOX), glyphosate-N-acetyl transferase (GAT) and glyphosate decarboxylase. In the system, the crop plant may comprise tolerance to an auxin-like herbicide comprises a transgene encoding DMO and/or AAD-1. In certain embodiments, the GAT protein is GAT4601 (SEQ ID NO:2), and may be encoded by a transgene comprising the nucleic acid sequence of SEQ ID NO:1. In a particular embodiment, expression of a GAT protein is accomplished by use of the SCP1 promoter.

In particular embodiments, a system of the invention is defined as comprising the step of applying a third herbicide treatment at the late post-emergence stage comprising a herbicidally effective amount of a herbicide selected from the group consisting of an auxin-like herbicide, a graminicide, a post-emergent selective herbicide, and a combination thereof. In a further embodiment, a system of the invention comprises the step of applying a fourth herbicide treatment at the pre-harvest stage comprising a herbicidally effective amount of a herbicide selected from the group consisting of glyphosate, an auxin-like herbicide, a post-emergent selective herbicide, paraquat, and a combination thereof. In yet another embodiment, the system comprises the step of harvesting the seeds from the crop plant after fourth treatment. The system may also comprise the step of applying a fifth herbicide treatment at the post-harvest stage comprising a herbicidally effective amount of a herbicide selected from the group consisting of glyphosate, an auxin-like herbicide, paraquat, a pre-emergent selective residual herbicide, and a combination thereof.

An auxin-like herbicide may be selected from the group consisting of dicamba, 2,4-D, and a combination thereof. In one embodiment, the crop plant is a dicot plant, examples of which include cotton and soybeans. The system may in particular comprise applying an amount of herbicide set forth in Table 4 and/or 5 for the respective herbicide(s). The system may also further comprise the step of applying a third herbicide treatment at the late post-emergence stage comprising a herbicidally effective amount of a herbicide selected from the group consisting of glyphosate, an auxin-like herbicide, a graminicide, a post-emergent selective herbicide, and a combination thereof. The system may still further comprise the step of applying a fourth herbicide treatment at the pre-harvest stage comprising a herbicidally effective amount of a herbicide selected from the group consisting of glyphosate, an auxin-like herbicide, a post-emergent selective herbicide, paraquat, and a combination thereof. A system of the invention may also comprise the step of harvesting the seeds from the crop plant after fourth treatment.

In one embodiment of the invention, the herbicide is selected from the group consisting of dicamba, 2,4-D, and a combination thereof. In a cropping system of the invention, the herbicide treatment may control the growth of a herbicide resistant weed selected from the group consisting of: *Alopecurus myosuroides, Avena fatua, Avena sterilis, Avena sterilis ludoviciana, Brachiaria plantaginea, Bromus diandrus, Bromus rigidus, Cynosurus echinatus, Digitaria ciliaris, Digitaria ischaemum, Digitaria sanguinalis, Echinochloa colona, Echinochloa crus-galli, Echinochloa oryzicola, Echinochloa phyllopogon, Eleusine indica, Eriochloa punctata, Hordeum glaucum, Hordeum leporinum, Ischaemum rugosum, Leptochloa chinensis, Lolium multiflorum, Lolium perenne, Lolium persicum, Lolium rigidum, Phalaris minor, Phalaris paradoxa, Rottboellia exalta, Setaria faberi, Setaria viridis, Setaria viridis* var. *robusta-alba schreiber, Setaria viridis* var. *robusta-purpurea, Snowdenia polystachea, Sorghum halepense, Sorghum sudanese, Alisma plantago-aquatica, Amaranthus blitoides, Amaranthus hybridus, Amaranthus lividus, Amaranthus palmeri, Amaranthus powellii, Amaranthus quitensis, Amaranthus retroflexus, Amaranthus rudis, Amaranthus tuberculatus, Ambrosia artemisiifolia, Ambrosia trifida, Ammania auriculata, Ammania coccinea, Anthemis cotula, Apera spica-venti, Bacopa rotundifolia, Bidens pilosa, Bidens subalternans, Brassica tournefortii, Bromus tectorum, Camelina microcarpa, Chenopodium album, Chrysanthemum coronarium, Conyza bonariensis, Conyza canadensis, Cuscuta campestris, Cyperus difformis, Damasonium minus, Descurainia sophia, Diplotaxis tenuifolia, Echium plantagineum, Elatine triandra* var. *pedicellata, Euphorbia heterophylla, Fallopia convolvulus, Fimbristylis miliacea, Galeopsis tetrahit, Galium spurium, Helianthus annuus, Iva xanthifolia, Ixophorus unisetus, Kochia scoparia, Lactuca serriola, Limnocharis flava, Limnophila erecta, Limnophila sessiliflora, Lindernia dubia, Lindernia dubia* var. *major, Lindernia micrantha, Lindernia procumbens, Mesembryanthemum crystallinum, Monochoria korsakowii, Monochoria vaginalis, Neslia paniculata, Papaver rhoeas, Parthenium hysterophorus, Pentzia suffruticosa, Phalaris minor, Raphanus raphanistrum, Raphanus sativus, Rapistrum rugosum, Rotala indica* var. *uliginosa, Sagittaria guyanensis, Sagittaria montevidensis, Sagittaria pygmaea, Salsola iberica, Scirpus juncoides* var. *ohwianus, Scirpus mucronatus, Setaria lutescens, Sida spinosa, Sinapis arvensis, Sisymbrium orientale, Sisymbrium thellungii, Solanum*

*ptycanthum, Sonchus asper, Sonchus oleraceus, Sorghum bicolor, Stellaria media, Thlaspi arvense, Xanthium strumarium, Arctotheca calendula, Conyza sumatrensis, Crassocephalum crepidiodes, Cuphea carthagenenis, Epilobium adenocaulon, Erigeron philadelphicus, Landoltia punctata, Lepidium virginicum, Monochoria korsakowii, Poa annua, Solanum americanum, Solanum nigrum, Vulpia bromoides, Youngia japonica, Hydrilla verticillata, Plantago lanceolata, Carduus nutans, Carduus pycnocephalus, Centaurea solstitialis, Cirsium arvense, Commelina diffusa, Convolvulus arvensis, Daucus carota, Digitaria ischaemum, Echinochloa crus-pavonis, Fimbristylis miliacea, Galeopsis tetrahit, Galium spurium, Limnophila erecta, Matricaria perforate, Papaver rhoeas, Ranunculus acris, Soliva sessilis, Sphenoclea zeylanica, Stellaria media, Nassella trichotoma, Stipa neesiana, Agrostis stolonifera, Polygonum aviculare, Alopecurus japonicus, Beckmannia syzigachne, Bromus tectorum, Chloris inflate, Echinochloa erecta, Portulaca oleracea,* and *Senecio vulgaris*. The cropping system may further comprise the step of identifying a tough weed in the crop growing region and applying a herbicide treatment effective to control the tough weed, wherein tough weed is selected from the group consisting of *Abutilon theophrasti, Amaranthus* sp., *Amaranthus palmeri, Ambrosia artimisiifolia, Ambrosia trifida, Chenopodium album, Convolvulus arvensis, Conyza canadensis, Commelina* sp., *Commelina benghalensis, Ipomoea* sp., *Kochia* sp., *Polygonum convolvulus, Lolium rigidum, Sida spinosa,* and *Solanum ptycanthum*. In one embodiment, the crop seed is a seed of a soybean or cotton plant.

In another aspect, the invention provides a cropping system as described herein that further comprises: a) identifying within the crop growing region a herbicide-resistant weed tolerant to at least the first herbicide treatment; and b) applying an amount of an auxin-like herbicide and/or glyphosate effective to control the herbicide resistant weed.

In yet another aspect, the invention provides a cropping system for minimizing the development of a herbicide resistant weed in a crop-growing environment comprising: a) planting in a field a crop plant having tolerance to glyphosate and auxin-like herbicides; b) applying at least a first herbicide treatment comprising glyphosate and/or an auxin-like herbicide to the crop growing environment to control weeds; d) identifying a location in the field infested with weeds resistant to glyphosate or an auxin-like herbicide; and e) applying an amount of glyphosate and/or the auxin-like herbicide effective to control the weeds resistant to glyphosate or an auxin-like herbicide. The plant may comprise a transgene conferring herbicide tolerance to glyphosate. The transgene conferring herbicide tolerance to glyphosate may encode a protein selected from the group consisting of glyphosate resistant 5-enolpyruvylshikimate-3-phosphate synthase (EPSPS), glyphosate oxidoreductase (GOX), glyphosate-N-acetyl transferase (GAT) and glyphosate decarboxylase. The crop plant may comprise a transgene encoding DMO. In a particular embodiment, the GAT protein is GAT4601 (SEQ ID NO:2), or is encoded by a transgene comprising SEQ ID NO:1.

In yet another aspect, the invention provides a method for minimizing the development of a herbicide resistant weed comprising: rotating a first cropping system in a first growing season with a second cropping system in a subsequent growing season, wherein the first and second cropping systems comprise a cropping system according to claim 1. In the method the crop plant in the first cropping system may possess at least one different herbicide tolerance relative to the crop plant in the second cropping system. In one embodiment, the crop plant in the first cropping system and the crop plant in the second cropping system comprise herbicide tolerances as set forth in Table 7. In another embodiment, the crop plant in the first and second cropping systems are tolerant to at least one herbicide selected from the group consisting of glyphosate, glufosinate, dicamba, 2,4-D and a combination thereof. In specific embodiments, the crop plant in selected from the group consisting of corn, cotton and soybean. The crop plant in the first cropping system and crop plant in the second cropping system may be of the same or different species.

DETAILED DESCRIPTION OF THE INVENTION

The following is a detailed description of the invention provided to aid those skilled in the art in practicing the present invention. Those of ordinary skill in the art may make modifications and variations in the embodiments described herein without departing from the spirit or scope of the present invention.

The invention relates, in one aspect, to a method for growing crop plants that comprises employing one or more herbicides to control the growth of one or more weed species. The invention provides superior weed control options, including reduction and/or prevention of herbicide tolerance in weeds (Table 1).

In one embodiment, an effective amount of a first herbicidal treatment (e.g. to control weeds) is applied to the crop growing environment prior to planting or at planting or prior to germination or a combination thereof of the crop. Exemplary herbicides classified according to modes of action are given in Table 2. One or more herbicides for the first treatment of the second crop may be selected, depending upon the tolerance exhibited by the crop and depending upon the presence of a particular weed species in the field, from herbicides belonging to the groups approved by Weed Science Society of America (WSSA).

In certain embodiments, one or more herbicides for the first treatment of the crop are selected from the following herbicides:

a) inhibitors of EPSP synthesis (Group 9) including glyphosate. Exemplary application rates for glyphosate herbicides, their trade names, and suppliers are shown in Table 4 for soybean and Table 5 for cotton.

b) inhibitors of glutamine synthetase (GS) (Group 10) including glufosinate. For soybean the application rate for glufosinate (Liberty™, Bayer CropScience) may be 28-34 oz/A or a maximum of 0.809 lbs ai/A per season. For cotton, the application rate for glufosinate (Liberty, Bayer CropScience) is, for example, 28-34 oz/A.

c) synthetic auxins or auxin-like herbicides (Group 4) including dicamba and 2,4-D. Application rates for these herbicides, their trade names, and suppliers are shown in Table 4 for soybean and Table 5 for cotton.

Pre-emergent crop selective residual herbicides may be selected from:

d) Acetanilides (AA; Group 15) are a family of selective herbicides that are currently thought to control weeds by inhibiting very long chain fatty acid synthesis. Examples of selective AA for soybean and cotton, application rates, trade names, and suppliers are shown in Tables 4 and 5, respectively. Formulations comprising acetochlor (e.g. Harness®, Monsanto; Surpass®, Surpass® EC, Dow) may also be utilized.

e) Acetolactate synthase inhibitors (ALS; Group 2) are a family of selective herbicides that control weeds by inhibiting the formation of branched-chain amino acid synthesis.

Examples of ALS for soybean and cotton, application rates, trade names, and suppliers are shown in Table 4 and 5, respectively.

f) Dinitroanilines (DiNA; Group 3) are a family of selective herbicides that control weeds by binding to tubulin, thereby leading to loss of microtubules in a cell. Examples of selective DiNA herbicides for soybean and cotton, application rates, trade names, and suppliers are shown in Table 4 and 5, respectively.

g) Protoporphyrinogen-oxidase (PPG-oxidase; Group 14) inhibitors (PPO) are a family of selective herbicides that control weeds by inhibiting PPG-oxidase in chloroplasts and mitochondria, thereby blocking chlorophyll and heme synthesis and leading to excessive formation of the singlet oxygen-generating protophorphyrin IX, eventually leading to disruptions in cell membranes. Examples of PPO herbicides for soybean and cotton are shown in Table 4 and 5, respectively, including application rates, trade names, and suppliers.

Non-limiting examples of herbicides that may be used in combination with dicamba on cotton include: glyphosate, pendimethalin (e.g. PROWL, PENDIMAX), Diuron, 2,4-D, carfentrazone-ethyl, fluometuron, MSMA (monosodium methanearsonic acid and salts), prometryn, pyrithiobac-sodium, metolachlor, acetochlor, trifloxysulfuron, fomesafen, flumioxazin, and sethoxydim (e.g. POAST). Herbicides may be applied to crop plants pre-emergence or post-emergence ("over the top") as appropriate. Thus, preferable pre-emergence herbicides that may be used with dicamba on DMO cotton (i.e. cotton comprising a dicamba monooxygenase transgene specifying tolerance to dicamba) may include glyphosate, pendimethalin, diuron, carfentrazone ethyl, fluometuron, prometryn, flumioxazin, and fomesafen, among others. Prefereable post-emergence herbicides for use with dicamba on DMO cotton may include glyphosate, trifloxysulfuron, metolachlor, acetochlor, fomesafen, pyrithiobac-sodium, and sethoxydim, among others.

Non-limiting examples of herbicides for use with dicamba on corn are shown in Table 6.

Non-limiting examples of herbicides that may be used in combination with dicamba on soybean include: glyphosate, 2,4-D, chlorimuron-ethyl, clethodim, fluazifop P-butyl, flumioxazin (e.g. VALOR), fomesafen (e.g. FLEXSTAR, REFLEX), imazethapyr (e.g. LIGHTNING), metribuzin (e.g. SENCOR), and pendimethalin. Premixes and tank mixes with dicamba may be employed, as well as separate applications of dicamba and another active ingredient. Non-limiting exemplary premix herbicides include combinations of dicamba and atrazine (e.g. MARKSMAN), dicamba and diflufenzopyr (e.g. DISTINCT), and dicamba and primisulfuron (e.g. NORTHSTAR).

In certain embodiments, one or more herbicides for the first treatment of the crop may be selected from at least one low-risk herbicide such as EPSP synthesis inhibitors, GS inhibitors, and auxin-like herbicides. In particular embodiments the herbicide may be glyphosate, glufosinate, dicamba, or 2,4-D depending upon the tolerance exhibited by the crop and presence of a weed species in the crop. Additionally, a pre-emergent herbicide and paraquat may be used. If more than one herbicide is used then they may be applied sequentially or as a mixture.

Once the seeds from the crop have germinated, a second treatment of a herbicidally effective amount may be applied to the crop growing environment of the crop at early post-emergence stage. One or more herbicides for the second herbicide treatment may be selected from herbicides belonging to the groups approved by Weed Science Society of America (WSSA) (e.g. Table 2) depending upon the type of tolerance exhibited by the crop and type of weed species present in the crop. Preferably, one or more herbicides for the second treatment of the crop may be selected from at least one low-risk herbicide such as EPSP synthesis inhibitors, GS inhibitors, and auxin-like herbicides, and a graminicide, or a crop selective post-emergent herbicide. Examples of these herbicides, application rates, trade names, and suppliers are shown in Table 4 for soybean and Table 5 for cotton. In certain embodiments, one or more herbicides for the second herbicide treatment may be selected from glyphosate, glufosinate, dicamba, and 2,4-D, and a graminicide, or a crop selective post-emergence herbicides. In particular embodiments, one or more herbicides may be selected from glyphosate, glufosinate, dicamba, or 2,4-D depending upon the tolerance exhibited by the crop and the presence of a weed species in the crop. If more than one herbicide is used then they may be applied sequentially or as a mixture.

The second herbicidal treatment may be followed by an herbicidally effective amount of a third herbicide treatment at late post-emergence stage. The third treatment is similar to the second treatment.

After the third treatment, a herbicidally effective amount of a fourth treatment may be applied at pre-harvest stage. One or more herbicides for the fourth herbicide treatment may be selected from herbicides belonging to the groups approved by Weed Science Society of America (WSSA) as cited above depending upon the type of tolerance exhibited by the crop and type of weed species present in the crop. In certain embodiments, one or more herbicides for the fourth treatment may be selected from at least one low-risk herbicide such as EPSP synthesis inhibitors, GS inhibitors, auxin-like herbicides, and a crop selective post-emergence herbicide. Examples of these herbicides, application rates, trade names, and suppliers are shown in Table 4 for soybean and Table 5 for cotton. In particular embodiments, one or more herbicides are selected from glyphosate, glufosinate, dicamba, or 2,4-D depending upon the tolerance exhibited by the crop and the presence of a weed species present in the crop.

After the fourth treatment, a herbicidally effective amount of a fifth treatment may be applied at a post-harvest stage. This treatment may be applied in fall or spring, applied between a fallow period, or applied between a crop planting in double crop planting situations. One or more herbicides for the fifth treatment may be selected from herbicides belonging to the groups approved by Weed Science Society of America (WSSA) as cited above depending upon the type of tolerance exhibited by the crop and type of weed species present in the crop. In certain embodiments, one or more herbicides for the fifth treatment is selected from at least one low-risk herbicide such as EPSP synthesis inhibitors, GS inhibitors, auxin-like herbicides, or paraquat, or a crop selective pre-emergence herbicide. Examples of these herbicides, application rates, trade names, and suppliers are shown in Table 4 for soybean and Table 5 for cotton. In particular embodiments, one or more herbicides are selected from glyphosate, glufosinate, dicamba, or 2,4-D depending upon the tolerance exhibited by the crop and the presence of a weed species in the crop.

A graminicide is not typically used with corn unless the corn has tolerance to it, for instance a "fops" herbicides used for controlling grasses. Such tolerance can be provided by a gene encoding AAD-1. Non-limiting examples of fops herbicides include fluazifop-p-butyl, sold under the trade name of FUSILADE (Syngenta), e.g. FUSILADE 2000, FUSILADE DX, FUSILADE FIVE, FUSILADE SUPER, FUSION, HORIZON, ORNAMEC, PP005, TORNADO, and FUSIFLEX.

In some embodiments of the present invention, a combination of two treatments is selected from the first to fifth treatments. For example, only the first and second treatment, or the first or third treatment, or the second and third treatments, or the fifth and second or third treatments are applied to manage weeds.

In one embodiment of the present invention, one or more treatments of one or more different mode of action herbicides are applied to the crop tolerant to one or more herbicides for managing weeds.

In another embodiment of the cropping system of the present invention, no first or fifth treatment is applied. Instead these were replaced by mechanical methods such as tilling. The tilling is done by methods well known in the art. Preferably, tilling is done in fall or spring.

In yet another embodiment of the cropping system of the present invention, both first and fifth herbicidal treatments and tilling can be combined to obtain better weed management.

In yet another embodiment, the cropping system of the present invention is practiced for managing herbicide resistant weeds in a crop-growing environment of a crop involving a further step of identifying a herbicide resistant weed. In specific embodiments the weed is selected from the group consisting of: *Alopecurus myosuroides, Avena fatua, Avena sterilis, Avena sterilis ludoviciana, Brachiaria plantaginea, Bromus diandrus, Bromus rigidus, Cynosurus echinatus, Digitaria ciliaris, Digitaria ischaemum, Digitaria sanguinalis, Echinochloa colona, Echinochloa crus-galli, Echinochloa oryzicola, Echinochloa phyllopogon, Eleusine indica, Eriochloa punctata, Hordeum glaucum, Hordeum leporinum, Ischaemum rugosum, Leptochloa chinensis, Lolium multiflorum, Lolium perenne, Lolium persicum, Lolium rigidum, Phalaris minor, Phalaris paradoxa, Rottboellia exalta, Setaria faberi, Setaria viridis, Setaria viridis* var. *robusta-alba Schreiber, Setaria viridis* var. *robusta-purpurea, Snowdenia polystachea, Sorghum halepense, Sorghum sudanese, Alisma plantago-aquatica, Amaranthus blitoides, Amaranthus hybridus, Amaranthus lividus, Amaranthus palmeri, Amaranthus powellii, Amaranthus quitensis, Amaranthus retroflexus, Amaranthus rudis, Amaranthus tuberculatus, Ambrosia artemisiifolia, Ambrosia trifida, Ammania auriculata, Ammania coccinea, Anthemis cotula, Apera spica-venti, Bacopa rotundifolia, Bidens pilosa, Bidens subalternans, Brassica tournefortii, Bromus tectorum, Camelina microcarpa, Chenopodium album, Chrysanthemum coronarium, Conyza bonariensis, Conyza canadensis, Cuscuta campestris, Cyperus difformis, Damasonium minus, Descurainia sophia, Diplotaxis tenuifolia, Echium plantagineum, Elatine triandra* var. *pedicellata, Euphorbia heterophylla, Fallopia convolvulus, Fimbristylis miliacea, Galeopsis tetrahit, Galium spurium, Helianthus annuus, Iva xanthifolia, Ixophorus unisetus, Kochia scoparia, Lactuca serriola, Limnocharis flava, Limnophila erecta, Limnophila sessiliflora, Lindernia dubia, Lindernia dubia* var. *major, Lindernia micrantha, Lindernia procumbens, Mesembryanthemum crystallinum, Monochoria korsakowii, Monochoria vaginalis, Neslia paniculata, Papaver rhoeas, Parthenium hysterophorus, Pentzia suffruticosa, Phalaris minor, Raphanus raphanistrum, Raphanus sativus, Rapistrum rugosum, Rotala indica* var. *uliginosa, Sagittaria guyanensis, Sagittaria montevidensis, Sagittaria pygmaea, Salsola iberica, Scirpus juncoides* var. *ohwianus, Scirpus mucronatus, Setaria lutescens, Sida spinosa, Sinapis arvensis, Sisymbrium orientale, Sisymbrium thellungii, Solanum ptycanthum, Sonchus asper, Sonchus oleraceus, Sorghum bicolor, Stellaria media, Thlaspi arvense, Xanthium strumarium, Arctotheca calendula, Conyza sumatrensis, Crassocephalum crepidiodes, Cuphea carthagenenis, Epilobium adenocaulon, Erigeron philadelphicus, Landoltia punctata, Lepidium virginicum, Monochoria korsakowii, Poa annua, Solanum americanum, Solanum nigrum, Vulpia bromoides, Youngia japonica, Hydrilla verticillata, Plantago lanceolata, Carduus nutans, Carduus pycnocephalus, Centaurea solstitialis, Cirsium arvense, Commelina diffusa, Convolvulus arvensis, Daucus carota, Digitaria ischaemum, Echinochloa crus-pavonis, Fimbristylis miliacea, Galeopsis tetrahit, Galium spurium, Limnophila erecta, Matricaria perforate, Papaver rhoeas, Ranunculus acris, Soliva sessilis, Sphenoclea zeylanica, Stellaria media, Nassella trichotoma, Stipa neesiana, Agrostis stolonifera, Polygonum aviculare, Alopecurus japonicus, Beckmannia syzigachne, Bromus tectorum, Chloris inflate, Echinochloa erecta, Portulaca oleracea,* and *Senecio vulgaris.*

In another embodiment, the cropping system of the present invention is practiced for managing an herbicide-resistant volunteer plant further involving a step of identifying an herbicide-resistant volunteer to glyphosate or an auxin-like herbicide. The herbicide resistant volunteer may belong to one or more of the following plant species: corn, rice, cotton, sorghum, wheat, barley, turfgrass, oats, alfalfa, sugar beets, potatoes, beans, peas, millet, flax, peanuts, rapeseed, and soybeans.

In yet another embodiment, the cropping system of the present invention is practiced for managing tough weeds in a crop-growing environment of a crop. The embodiment may further involve the step of identifying a tough weed including, among others, the following: *Abutilon theophrasti, Amaranthus* sp., *Amaranthus palmeri, Ambrosia artimisiifolia, Ambrosia trifida, Chenopodium album, Convolvulus arvensis, Conyza canadensis, Commelina* sp., *Commelina benghalensis, Ipomoea* sp., *Kochia* sp., *Polygonum convolvulus, Lolium rigidum, Sida spinosa,* and *Solanum ptycanthum,* and applying an herbicidally effective amount of an herbicide that is active against the tough weed, wherein the crop is tolerant to the herbicide that is active against the tough weed.

In another embodiment, the cropping system of the present invention is practiced for minimizing the development of herbicide resistant weeds in a crop-growing environment of a crop. In one embodiment, this may involve spot application of an herbicide to which the herbicide resistant weed is susceptible. The method can be modified to select a population of at least one weed resistant to a first herbicide by applying the first herbicide over several growing seasons and then applying a second herbicide to kill the weeds resistant to the first herbicide in a subsequent growing season.

In still yet another embodiment of the present invention, a method for minimizing the development of an herbicide resistant weed is designed by rotating a first cropping system comprising a crop tolerant to one or more low-risk herbicides and accompanying herbicidal treatments with a second cropping system comprising a crop tolerant to one or more low-risk herbicides and accompanying herbicidal treatments. For example, if the crop in the first cropping system is tolerant to glyphosate then the crop in the second cropping system can be tolerant to an auxin-like herbicide, such as dicamba, or tolerant to glyphosate and an auxin like herbicide. In an embodiment of this method, a first soybean crop tolerant to one or more low-risk herbicides is rotated with a second one or more low-risk herbicides tolerant crop selected from the group consisting of corn, rice, cotton, sorghum, wheat, barley, oats, alfalfa, sugar beets, potatoes, beans, peas, millet, rapeseed, and flax. In one embodiment, the method involves rotating soybean having tolerance to one or more herbicides with corn having tolerance to one or more herbicides.

In another embodiment of this method, a first cotton crop tolerant to one or more low-risk herbicides is rotated with a second one or more low-risk herbicides tolerant crop selected from the group consisting of corn, peanuts, soybeans, grain, and sorghum. In yet another embodiment, the method involves rotating a crop system comprising cotton having tolerance to one or more low risk herbicides with a crop system comprising cotton having tolerance to one or more herbicides. For example, if the first cotton crop is tolerant to glyphosate then the crop in the second cropping system may be tolerant to an auxin-like herbicide or tolerant to glyphosate and an auxin like herbicide. In the latter situation, the herbicide rotation may be practiced such that the weed control is maintained and so that the glyphosate resistant weed does not flourish in the "off" season i.e., without glyphosate during the rotation, and thereby become a worse problem. Using two herbicides simultaneously may be preferable, as the two herbicides may work at the same time without interfering or antagonizing each other.

In one embodiment, the crop in the cropping system of the present invention may be tolerant to at least one low-risk herbicide belonging to the WSSA mode of action groups 4, 9, or 15. In another embodiment, the crop is tolerant to an EPSP synthesis inhibitor, a GS inhibitor, and/or an auxin-like herbicide. In yet another embodiment, the crop is tolerant to glyphosate, glufosinate, dicamba, 2,4-D, or a combination thereof.

In one embodiment, the cropping systems disclosed herein employ transgenic crops having one or more transgenic traits providing tolerance to one or more different mode of action herbicides such as glyphosate, glufosinate, dicamba, or 2,4-D for managing weeds, including herbicide resistant weeds, tough weeds, herbicide resistant volunteer plants. These systems may also minimize the potential development of herbicide resistant weeds in the future. Further, the cropping systems of the present invention, in one embodiment, allow use of transgenic crops tolerant to one or more herbicides that are considered low risk herbicides thus further minimizing the potential of developing weeds resistant to those herbicides. In particular embodiments, the cropping systems utilize transgenic plants displaying tolerance to dicamba, glyphosate, and/or glufosinate.

Pre-emergent applications of auxin-like herbicides such as dicamba have previously required herbicide applications well in advance of planting and germination of plants susceptible to auxin-like herbicides to allow breakdown of the herbicide in the environment and avoid significant crop damage or death. Most crop plants, and particularly dicotyledonous plants such as soybeans and cotton are extremely sensitive to dicamba. Thus, the recommended post-application delays in planting by manufacturers must be closely followed. Use of crop plants displaying tolerance to one or more auxin-like herbicides such as 2,4-D or related compounds, and dicamba allows for application of such herbicides at or near the time of planting, It has been found, for example, that soybean plants transformed with dicamba monooxygenase (DMO)-encoding polynucleotide constructs were tolerant to even early pre-emergence application of dicamba, with less than 10% injury rates at even 9× the labeled application rate (5,040 g/ha, 4.5 lb/acre). It was found that, even using an 18× application rate of 10,080 g/ha (9 lb/acre), injury to transgenic dicamba tolerant plants was less than 20% (U.S. s/n 60/811,276, incorporated herein by reference). At an approximately 2× rate of application of 1122 g/ha, less than 2% injury was observed. It was therefore indicated the improved weed control associated with pre- and post-emergence applications of herbicides may be used without any significant decreases in productivity due to herbicide damage. Pre-emergent applications of dicamba to soybean, for instance, according to the invention may therefore be combined with one or more herbicide applications post-emergence to dicamba-tolerant plants, while maintaining crop yield and obtaining improved weed control. For example, one such herbicide application regime involves a late pre-emergence application of dicamba to soybean plants in conjunction with a post-emergence application of dicamba at the V2 stage of development. In certain embodiments, the post-emergence application may be carried out at any point from emergence to harvest. A particular embodiment comprises post-emergence application at any V stage until the soybean canopy closes, for example, at about the V1, V2, V3, V4, V5, V6 and/or later stages.

In one aspect, the invention provides a method for controlling weed growth in a field comprising: a) applying an herbicidally effective amount of an auxin-like herbicide to a crop-growing environment; and planting a transgenic seed of a crop plant expressing a nucleic acid encoding dicamba monooxygenase in soil of the crop-growing environment, wherein the seed germinates within 30 days or less days of applying the herbicide In certain embodiments, the seed germinates within four weeks, three weeks, two weeks, or less than one week after treating the growing environment with the auxin-like herbicide. The treated growing environment may be, for example, a field in which a crop is planted. A population of seeds of a plant tolerant to the auxin-like herbicide may be planted in the field. Treating the environment can be carried out according to known techniques in the art using, for example, commercially available formulations of auxin-like herbicides such as dicamba. The environment includes an area for which control of weeds is desired and in which the seed of a plant tolerant to the auxin-like herbicide can be planted. A weed can be directly contacted with herbicide in the environment and soil in the environment can be contacted with the herbicide, preventing or reducing weed growth in the soil. The step of treating the environment with a herbicide may be carried out before, after, or concurrently with the step of planting the soil with the transgenic seed. The transgenic seed may be planted into soil in the environment, for example, within 30 days before or after treatment, including from between about three weeks, two weeks, one week and 0 weeks before or after treatment, further including from between about 1, 2, 3, 4, 5, or 6 days before or after treatment, including concurrently with treatment. In the method, the seed may germinate, for example, from between about 30 days and 0 days after treating the environment, including between about 21, 18, 16, 14, 12, 10, 8, 6, 5, 4, 3, 2, 1 and about 0 days after treating the environment. The method may further comprise applying one or more additional treatments of an auxin-like herbicide after the seed germinates and/or the plant is growing.

In a method of the invention, the auxin-like herbicide may be selected from the group consisting of a phenoxy carboxylic acid compound, benzoic acid compound, pyridine carboxylic acid compound, quinoline carboxylic acid compound, and benazolinethyl compound. Examples of a phenoxy carboxylic acid compound include 2,4-dichlorophenoxyacetic acid (2,4-D), 4-(2,4-dichlorophenoxy) butyric acid (2,4-DB) and (4-chloro-2-methylphenoxy)acetic acid (MCPA). In certain embodiments, a herbicidally effective amount of 2,4-D, 2,4-DB, and/or MCPA used is between about 2 g/ha (grams/hectare) to about 5000 g/ha, including about 50 g/ha to about 2500 g/ha, about 60 g/ha to about 2000 g/ha, about 100 g/ha to about 2000 g/ha, about 75 g/ha to about 1000 g/ha, about 100 g/ha to about 500 g/ha, and from about 100 g/ha to about 280 g/ha. In certain embodiments dicamba is used as the herbicide. In certain embodiments, an herbicidally effective amount of dicamba used may be from about 2.5 g/ha to about 10,080 g/ha, including about 2.5 g/ha to about 5,040 g/ha, about 5 g/ha to about 2,020 g/ha, about 10 g/a to about 820 g/h and about 50 g/ha to about 1,000 g/ha, about 100 g/ha to about 800 g/ha and about 250 g/ha to about 800 g/ha.

In accordance with the invention, methods and compositions for the control of weeds are provided comprising the use of plants exhibiting tolerance to glyphosate and auxin-like herbicides such as dicamba. The combination of dicamba and glyphosate allows use of decreased herbicide quantities to achieve the same level of control of glyphosate-tolerant weeds. This provides a significant advance for the control of herbicide tolerance in commercial production fields. In one embodiment, a tank mix of glyphosate and dicamba is applied pre- and/or post-emergence to plants. Glyphosate and dicamba may additionally be applied separately. In order to achieve the same level of weed control using a reduced amount of herbicide relative to individual applications of either or both herbicides, the glyphosate and dicamba are preferably applied within a sufficient interval that both herbicides remain active and able to control weed growth.

The combined use of lower amounts of herbicide to achieve the same degree of weed control as an application of only one of the herbicides is therefore contemplated. For example, the invention provides methods of weed control comprising applying in a field planted with transgenic plants having tolerance to dicamba and glyphosate a herbicide composition comprising less than a 1× rate of glyphosate and/or dicamba, relative to the standard manufacturer labeled rate. Examples of respective glyphosate and dicamba application rates include from about a 0.5×-0.95× of either herbicide, specifically including about 0.5×, 0.6×, 0.7×, 0.8×. 0.85×, 0.9×, and 0.95× of either herbicide and all derivable combinations thereof, as well as higher rates such as 0.97× and 0.99×. Alternatively, in the case of more difficult to control weeds or where a greater degree of weed control is desired, 1× and higher application rates may be made in view of the finding herein that even high application rates of dicamba did not significantly damage plants. The 1× application rates are set by the manufacturer of a commercially available herbicide formulation and are known to those of skill in the art. For example, the label for Fallow Master™, a glyphosate and dicamba mixture having a ratio of glyphosate:dicamba of about 2:1 recommends application rates of about 451 g/ha (311 ae g/ha glyphosate:140 ae g/ha dicamba) to 621 ae g/ha (428 ae g/ha glyphosate: 193 ae g/ha dicamba) depending upon the weed species and weed height. Combining glyphosate and dicamba allows decreased herbicide use to achieve the same level of weed control as shown below. The spectrum of weeds that may be controlled at any given herbicide application rate may therefore be increased when the herbicides are combined.

Transgenic plants having herbicide tolerance may be made as described in the art. Dicamba tolerance may be conferred, for example, by a gene for dicamba monooxygenase (DMO) from *Pseudomonas maltophilia* (e.g. U.S. Patent Application No: 20030135879). Examples of sequences that may be used in this regard are also found in U.S. Patent Application 60/811,276, incorporated by reference herein in its entirety. Additional auxin-like herbicide-degrading activities are also known, including a dehalogenase activity (Wang, 1996).

Unmodified and modified protein molecules and their corresponding nucleic acid molecules providing herbicide tolerances to one or more of these herbicides are well known in the art. They are exemplified below and are incorporated herein by reference:

a) sequences encoding tolerance to glyphosate include 5-enolpyruvylshikimate-3-phosphate synthases (EPSPS; U.S. Pat. No. 5,627,061, U.S. Pat. No. RE39,247, U.S. Pat. No. 6,040,497, U.S. Pat. No. 5,094,945, WO04074443, and WO04009761), glyphosate oxidoreductase (GOX; U.S. Pat. No. 5,463,175), glyphosate decarboxylase (WO05003362 and U.S. Patent Application 20040177399), and glyphosate-N-acetyl transferase (GAT; e.g. U.S. Patent publications 20030083480 and 20070079393) conferring tolerance to glyphosate;

b) dicamba monooxygenase (DMO, encoded by ddmC) conferring tolerance to auxin-like herbicides such as dicamba (U.S. Patent Applications 20030115626, 20030135879; Wang et al., 1996; Herman et al., 2005);

c) phosphinothricin acetyltransferase (bar) conferring tolerance to phosphinothricin or glufosinate (U.S. Pat. No. 5,646,024, U.S. Pat. No. 5,561,236, EP 275,957; U.S. Pat. No. 5,276,268; U.S. Pat. No. 5,637,489; U.S. Pat. No. 5,273,894);

d) 2,2-dichloropropionic acid dehalogenase conferring tolerance to 2,2-dichloropropionic acid (Dalapon) (WO9927116);

e) acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. No. 6,225,105; U.S. Pat. No. 5,767,366, U.S. Pat. No. 4,761,373; U.S. Pat. No. 5,633,437; U.S. Pat. No. 6,613,963; U.S. Pat. No. 5,013,659; U.S. Pat. No. 5,141,870; U.S. Pat. No. 5,378,824; U.S. Pat. No. 5,605,011);

f) haloarylnitrilase (Bxn) for conferring tolerance to bromoxynil (WO8704181A1; U.S. Pat. No. 4,810,648; WO8900193A);

g) modified acetyl-coenzyme A carboxylase for conferring tolerance to cyclohexanedione (sethoxydim) and aryloxyphenoxypropionate (haloxyfop) (U.S. Pat. No. 6,414,222);

h) dihydropteroate synthase (sulI) for conferring tolerance to sulfonamide herbicides (U.S. Pat. No. 5,597,717; U.S. Pat. No. 5,633,444; U.S. Pat. No. 5,719,046);

i) 32 kD photosystem II polypeptide (psbA) for conferring tolerance to triazine herbicides (Hirschberg et al., 1983);

j) anthranilate synthase for conferring tolerance to 5-methyltryptophan (U.S. Pat. No. 4,581,847);

k) dihydrodipicolinic acid synthase (dapA) for conferring to tolerance to aminoethyl cysteine (WO8911789);

l) phytoene desaturase (crtI) for conferring tolerance to pyridazinone herbicides such as norflurazon (JP06343473);

m) hydroxy-phenyl pyruvate dioxygenase for conferring tolerance to cyclopropylisoxazole herbicides such as isoxaflutole (WO 9638567; U.S. Pat. No. 6,268,549);

n) modified protoporphyrinogen oxidase I (protox) for conferring tolerance to protoporphyrinogen oxidase inhibitors (U.S. Pat. No. 5,939,602); and o) aryloxyalkanoate dioxygenase (AAD-1, AAD-12) for conferring tolerance to an herbicide containing an aryloxyalkanoate moiety (WO05107437; WO07053482). Examples of such herbicides include phenoxy auxins (such as 2,4-D and dichlorprop), pyridyloxy auxins (such as fluoroxypyr and triclopyr), aryloxyphenoxypropionates (AOPP) acetyl-coenzyme A carboxylase (ACCase) inhibitors (such as haloxyfop, quizalofop, and diclofop), and 5-substituted phenoxyacetate protoporphyrinogen oxidase IX inhibitors (such as pyraflufen and flumiclorac).

Variants of DMOs having a capability to degrade auxin-like herbicides, as well as glyphosate or other herbicide tolerance genes, can readily be prepared and assayed for activity according to standard methods. Such sequences can also be identified by techniques known in the art such as nucleic acid hybridization, for example, from suitable organisms including bacteria that degrade auxin-like herbicides such as dicamba or other herbicides (U.S. Pat. No. 5,445,962; Cork and Krueger, 1991; Cork and Khalil, 1995). Variants can also be chemically synthesized, for example, using the known DMO polynucleotide sequences according to techniques well known in the art. For instance, DNA sequences may be synthesized by phosphoamidite chemistry in an automated DNA synthesizer. Chemical synthesis may be desirable because codons preferred by the host in which the DNA sequence will be expressed may be used to optimize expression.

Modification and changes may be made to the polypeptide sequence of a protein such as the DMO sequences provided herein while retaining enzymatic activity. The following is a discussion based upon changing the amino acids of a protein to create an equivalent, or even an improved, modified polypeptide and corresponding coding sequences. It is known, for example, that certain amino acids may be substituted for other amino acids in a protein structure without appreciable loss of interactive binding capacity with structures such as binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the DMO peptide sequences described herein or other herbicide tolerance polypeptides and corresponding DNA coding sequences without appreciable loss of their biological utility or activity.

In making such changes, the hydropathic index of amino acids may be considered. The importance of the hydropathic amino acid index in conferring interactive biologic function on a protein is generally understood in the art (Kyte et al., 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It is known in the art that amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. It is understood that an amino acid can be substituted for another having a similar hydrophilicity value and still obtain a biologically equivalent protein. In such changes, the substitution of amino acids whose hydrophilicity values are within ±2 is preferred, those which are within ±1 are particularly preferred, and those within ±0.5 are even more particularly preferred. Exemplary substitutions which take these and various of the foregoing characteristics into consideration are well known to those of skill in the art and include: arginine and lysine; glutamate and aspartate; serine and threonine; glutamine and asparagine; and valine, leucine and isoleucine.

A gene conferring herbicide tolerance will typically be linked to a plant promoter driving expression of the gene in an amount sufficient to confer the herbicide tolerance. Promoters suitable for this and other uses are well known in the art. Examples describing such promoters include U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,388,170 (bidirectional promoters), U.S. Pat. No. 6,635,806 (gamma-coixin promoter), and U.S. patent application Ser. No. 09/757,089 (maize chloroplast aldolase promoter). Additional promoters that may find use are a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., 1987), the CaMV 35S promoter (Odell et al., 1985), the figwort mosaic virus 35S-promoter (Walker et al., 1987), the sucrose synthase promoter (Yang et al., 1990), the R gene complex promoter (Chandler et al., 1989), the chlorophyll a/b binding protein gene promoter, CaMV35S (U.S. Pat. Nos. 5,322,938; 5,352,605; 5,359,142; and 5,530,196), FMV35S (U.S. Pat. Nos. 6,051,753; 5,378,619), a PClSV promoter (e.g. U.S. Pat. No. 5,850,019, and the promoter of SEQ ID NO:15), the SCP1 promoter (U.S. Pat. No. 6,677,503); and AGRtu.nos (GenBank Accession V00087; Depicker et al, 1982; Bevan et al., 1983) promoters, and the like.

Benefit may be obtained for the expression of herbicide tolerance genes by use of a sequence coding for a transit peptide. For example, incorporation of a suitable chloroplast transit peptide, such as, the *Arabidopsis thaliana* EPSPS CTP (Klee et al., 1987), and the *Petunia hybrida* EPSPS CTP (della-Cioppa et al., 1986) has been shown to target heterologous EPSPS protein sequences to chloroplasts in transgenic plants. DMO may also be targeted to chloroplasts. Chloroplast transit peptides (CTPs) are engineered to be fused to the N-terminus of a protein to direct the protein into the plant chloroplast. Such sequences may find use in connection with a nucleic acid conferring dicamba tolerance in particular. Many chloroplast-localized proteins are expressed from nuclear genes as precursors and are targeted to the chloroplast by a chloroplast transit peptide that is removed during the import process. Examples of chloroplast proteins include the small subunit (RbcS2) of ribulose-1,5,-bisphosphate carboxylase such as from pea (*Pisum sativum*), ferredoxin, ferredoxin oxidoreductase, the light-harvesting complex protein I and protein II, and thioredoxin F. Other exemplary chloroplast targeting sequences include the maize cab-m7 signal sequence (Becker et al., 1992; PCT WO 97/41228), the pea glutathione reductase signal sequence (Creissen et al., 1995;

PCT WO 97/41228), and the CTP of the *Nicotiana tobaccum* ribulose 1,5-bisphosphate carboxylase small subunit chloroplast transit peptide (SSU-CTP) (Mazur, et al., 1985). Use of AtRbcS4 (CTP1; U.S. Pat. No. 5,728,925), AtShkG (CTP2; Klee et al., 1987), AtShkGZm (CTP2synthetic; see SEQ ID NO:14 of WO04009761), PsRbcS (Coruzzi et al., 1984), and those disclosed in U.S. Provisional Appln. Ser. No. 60/891, 675 with the invention in particular may be of benefit, for instance with regard to expression of a DMO polypeptide (e.g. see SEQ ID NOs:3-14 for peptide sequences of CTPs and the nucleic acid sequences that encode them).

A 5' UTR that functions as a translation leader sequence is a DNA genetic element located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences include maize and petunia heat shock protein leaders (U.S. Pat. No. 5,362,865), plant virus coat protein leaders, plant rubisco leaders, among others (Turner and Foster, 1995). Non-limiting examples of 5' UTRs that may in particular be of benefit for use GmHsp (U.S. Pat. No. 5,659,122), PhDnaK (U.S. Pat. No. 5,362,865), AtAnt1, TEV (Carrington and Freed, 1990), and AGRtunos (GenBank Accession V00087; Bevan et al., 1983).

The 3' non-translated sequence, 3' transcription termination region, or poly adenylation region means a DNA molecule linked to and located downstream of a structural polynucleotide molecule and includes polynucleotides that provide polyadenylation signal and other regulatory signals capable of affecting transcription, mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA genes. An example of a 3' transcription termination region is the nopaline synthase 3' region (nos 3'; Fraley et al., 1983). The use of different 3' nontranslated regions is exemplified (Ingelbrecht et al., 1989). Polyadenylation molecules from a *Pisum sativum* RbcS2 gene (Ps.RbcS2-E9; Coruzzi et al., 1984) and AGRtu.nos (Genbank Accession E01312) in particular may be of benefit for use with the invention.

Any of the techniques known in the art for introduction of transgenes into plants may be used to prepare a herbicide tolerant plant in accordance with the invention (see, for example, Miki et al., 1993). Suitable methods for transformation of plants are believed to include virtually any method by which DNA can be introduced into a cell, such as by electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,635,055; 5,824,877; 5,591,616; 5,981,840; and 6,384,301; and protoplast transformation as illustrated in U.S. Pat. No. 5,508,184, etc. Through the application of techniques such as these, the cells of virtually any plant species may be stably transformed, and these cells developed into transgenic plants. Techniques that may be particularly useful in the context of cotton transformation are disclosed in U.S. Pat. Nos. 5,846,797, 5,159,135, 5,004,863, and 6,624,344; and techniques for transforming *Brassica* plants in particular are disclosed, for example, in U.S. Pat. No. 5,750,871; and techniques for transforming soybean are disclosed in for example in Zhang et al., 1999 and U.S. Pat. No. 6,384,301). Techniques for transforming corn are disclosed, for example, in U.S. Pat. No. 7,060,876, U.S. Pat. No. 5,591,616, and WO9506722.

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

Cells that survive the exposure to the selective agent, or cells that have been scored positive in a screening assay, may be cultured in media that supports regeneration of plants. In an exemplary embodiment, any suitable plant tissue culture media, for example, MS and N6 media may be modified by including further substances such as growth regulators. Tissue may be maintained on a basic media with growth regulators until sufficient tissue is available to begin plant regeneration efforts, or following repeated rounds of manual selection, until the morphology of the tissue is suitable for regeneration, typically at least 2 weeks, then transferred to media conducive to shoot formation. Cultures are transferred periodically until sufficient shoot formation has occurred. Once shoot are formed, they are transferred to media conducive to root formation. Once sufficient roots are formed, plants can be transferred to soil for further growth and maturity.

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

Once a transgene has been introduced into a plant, that gene can be introduced into any plant sexually compatible with the first plant by crossing, without the need for ever directly transforming the second plant. Therefore, as used herein the term "progeny" denotes the offspring of any generation of a parent plant prepared in accordance with the instant invention, wherein the progeny comprises a selected DNA construct prepared in accordance with the invention. A "transgenic plant" may thus be of any generation. "Crossing" a plant to provide a plant line having one or more added transgenes or alleles relative to a starting plant line, as disclosed herein, is defined as the techniques that result in a particular sequence being introduced into a plant line by crossing a starting line with a donor plant line that comprises a transgene or allele of the invention. To achieve this one could, for example, perform the following steps: (a) plant seeds of the first (starting line) and second (donor plant line that comprises a desired transgene or allele) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower.

The crop may be a dicot crop selected from the group consisting of alfalfa, beans, broccoli, cabbage, carrot, cauliflower, celery, Chinese cabbage, cotton, cucumber, eggplant, lettuce, melon, pea, pepper, peanut, potato, pumpkin, radish, rapeseed, spinach, soybean, squash, sugarbeet, sunflower, tomato, and watermelon. Preferably, the crop is a soybean or cotton crop.

The crop may be a monocot crop selected from the group consisting of corn, onion, rice, sorghum, wheat, rye, millet, sugarcane, oat, triticale, switchgrass, and turfgrass. Preferably, the crop is corn.

Nucleic acid molecules providing tolerance to glyphosate, glufosinate, dicamba, and 2,4-D are disclosed above. These nucleic acid molecules are introduced in soybean or cotton by transformation methods as disclosed above.

Equipment and methods known in the art are used to apply various herbicide treatments as disclosed herein. The application rates of herbicides maybe varied, for instance as described above, depending upon the soil texture, pH, organic matter content, tillage systems, and the size of the weed, and can be determined by consulting the herbicide label for the proper herbicide rate.

The preparation of herbicide compositions for use in connection with the current invention will be apparent to those of skill in the art in view of the disclosure. Such compositions, which are commercially available, will typically include, in addition to the active ingredient, components such as surfactants, solid or liquid carriers, solvents and binders. Examples of surfactants that may be used for application to plants include the alkali metal, alkaline earth metal or ammonium salts of aromatic sulfonic acids, e.g., ligno-, phenol-, naphthalene- and dibutylnaphthalenesulfonic acid, and of fatty acids of arylsulfonates, of alkyl ethers, of lauryl ethers, of fatty alcohol sulfates and of fatty alcohol glycol ether sulfates, condensates of sulfonated naphthalene and its derivatives with formaldehyde, condensates of naphthalene or of the naphthalenesulfonic acids with phenol and formaldehyde, condensates of phenol or phenolsulfonic acid with formaldehyde, condensates of phenol with formaldehyde and sodium sulfite, polyoxyethylene octylphenyl ether, ethoxylated isooctyl-, octyl- or nonylphenol, tributylphenyl polyglycol ether, alkylaryl polyether alcohols, isotridecyl alcohol, ethoxylated castor oil, ethoxylated triarylphenols, salts of phosphated triarylphenolethoxylates, lauryl alcohol polyglycol ether acetate, sorbitol esters, lignin-sulfite waste liquors or methylcellulose, or mixtures of these. Common practice in the case of surfactant use is about 0.25% to 1.0% by weight, and more commonly about 0.25% to 0.5% by weight.

Compositions for application to plants may be solid or liquid. Where solid compositions are used, it may be desired to include one or more carrier materials with the active compound. Examples of carriers include mineral earths such as silicas, silica gels, silicates, talc, kaolin, attaclay, limestone, chalk, loess, clay, dolomite, diatomaceous earth, calcium sulfate, magnesium sulfate, magnesium oxide, ground synthetic materials, fertilizers such as ammonium sulfate, ammonium phosphate, ammonium nitrate, thiourea and urea, products of vegetable origin such as cereal meals, tree bark meal, wood meal and nutshell meal, cellulose powders, attapulgites, montmorillonites, mica, vermiculites, synthetic silicas and synthetic calcium silicates, or mixtures of these. Solid formulations may be formulated as dusts, dispersible powders, granules, microcapsules and the like. Liquid formulations may include aqueous and non-aqueous solutions, emulsions, and the like.

For liquid solutions, water-soluble compounds or salts may be included, such as sodium sulfate, potassium sulfate, sodium chloride, potassium chloride, sodium acetate, ammonium hydrogen sulfate, ammonium chloride, ammonium acetate, ammonium formate, ammonium oxalate, ammonium carbonate, ammonium hydrogen carbonate, ammonium thiosulfate, ammonium hydrogen diphosphate, ammonium dihydrogen monophosphate, ammonium sodium hydrogen phosphate, ammonium thiocyanate, ammonium sulfamate or ammonium carbamate.

Other exemplary components in herbicidal compositions include binders such as polyvinylpyrrolidone, polyvinyl alcohol, partially hydrolyzed polyvinyl acetate, carboxymethylcellulose, starch, vinylpyrrolidone/vinyl acetate copolymers and polyvinyl acetate, or mixtures of these; lubricants such as magnesium stearate, sodium stearate, talc or polyethylene glycol, or mixtures of these; antifoams such as silicone emulsions, long-chain alcohols, phosphoric esters, acetylene diols, fatty acids or organofluorine compounds, and complexing agents such as: salts of ethylenediaminetetraacetic acid (EDTA), salts of trinitrilotriacetic acid or salts of polyphosphoric acids, or mixtures of these.

Also, disclosed are methods of minimizing development of herbicide resistant weeds in the future by rotating a first cropping system in a first year comprising a crop tolerant to one or more herbicides and accompanying herbicidal treatments with a second cropping system in a second year comprising a crop tolerant to one or more herbicides and accompanying herbicidal treatments, wherein the second crop has tolerance to a different herbicide or a combination of herbicides.

The cropping systems disclosed herein incorporate not only the use of crops that are tolerant to one or more herbicides and the use of chemical weed control means such as types, rates, and timing of herbicide applications but also the use of cultural means such as crop rotation with other transgenic crops having tolerance to one or more herbicides and mechanical weed control means such as tilling, resulting in novel integrated weed management.

A crop tolerant to one or more herbicides belonging to different mode of action groups is produced and utilized in a cropping system of the present invention. These herbicides are approved by Weed Science Society of America (WSSA) and non-limiting examples are found in Table 2 (Mallory-Smith and Retzinger Jr, 2003; Herbicide Handbook, 2002; Schmidt, 1997).

The invention should be read in view of these definitions:

"Auxin-like" herbicides refers to herbicides of four chemical families: phenoxy, carboxylic acid (or pyridine), benzoic acid, and quinaline carboxylic acid. These types of herbicides mimic or act like the natural plant growth regulators called auxins. The action of auxinic herbicides appears to affect cell wall plasticity and nucleic acid metabolism, which can lead to uncontrolled cell division and growth.

Phenoxy herbicides are most common and have been used as herbicides since the 1940s when (2,4-dichlorophenoxy) acetic acid (2,4-D) was discovered. Other examples include 4-(2,4-dichlorophenoxy) butyric acid (2,4-DB), 2-(2,4-dichlorophenoxy) propanoic acid (2,4-DP), (2,4,5-trichlorophenoxy)acetic acid (2,4,5-T), 2-(2,4,5-Trichlorophenoxy) Propionic Acid (2,4,5-TP), 2-(2,4-dichloro-3-methylphenoxy)-N-phenylpropanamide (clomeprop), (4-chloro-2-methylphenoxy)acetic acid (MCPA), 4-(4-chloro-o-tolyloxy) butyric acid (MCPB), and 2-(4-chloro-2-methylphenoxy) propanoic acid (MCPP).

The next largest chemical family is the carboxylic acid herbicides, also called pyridine herbicides. Examples include 3,6-dichloro-2-pyridinecarboxylic acid (Clopyralid), 4-amino-3,5,6-trichloro-2-pyridinecarboxylic acid (picloram), (2,4,5-trichlorophenoxy)acetic acid (triclopyr), and 4-amino-3,5-dichloro-6-fluoro-2-pyridyloxyacetic acid (fluoroxypyr).

Examples of benzoic acids include 3,6-dichloro-o-anisic acid (dicamba), 3,5,6-trichloro-o-anisic acid (tricamba), and 3-amino-2,5-dichlorobenzoic acid (chloramben). Dicamba is a particularly useful herbicide for use in the present invention. A fourth chemical family of auxinic herbicides is the quinaline carboxylic acid family, an example of which is 3,7-dichloro-8-quinolinecarboxylic acid (quinclorac). This herbicide is unique in that it also will control some grass weeds, unlike the other auxin-like herbicides which essentially control only broadleaf or dicotyledonous plants. Another herbicide in this category is 7-chloro-3-methyl-8-quinolinecarboxylic acid (quinmerac).

"Dicamba" refers to 3,6-dichloro-o-anisic acid or 3,6-dichloro-2-methoxy benzoic acid and its acids and salts. Its salts include isopropylamine, diglycoamine, dimethylamine, potassium and sodium. Examples of commercial formulations of dicamba include, without limitation, Banvel™ (as DMA salt), Clarity™ (as DGA salt), VEL-58-CS-11™ and Vanquish™ (as DGA salt, BASF).

A comprehensive list of weeds that are controlled by dicamba can be found at www.greenbook.net/docs/Label/L2281.pdf. The herbicide is particularly useful for control of taller weeds and more difficult to control weeds such as purslane, sicklepod, morninglory and wild buckwheat. Dicamba can be used to control weeds not susceptible to other herbicides. Following the application of Clarity™, a formulation of dicamba, a minimum accumulation of one inch of rainfall or overhead irrigation followed by a 14 day waiting period for the 4 to 8 ounce/acre rates or a 28 day waiting period for the 16 ounce/acre rates has been recommend for controlling weeds in a soybean field (see Table 22 in VanGessel and Majek, 2005). The Clarity® label recommends that it be applied at least 15 days prior to sorghum planting. Similarly, for cotton, a waiting period of 21 days is recommended after applying Clarity® or Banvel® to the field, before planting the cotton seeds (Craig et al., 2005, www.ipmcenters.org/cropprofiles/docs/tncotton.html) and no pre-emergence and post-emergence application are label recommended. For post-emergent weed control in corn, dicamba is the 5th most widely used herbicide for broad leaf weeds. However, although the optimal rate for broad leaf weed control is between 280 to 560 g/h (grams/hectare), the average use rate in corn is 168 g/h as at higher use rates and under certain environmental conditions, dicamba can injure corn. In a cropping system comprising crop plants displaying tolerance to dicamba, more flexibility is available to a grower in the timing and usage rate for dicamba application.

"Glyphosate" refers to N-phosphonomethylglycine and salts thereof. Glyphosate is commercially available in numerous formulations. Examples of these formulations of glyphosate include, without limitation, those sold by Monsanto Company as ROUNDUP®, ROUNDUP® ULTRA, ROUNDUP® ULTRAMAX, ROUNDUP® CT, ROUNDUP® EXTRA, ROUNDUP® BIACTIVE, ROUNDUP® BIOFORCE, RODEO®, POLARIS®, SPARK® and ACCORD® herbicides, all of which contain glyphosate as its isopropylammonium salt, ROUNDUP® WEATHERMAX containing glyphosate as its potassium salt; ROUNDUP® DRY and RIVAL® herbicides, which contain glyphosate as its ammonium salt; ROUNDUP® GEOFORCE, which contains glyphosate as its sodium salt; and TOUCHDOWN® herbicide, which contains glyphosate as its trimethylsulfonium salt.

"First treatment" refers to application of one or more herbicides sequentially or in a tank-mix at pre-planting, planting, pre-emergence, or at a combination of these stages.

"Second treatment" refers to applying one or more herbicides sequentially or in a tank-mix at an early post-emergence stage.

"Third treatment" refers to applying one or more herbicides sequentially or in a tank-mix at a late post-emergence stage. These stages are different for each crop. Generally it refers to development of crop canopy which influences both shading of weed growth and ability to get application equipment through the rows of the crop.

"Fourth treatment" refers to applying one or more herbicides sequentially or in a tank-mix at a pre-harvest stage. Preharvest is generally defined as when crop and weeds are still green and growing to a point where post emergence herbicides can still be effective.

"Fifth treatment" refers to applying one or more herbicides sequentially or in a tank-mix at a post-harvest stage when a crop has been removed. This can either be a treatment in fall or spring, treatment between a fallow period, or treatment between a crop planting in double crop planting situations.

An "herbicide resistant weed" is defined as a weed biotype that is no longer controllable at a herbicide rate that previously used to controlled it, and the trait is passed to offspring (heritable). Non-limiting examples of these weeds are given in Table 1.

"Tough weed" refers to weeds that are difficult to control.

"Volunteer plant" means a herbicide tolerant crop plant that grows from a seed that was left after harvest in or on the soil from the previous growing season.

"Cropping system" refers to an interactive combination of a crop, any herbicide tolerance exhibited by it, and accompanying herbicidal treatment options available at different stages of crop development, yielding a productive crop.

"Transgenic" cells and organisms include cells and organisms that do not normally degrade a herbicide, such as dicamba, but which have been transformed so that they are able to degrade this herbicide and exhibit agronomically useful levels of tolerance to the application of the herbicide.

TABLE 1

Herbicide tolerant weeds. Classification as per WSSA or HRAC; see Table 2.

ACCase inhibitors resistant weeds (Group 1 or A)

*Alopecurus myosuroides, Avena fatua, Avena sterilis, Avena sterilis ludoviciana, Brachiaria plantaginea, Bromus diandrus, Bromus rigidus, Cynosurus echinatus, Digitaria ciliaris, Digitaria ischaemum, Digitaria sanguinalis, Echinochloa colona, Echinochloa crus-galli, Echinochloa oryzicola, Echinochloa phyllopogon, Eleusine indica, Eriochloa punctata, Hordeum glaucum, Hordeum leporinum, Ischaemum rugosum, Leptochloa chinensis, Lolium multiflorum, Lolium perenne, Lolium persicum, Lolium rigidum, Phalaris minor, Phalaris paradoxa, Rottboellia exalta, Setaria faberi, Setaria viridis, Setaria viridis* var. *robusta-alba Schreiber, Setaria viridis* var. *robusta-purpurea, Snowdenia polystachea, Sorghum halepense, Sorghum Sudanese*

TABLE 1-continued

Herbicide tolerant weeds. Classification as per WSSA or HRAC; see Table 2.

ALS inhibitors resistant weeds (Group 2 or B)

*Alisma plantago-aquatica, Alopecurus myosuroides, Amaranthus blitoides, Amaranthus hybridus, Amaranthus lividus, Amaranthus palmeri, Amaranthus powellii, Amaranthus quitensis, Amaranthus retroflexus, Amaranthus rudis, Amaranthus tuberculatus, Ambrosia artemisiifolia, Ambrosia trifida, Ammania auriculata, Ammania coccinea, Anthemis cotula, Apera spica-venti, Avena fatua, Avena sterilis ludoviciana, Bacopa rotundifolia, Bidens pilosa, Bidens subalternans, Brassica tournefortii, Bromus tectorum, Camelina microcarpa, Chenopodium album, Chrysanthemum coronarium, Conyza bonariensis, Conyza Canadensis, Cuscuta campestris, Cyperus difformis, Damasonium minus, Descurainia Sophia, Digitaria sanguinalis, Diplotaxis tenuifolia, Echinochloa colona, Echinochloa crus-galli, Echium plantagineum, Elatine triandra* var. *pedicellata, Eleusine indica, Euphorbia heterophylla, Fallopia convolvulus, Fimbristylis miliacea, Galeopsis tetrahit, Galium spurium, Helianthus annuus, Hordeum glaucum, Iva xanthifolia, Ixophorus unisetus, Kochia scoparia, Lactuca serriola, Limnocharis flava, Limnophila erecta, Limnophila sessiliflora, Lindernia dubia, Lindernia dubia* var. *major, Lindernia micrantha, Lindernia procumbens, Lolium multiflorum, Lolium perenne, Lolium rigidum, Mesembryanthemum crystallinum, Monochoria korsakowii, Monochoria vaginalis, Neslia paniculata, Papaver rhoeas, Parthenium hysterophorus, Pentzia suffruticosa, Phalaris minor, Raphanus raphanistrum, Raphanus sativus, Rapistrum rugosum, Rotala indica* var. *uliginosa, Sagittaria guyanensis, Sagittaria montevidensis, Sagittaria pygmaea, Salsola iberica, Scirpus juncoides* var. *ohwianus, Scirpus mucronatus, Setaria faberi, Setaria lutescens, Setaria viridis, Setaria viridis* var. *robusta-alba Schreiber, Sida spinosa, Sinapis arvensis, Sisymbrium orientale, Sisymbrium thellungii, Solanum ptycanthum, Sonchus asper, Sonchus oleraceus, Sorghum bicolor, Sorghum halepense, Stellaria media, Thlaspi arvense, Xanthium strumarium*

Arylaminopropionic acids resistant weeds (Group 25 or Z (unclassified))

*Avena fatua, Avena sterilis ludoviciana*

Bipyridiliums resistant weeds (Group 22 or D)

*Amaranthus lividus, Arctotheca calendula, Bidens pilosa, Conyza bonariensis, Conyza Canadensis, Conyza sumatrensis, Crassocephalum crepidiodes, Cuphea carthagenenis, Eleusine indica, Epilobium adenocaulon, Erigeron philadelphicus, Hordeum glaucum, Hordeum leporinum, Ischaemum rugosum, Landoltia punctata, Lepidium virginicum, Lolium rigidum, Monochoria korsakowii, Poa annua, Solanum americanum, Solanum nigrum, Vulpia bromoides, Youngia japonica*

Carotenoid biosynthesis inhibitors resistant weeds (Group 12 or F1)

*Hydrilla verticillata, Raphanus raphanistrum*

Cellulose inhibitors resistant weeds (Group 20 & 21 or L)

*Echinochloa erecta*

Chloroacetamides and others resistant weeds (Group 15 or K3)

*Echinochloa crus-galli, Lolium rigidum*

Dinitroanilines and others resistant weeds (Group 3 or K1)

*Alopecurus myosuroides, Amaranthus palmeri, Avena fatua, Echinochloa crus-galli, Eleusine indica, Fumaria densiflora, Lolium rigidum, Poa annua, Setaria viridis, Sorghum halepense*

Glycines resistant weeds (Group 9 or G)

*Amaranthus palmeri, Ambrosia artemisiifolia, Conyza bonariensis, Conyza Canadensis, Eleusine indica, Lolium multiflorum, Lolium rigidum, Plantago lanceolata*

Mitosis inhibitors resistant weeds (Group 23 or K2)

*Lolium rigidum*

Nitriles and others resistant weeds (Group 6 or C3)

*Senecio vulgaris*

Organoarsenical resistant weeds (Group 17 or Z (unclassified))

*Xanthium strumarium*

Photosystem II inhibitors resistant weeds (Group 5 or C1 (atrazine type))

*Abutilon theophrasti, Alopecurus myosuroides, Amaranthus albus, Amaranthus blitoides, Amaranthus cruentus, Amaranthus hybridus, Amaranthus lividus, Amaranthus palmeri, Amaranthus powellii, Amaranthus retroflexus, Amaranthus rudis, Ambrosia artemisiifolia, Arenaria serpyllifolia, Atriplex patula, Bidens tripartite, Brachypodium distachyon, Brassica campestris, Bromus tectorum, Capsella bursa-pastoris, Chamomilla suaveolens, Chenopodium album, Chenopodium ficifolium, Chenopodium hybridum, Chenopodium polyspermum, Chenopodium strictum* var. *Glaucophyllum, Chloris inflate, Conyza bonariensis, Conyza Canadensis, Crypsis schoenoides, Datura stramonium, Digitaria sanguinalis, Echinochloa crus-galli, Epilobium adenocaulon, Epilobium tetragonum, Fallopia convolvulus, Galinsoga ciliate, Kochia scoparia, Lolium rigidum, Lophochloa smyrnacea, Matricaria matricarioides, Panicum capillare, Panicum dichotomiflorum, Phalaris paradoxa, Plantago lagopus, Poa annua, Polygonum aviculare, Polygonum hydropiper, Polygonum lapathifolium, Polygonum pensylvanicum, Polygonum persicaria, Polypogon monspeliensis, Portulaca oleracea, Raphanus raphanistrum, Senecio vulgaris,*

TABLE 1-continued

Herbicide tolerant weeds. Classification as per WSSA or HRAC; see Table 2.

*Setaria faberi, Setaria glauca, Setaria verticillata, Setaria viridis, Setaria viridis* var. *Major, Sinapis arvensis, Solanum nigrum, Sonchus asper, Stellaria media, Urochloa panicoides, Urtica urens*
PPO inhibitors resistant weeds (Group 14 or E)

*Amaranthus rudis, Ambrosia artemisiifolia, Euphorbia heterophylla*
Pyrazoliums resistant weeds (Group Z (unclassified))

*Avena fatua*
Synthetic auxins/Auxin-like herbicides resistant weeds (Group 4 or O)

*Carduus nutans, Carduus pycnocephalus, Centaurea solstitialis, Cirsium arvense, Commelina diffusa, Convulvulus arvensis, Daucus carota, Digitaria ischaemum, Echinochloa colona, Echinochloa crus-galli, Echinochloa crus-pavonis, Fimbristylis miliacea, Galeopsis tetrahit, Galium spurium, Kochia scoparia, Limnocharis flava, Limnophila erecta, Matricaria perforate, Papaver rhoeas, Ranunculus acris, Sinapis arvensis, Soliva sessilis, Sphenoclea zeylanica, Stellaria media*
Thiocarbamates and others resistant weeds (Group 8 or N)

*Avena fatua, Echinochloa crus-galli, Echinochloa oryzicola, Echinochloa phyllopogon, Lolium rigidum, Nassella trichotoma, Poa annua, Stipa neesiana*
Triazoles, ureas, isoxazolidiones resistant weeds (Group 11 or F3)

*Agrostis stolonifera, Lolium rigidum, Poa annua, Polygonum aviculare*
Ureas and amides resistant weeds (Group 7 or C2)

*Alopecurus japonicus, Alopecurus myosuroides, Amaranthus powellii, Amaranthus retroflexus, Ambrosia artemisiifolia, Apera spica-venti, Beckmannia syzigachne, Bromus tectorum, Chenopodium album, Chloris inflate, Conyza canadensis, Echinochloa colona, Echinochloa crus-galli, Echinochloa erecta, Euphorbia heterophylla, Lolium multiflorum, Lolium rigidum, Phalaris minor, Poa annua, Portulaca oleracea, Senecio vulgaris*

TABLE 2

Herbicides classified by primary site of action

| HRAC Group | Mode of Action | Chemical Family | Active Ingredient | WSSA Group |
|---|---|---|---|---|
| A | Inhibition of acetyl CoA carboxylase (ACCase) | Aryloxyphenoxy-propionates 'FOPs' | clodinafop-propargyl cyhalofop-butyl diclofop-methyl fenoxaprop-P-ethyl fluazifop-P-butyl haloxyfop-R-methyl propaquizafop quizalofop-P-ethyl | 1 |
| | | Cyclohexanediones 'DIMs' | alloxydim butroxydim (clefoxydim proposed) clethodim cycloxydim sethoxydim tepraloxydim tralkoxydim | |
| B | Inhibition of acetolactate synthase ALS (acetohydroxyacid synthase AHAS) | Sulfonylureas | amidosulfuron azimsulfuron bensulfuron-methyl chlorimuron-ethyl chlorsulfuron cinosulfuron cyclosulfamuron ethametsulfuron-methyl ethoxysulfuron flazasulfuron flupyrsulfuron-methyl-Na foramsulfuron halosulfuron-methyl imazosulfuron iodosulfuron metsulfuron-methyl nicosulfuron oxasulfuron primisulfuron-methyl prosulfuron pyrazosulfuron-ethyl | 2 |

TABLE 2-continued

Herbicides classified by primary site of action

| HRAC Group | Mode of Action | Chemical Family | Active Ingredient | WSSA Group |
|---|---|---|---|---|
| | | | rimsulfuron | |
| | | | sulfometuron-methyl | |
| | | | sulfosulfuron | |
| | | | thifensulfuron-methyl | |
| | | | triasulfuron | |
| | | | tribenuron-methyl | |
| | | | trifloxysulfuron | |
| | | | triflusulfuron-methyl | |
| | | | tritosulfuron | |
| | | Imidazolinones | imazapic | |
| | | | imazamethabenz-methyl | |
| | | | imazamox | |
| | | | imazapyr | |
| | | | imazaquin | |
| | | | imazethapyr | |
| | | Triazolopyrimidines | cloransulam-methyl | |
| | | | diclosulam | |
| | | | florasulam | |
| | | | flumetsulam | |
| | | | metosulam | |
| | | Pyrimidinyl(thio)benzoates | bispyribac-Na | |
| | | | pyribenzoxim | |
| | | | pyriftalid | |
| | | | pyrithiobac-Na | |
| | | | pyriminobac-methyl | |
| | | Sulfonylaminocarbonyl-triazolinones | flucarbazone-Na | |
| | | | procarbazone-Na | |
| C1 | Inhibition of photosynthesis at photosystem II | Triazines | ametryne | 5 |
| | | | atrazine | |
| | | | cyanazine | |
| | | | desmetryne | |
| | | | dimethametryne | |
| | | | prometon | |
| | | | prometryne | |
| | | | propazine | |
| | | | simazine | |
| | | | simetryne | |
| | | | terbumeton | |
| | | | terbuthylazine | |
| | | | terbutryne | |
| | | | trietazine | |
| | | Triazinones | hexazinone | |
| | | | metamitron | |
| | | | metribuzin | |
| | | Triazolinone | amicarbazone | |
| | | Uracils | bromacil | |
| | | | lenacil | |
| | | | terbacil | |
| | | Pyridazinones | pyrazon = chloridazon | |
| | | Phenyl-carbamates | desmedipham | |
| | | | phenmedipham | |
| C2 | Inhibition of photosynthesis at photosystem II | Ureas | chlorobromuron | 7 |
| | | | chlorotoluron | |
| | | | chloroxuron | |
| | | | dimefuron | |
| | | | diuron | |
| | | | ethidimuron | |
| | | | fenuron | |
| | | | fluometuron (see F3) | |
| | | | isoproturon | |
| | | | isouron | |
| | | | linuron | |
| | | | methabenzthiazuron | |
| | | | metobromuron | |
| | | | metoxuron | |
| | | | monolinuron | |
| | | | neburon | |
| | | | siduron | |
| | | | tebuthiuron | |
| | | Amides | propanil | |
| | | | pentanochlor | |
| C3 | Inhibition of photosynthesis at photosystem II | Nitriles | bromofenoxim (also M) | 6 |
| | | | bromoxynil (also group M) | |
| | | | ioxynil (also group M) | |

TABLE 2-continued

Herbicides classified by primary site of action

| HRAC Group | Mode of Action | Chemical Family | Active Ingredient | WSSA Group |
|---|---|---|---|---|
| | | Benzothiadiazinone | bentazon | |
| | | Phenyl-pyridazines | pyridate | |
| | | | pyridafol | |
| D | Photosystem-I-electron diversion | Bipyridyliums | diquat | 22 |
| | | | paraquat | |
| E | Inhibition of protoporphyrinogen oxidase (PPO) | Diphenylethers | aciflurofen-Na | 14 |
| | | | bifenox | |
| | | | chlomethoxyfen | |
| | | | fluoroglycofen-ethyl | |
| | | | fomesafen | |
| | | | halosafen | |
| | | | lactofen | |
| | | | oxyfluorfen | |
| | | Phenylpyrazoles | fluazolate | |
| | | | pyraflufen-ethyl | |
| | | N-phenylphthalimides | cinidon-ethyl | |
| | | | flumioxazin | |
| | | | flumiclorac-pentyl | |
| | | Thiadiazoles | fluthiacet-methyl | |
| | | | thidiazimin | |
| | | Oxadiazoles | oxadiazon | |
| | | | oxadiargyl | |
| | | Triazolinones | azafenidin | |
| | | | carfentrazone-ethyl | |
| | | | sulfentrazone | |
| | | Oxazolidinediones | pentoxazone | |
| | | Pyrimidindiones | benzfendizone | |
| | | | butafenacil | |
| | | Others | pyrazogyl | |
| | | | profluazol | |
| F1 | Bleaching: Inhibition of carotenoid biosynthesis at the phytoene desaturase step (PDS) | Pyridazinones | norflurazon | 12 |
| | | Pyridinecarboxamides | diflufenican | |
| | | | picolinafen | |
| | | Others | beflubutamid | |
| | | | fluridone | |
| | | | flurochloridone | |
| | | | flurtamone | |
| F2 | Bleaching: Inhibition of 4-hydroxyphenyl-pyruvate-dioxygenase (4-HPPD) | Triketones | mesotrione | 28 |
| | | | sulcotrione | |
| | | Isoxazoles | isoxachlortole | |
| | | | isoxaflutole | |
| | | Pyrazoles | benzofenap | |
| | | | pyrazolynate | |
| | | | pyrazoxyfen | |
| | | Others | benzobicyclon | |
| F3 | Bleaching: Inhibition of carotenoid biosynthesis (unknown target) | Triazoles | amitrole (in vivo inhibition of lycopene cyclase) | 11 |
| | | Isoxazolidinones | clomazone | 13 |
| | | Ureas | fluometuron (see C2) | |
| | | Diphenylether | aclonifen | |
| G | Inhibition of EPSP synthase | Glycines | glyphosate | 9 |
| | | | sulfosate | |
| H | Inhibition of glutamine synthetase | Phosphinic acids | glufosinate-ammonium | 10 |
| | | | bialaphos = bilanaphos | |
| I | Inhibition of DHP (dihydropteroate) synthase | Carbamates | asulam | 18 |
| K1 | Microtubule assembly inhibition | Dinitroanilines | benefin = benfluralin | 3 |
| | | | butralin | |
| | | | dinitramine | |
| | | | ethalfluralin | |
| | | | oryzalin | |
| | | | pendimethalin | |
| | | | trifluralin | |
| | | Phosphoroamidates | amiprophos-methyl | |
| | | | butamiphos | |
| | | Pyridines | dithiopyr | |
| | | | thiazopyr | |
| | | Benzamides | propyzamide = pronamide | |
| | | | tebutam | |

TABLE 2-continued

Herbicides classified by primary site of action

| HRAC Group | Mode of Action | Chemical Family | Active Ingredient | WSSA Group |
|---|---|---|---|---|
| | | Benzenedicarboxylic acids | DCPA = chlorthal-dimethyl | 3 |
| K2 | Inhibition of mitosis/microtubule organisation | Carbamates | chlorpropham<br>propham<br>carbetamide | 23 |
| K3 | Inhibition of cell division (Inhibition of VLCFAs; see Remarks) | Chloroacetamides | acetochlor<br>alachlor<br>butachlor<br>dimethachlor<br>dimethanamid<br>metazachlor<br>metolachlor<br>pethoxamid<br>pretilachlor<br>propachlor<br>propisochlor<br>thenylchlor | 15 |
| | | Acetamides | diphenamid<br>napropamide<br>naproanilide | |
| | | Oxyacetamides | flufenacet<br>mefenacet | |
| | | Tetrazolinones | fentrazamide | |
| | | Others | anilofos<br>cafenstrole<br>indanofan<br>piperophos | |
| L | Inhibition of cell wall (cellulose) synthesis | Nitriles | dichlobenil<br>chlorthiamid | 20 |
| | | Benzamides | isoxaben | 21 |
| | | Triazolocarboxamides | flupoxam | |
| M | Uncoupling (Membrane disruption) | Dinitrophenols | DNOC<br>dinoseb<br>dinoterb | 24 |
| N | Inhibition of lipid synthesis —not ACCase inhibition | Thiocarbamates | butylate<br>cycloate<br>dimepiperate<br>EPTC<br>esprocarb<br>molinate<br>orbencarb<br>pebulate<br>prosulfocarb<br>thiobencarb = benthiocarb<br>tiocarbazil<br>triallate<br>vernolate | 8 |
| | | Phosphorodithioates | bensulide | |
| | | Benzofuranes | benfuresate<br>ethofumesate | |
| | | Chloro-Carbonic-acids | TCA<br>dalapon<br>flupropanate | 26 |
| O | Synthetic auxins (auxin-like) | Phenoxy-carboxylic-acids | clomeprop<br>2,4-D<br>2,4-DB<br>dichlorprop = 2,4-DP<br>MCPA<br>MCPB<br>mecoprop = MCPP = CMPP | 4 |
| | | Benzoic acids | chloramben<br>dicamba<br>tricamba<br>2,3,6-TBA | |
| | | Pyridine carboxylic acids | clopyralid<br>fluroxypyr<br>picloram<br>triclopyr | |
| | | Quinoline carboxylic acids | quinclorac (also group L)<br>quinmerac | |
| | | Others | benazolin-ethyl | |

TABLE 2-continued

Herbicides classified by primary site of action

| HRAC Group | Mode of Action | Chemical Family | Active Ingredient | WSSA Group |
|---|---|---|---|---|
| P | Inhibition of auxin transport | Phthalamates | naptalam | 19 |
| | | Semicarbazones | diflufenzopyr-Na | |
| R | ... | ... | ... | |
| S | ... | ... | ... | |
| . | ... | ... | ... | |
| Z | Unknown | Arylaminopropionic acids | Flamprop-M-methyl/-isopropyl | 25 |
| | | Pyrazolium | difenzoquat | 8 |
| | | Organoarsenicals | DSMA | 17 |
| | | | MSMA | |
| | | Others | bromobutide | 27 |
| | | | (chloro)-flurenol | |
| | | | cinmethylin | |
| | | | cumyluron | |
| | | | dazomet | |
| | | | dymron = daimuron methyl-dimuron = methyl-dymron | |
| | | | etobenzanid | |
| | | | fosamine | |
| | | | metam | |
| | | | oxaziclomefone | |
| | | | oleic acid | |
| | | | pelargonic acid | |
| | | | pyributicarb | |

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Cropping Systems for Managing Weeds

One embodiment of the present invention is exemplified by Tables 3-5, in which crops tolerant to glyphosate, dicamba, glufosinate, 2,4 D, or a combination thereof (I to X) are utilized with accompanying herbicidal treatments (First to Fifth) at different stages of plant growth and development for managing weeds. For soybean, plant growth stages may be defined as follows: emergence is termed the "VE" growth stage, while early post-emergence soybean stages are often termed "VC" to "V3", and late post-emergence soybean stages are termed "V4" to "R2" (e.g. McWilliams et al., 1999). "Pre-harvest" typically occurs after soybean is physiologically mature, but before harvest, while "post-harvest" occurs after harvest has occurred. "Pre-emergence" application of herbicide therefore refers to an application prior to crop and weed emergence either, before or after planting.

For cotton the timing of growth stages and related herbicide application may be defined as follows:

Pre-Emergence: any time prior to emergence of the crop for the purposes of controlling winter and spring weeds.

Early Post-Emerge: applications that are made from the time the crop emerges through the vegetative growth stage, i.e. until the pin-head square stage.

Late Post-Emerge: Applications that are made during the reproductive stage of cotton growth, i.e. from pin-head square stage until the initiation of boll opening.

Pre-Harvest: Applications made from the initiation of boll opening until just prior to harvest. Most product labels include a prohibition on applying within a certain number of days prior to harvest. For example, Roundup can not be applied within 7 days of harvest. For other products this pre-harvest restriction may be 40 to 70 days.

Post-harvest: Applications made after the harvest for the purpose of controlling late season weeds that may be present at harvest time or emerge prior to the winter season.

One of skill in the art would understand that there are no restrictions on how close applications can be made to crop emergence or crop harvest. However, certain products may have limitations on the label based on crop injury potential (e.g. do not apply with 21 days of planting) or because of chemical residue levels in the seed (e.g. do not apply within 40 days of harvest).

Various herbicide options for each treatment are indicated by letters A, B, C, and so on. Use of these herbicide tolerant crops, their accompanying treatments at various stages of growth results in management of weeds, current herbicide resistant weeds, tough weeds, volunteer plants, and minimizing the development of herbicide resistant weeds in future. Herbicide rates are given in Table 4 and 5 for soybean and cotton, respectively. Exemplary herbicides for use with corn are shown in Table 6. Equipment and methods known in the art are used for applying herbicide treatments.

TABLE 3

Treatments and various options provided for managing weeds in exemplary cropping systems I-XII of the present invention. G-glyphosate, Gl-glufosinate, Pre-a preemergence herbicide, D-dicamba, Di-2,4-D, Post-a postemergent herbicide, P-paraquat. A graminicide is not used with corn unless the corn has tolerance to the class of herbicides used for controlling grasses, such as a fops herbicide.

| Treatment & Timing | Options | glyphosate tolerant I | dicamba tolerant II | glufosinate tolerant III | glyphosate and glufosinate tolerant IV | dicamba and glufosinate tolerant V | 2,4-D tolerant VI | glyphosate and dicamba tolerant VII | dicamba and 2,4-D tolerant VIII | glyphosate, dicamba and glufosinate tolerant IX | glyphosate and 2,4-D tolerant X | glyphosate, dicamba and 2,4-D tolerant XI | glyphosate, dicamba, glufosinate and 2,4-D tolerant XII |
|---|---|---|---|---|---|---|---|---|---|---|---|---|---|
| First (1) Preplant, at plant, pre-emerge or a combination | A | None | None | None | None | None | None | None | None | None | None | None | None |
| | B | Tilling | Tilling | Tilling | Tilling | Tilling | Tilling | Tilling | Tilling | Tilling | Tilling | Tilling | Tilling |
| | C | G | G | G | G | G | G | G | G | G | G | G | G |
| | D | Gl | D | Gl | Gl | D | Di | D | D | D | D | D | D |
| | E | Pre | P | Pre | Pre | P | P | P | P | P | P | P | P |
| | F | P | Gl | P | P | Gl | Gl | Gl | Gl | Gl | Gl | Di | Di |
| | G | G, Gl | Pre | G, Gl | G, Gl | Pre | Pre | Pre | Pre | Pre | Pre | Pre | Pre |
| | H | G, Pre | G, D | G, Pre | G, Pre | G, D | G, P | G, P | P | G, D | G, P | G, D | P |
| | I | G, P | G, P | G, P | G, P | G, P | G, Gl | G, P | G, D | G, P | G, P | G, D | G, D |
| | J | G, Gl, Pre | G, Gl | G, Gl, Pre | G, Gl, Pre | G, Gl | G, Pre | G, Pre | G, Gl | G, Pre | G, Pre | G, Gl | G, Gl |
| | K | G, Gl, P | G, Pre | G, Gl, P | G, Gl, P | G, Pre | G, Di, P | G, Pre | G, Di | G, Pre | G, Pre | G, Di | G, Di |
| | L | G, Gl, Pre, P | G, D, P | G, Gl, Pre, P | G, Gl, Pre, P | G, D, P | | G, D, P | G, Pre | G, D, P | G, Di, P | G, Pre | G, Pre |
| | M | G, Pre, P | G, D, Gl | | G, Pre, P | G, D, Gl | G, Di, Gl | G, D, Gl | G, P | G, D, Gl | G, Di, Gl | G, P | G, P |
| | N | Gl, Pre | G, D, Pre | Gl, Pre | Gl, Pre | G, D, Pre | G, Di, Pre | G, D, Pre | G, D, Di | G, D, Pre | G, Di, Pre | G, D, Di | G, D, Di |
| | O | Gl, P | G, P, Gl | Gl, P | Gl, P | G, P, Gl | G, P, Gl | G, P, Gl | G, D, Pre | G, P, Gl | G, P, Gl | G, D, Pre | G, D, Pre |
| | P | Gl, Pre, P | G, P, Pre | Gl, Pre, P | Gl, Pre, P | G, P, Pre | G, P, Pre | G, P, Pre | G, D, P | G, P, Pre | G, P, Pre | G, D, P | G, D, P |
| | Q | Pre, P | G, Gl, Pre | Pre, P | Pre, P | G, Gl, Pre | G, Gl, Pre | G, Gl, Pre | G, Gl, Pre | G, Gl, Pre | G, Gl, Pre | G, Gl, Di | G, Gl, Di |
| | R | | G, D, P, Gl | | | G, D, P, Gl | G, D, P, Gl | G, D, P, Gl | | G, D, P, Gl | | | |
| | S | | G, D, P, Pre | | | G, D, P, Pre | G, Di, P, Pre | G, D, P, Pre | G, Gl, Pre | G, D, P, Pre | G, Di, P, Pre | G, Gl, Pre | G, Gl, Pre |
| | T | | G, D, Gl, Pre | | | G, D, Gl, Pre | G, Di, Gl, Pre | G, D, Gl, Pre | G, Gl, P | G, D, Gl, Pre | G, Di, Gl, Pre | G, Gl, P | G, Gl, P |
| | U | | G, P, Gl, Pre | | | G, P, Gl, Pre | G, P, Gl, Pre | G, P, Gl, Pre | G, Di, Pre | G, P, Gl, Pre | G, P, Gl, Pre | G, Di, Pre | G, Di, Pre |
| | V | | G, D, P, Gl, Pre | | | G, D, P, Gl, Pre | G, Di, P, Gl, Pre | G, D, P, Gl, Pre | G, Di, P | G, D, P, Gl, Pre | G, Di, P, Gl, Pre | G, Di, P | G, Di, P |
| | W | | D, P | | | D, P | Di, P | D, P | G, Pre, P | D, P | Di, P | G, Pre, P | G, Pre, P |
| | X | | D, Gl | | | D, Gl | Di, Gl | D, Gl | G, D, Gl, Di | D, Gl | Di, Gl | G, D, Gl, Di | G, D, Gl, Di |
| | Y | | D, Pre | | | D, Pre | Di, Pre | D, Pre | G, D, Gl, Pre | D, Pre | Di, Pre | G, D, Gl, Pre | G, D, Gl, Pre |
| | Z | | P, Gl | | | P, Gl | P, Gl | P, Gl | G, D, Gl, P | P, Gl | P, Gl | G, D, Gl, P | G, D, Gl, P |
| | AA | | P, Pre | | | P, Pre | P, Pre | P, Pre | G, Gl, Di, P | P, Pre | P, Pre | G, Gl, Di, Pre | G, Gl, Di, Pre |
| | AB | | Gl, Pre | | | Gl, Pre | Gl, Pre | Gl, Pre | G, Gl, Di, P | Gl, Pre | Gl, Pre | G, Gl, Di, P | G, Gl, Di, P |
| | AC | | D, P, Gl | | | D, P, Gl | Di, P, Gl | D, P, Gl | G, Gl, Pre, P | D, P, Gl | D, P, Gl | G, Gl, Pre, P | G, Gl, Pre, P |

TABLE 3-continued

Treatments and various options provided for managing weeds in exemplary cropping systems I-XII of the present invention. G-glyphosate, Gl-glufosinate, Pre-a preemergence herbicide, D-dicamba, Gr-a graminicide, Di-2,4-D, Post-a postemergent herbicide, P-paraquat. A graminicide is not used with corn unless the corn has tolerance to the class of herbicides used for controlling grasses, such as a fops herbicide.

| Treatment & Timing | Options | glyphosate tolerant I | dicamba tolerant II | glufosinate tolerant III | glyphosate and glufosinate tolerant IV | dicamba and glufosinate tolerant V | 2,4-D tolerant VI | glyphosate and dicamba tolerant VII | dicamba and 2,4-D tolerant VIII | glyphosate, dicamba and glufosinate tolerant IX | glyphosate and 2,4-D tolerant X | glyphosate, dicamba and 2,4-D tolerant XI | glyphosate, dicamba, glufosinate and 2,4-D tolerant XII |
|---|---|---|---|---|---|---|---|---|---|---|---|---|---|
| | AD | | D, P, Pre | | | D, P, Pre | Di, P, Pre | D, P, Pre | G, Di, Pre, P | D, P, Pre | Di, P, Pre | G, Di, Pre, P | G, Di, Pre, P |
| | AE | | D, Gl, Pre | | | D, Gl, Pre | Di, Gl, Pre | D, Gl, Pre | G, D, Gl, Di, Pre | D, Gl, Pre | Di, Gl, Pre | G, D, Gl, Di, Pre | G, D, Gl, Di, Pre |
| | AF | | D, P, Gl, Pre | | | D, P, Gl, Pre | Di, P, Gl, Pre | D, P, Gl, Pre | G, D, Gl, Di, P | D, P, Gl, Pre | Di, P, Gl, Pre | G, D, Gl, Di, P | G, D, Gl, Di, P |
| | AG | | P, Gl, Pre | | | P, Gl, Pre | P, Gl, Pre | P, Gl, Pre | G, Gl, Di, Pre, P | P, Gl, Pre | P, Gl, Pre | G, Gl, Di, Pre, P | G, Gl, Di, Pre, P |
| | AH | | | | | | | | G, D, Di, Pre, P | | | G, D, Di, Pre, P | G, D, Di, Pre, P |
| | AI | | | | | | | | G, D, Gl, Pre, P | | | G, D, Gl, Pre, P | G, D, Gl, Pre, P |
| | AJ | | | | | | | | G, D, Gl, Di, Pre, P | | | G, D, Gl, Di, Pre, P | G, D, Gl, Di, Pre, P |
| | AK | | | | | | | | D, Gl | | | D, Gl | D, Gl |
| | AL | | | | | | | | D, Di | | | D, Di | D, Di |
| | AM | | | | | | | | D, Pre | | | D, Pre | D, Pre |
| | AN | | | | | | | | D, P | | | D, P | D, P |
| | AO | | | | | | | | Gl, Di | | | Gl, Di | Gl, Di |
| | AP | | | | | | | | Gl, Pre | | | Gl, Pre | Gl, Pre |
| | AQ | | | | | | | | Gl, P | | | Gl, P | Gl, P |
| | AR | | | | | | | | Di, Pre | | | Di, Pre | Di, Pre |
| | AS | | | | | | | | Di, P | | | Di, P | Di, P |
| | AT | | | | | | | | Pre, P | | | Pre, P | Pre, P |
| | AU | | | | | | | | D, Gl, Di | | | D, Gl, Di | D, Gl, Di |
| | AV | | | | | | | | D, Gl, Pre | | | D, Gl, Pre | D, Gl, Pre |
| | AW | | | | | | | | D, Gl, P | | | D, Gl, P | D, Gl, P |
| | AX | | | | | | | | Gl, Di, Pre | | | Gl, Di, Pre | Gl, Di, Pre |
| | AY | | | | | | | | Gl, Di, P | | | Gl, Di, P | Gl, Di, P |
| | AZ | | | | | | | | Gl, Pre, P | | | Gl, Pre, P | Gl, Pre, P |
| | BA | | | | | | | | Di, Pre, P | | | Di, Pre, P | Di, Pre, P |
| | BB | | | | | | | | D, Gl, Di, Pre | | | D, Gl, Di, Pre | D, Gl, Di, Pre |
| | BC | | | | | | | | D, Gl, Di, P | | | D, Gl, Di, P | D, Gl, Di, P |
| | BD | | | | | | | | Gl, Di, Pre, P | | | Gl, Di, Pre, P | Gl, Di, Pre, P |
| | BE | | | | | | | | D, Di, Pre, P | | | D, Di, Pre, P | D, Di, Pre, P |
| | BF | | | | | | | | D, Gl, Pre, P | | | D, Gl, Pre, P | D, Gl, Pre, P |

TABLE 3-continued

Treatments and various options provided for managing weeds in exemplary cropping systems I-XII of the present invention. G-glyphosate, Gl-glufosinate, Gr-graminicide, Pre-a preemergence herbicide, D-dicamba, Di-2,4-D, Post-a postemergent herbicide, P-paraquat. A graminicide is not used with corn unless the corn has tolerance to the class of herbicides used for controlling grasses, such as a fops herbicide.

| Treatment & Timing | Options | glyphosate tolerant I | dicamba tolerant II | glufosinate tolerant III | glyphosate and glufosinate tolerant IV | dicamba and glufosinate tolerant V | 2,4-D tolerant VI | glyphosate and dicamba tolerant VII | dicamba and 2,4-D tolerant VIII | glyphosate, dicamba and glufosinate tolerant IX | glyphosate and 2,4-D tolerant X | glyphosate, dicamba and 2,4-D tolerant XI | glyphosate, dicamba, glufosinate and 2,4-D tolerant XII |
|---|---|---|---|---|---|---|---|---|---|---|---|---|---|
| | BG | | | | | | | | D, Gl, Di, Pre, P | | | D, Gl, Di, Pre, P | D, Gl, Di, Pre, P |
| | BH | | | | | | | | Gl, Di, Pre | | | Gl, Di, Pre | Gl, Di, Pre |
| | BI | | | | | | | | Gl, Di, P | | | Gl, Di, P | Gl, Di, P |
| | BJ | | | | | | | | Di, Pre, P | | | Di, Pre, P | Di, Pre, P |
| | BK | | | | | | | | Di, Pre, P | | | Di, Pre, P | Di, Pre, P |
| | BL | | | | | | | | Gl, Pre, P | | | Gl, Pre, P | Gl, Pre, P |
| | BM | | | | | | | | Gl, Di, Pre, P | | | Gl, Di, Pre, P | Gl, Di, Pre, P |
| Second (2) early post-emerge | A | G | D | Gl | G | D | Di | D | D | G | Di | G | G |
| | B | Gr | Gr | Gr | Gl | Gl | Gr | G | Di | D | G | D | D |
| | C | Post | Post | Post | Gr | Gr | Post | Gr | Gr | Gl | Gr | Gr | Gl |
| | D | G, Gr | D, Gr | Gl, Gr | G, Gl | D, Gl | Di, Post | D, G | D, Di | Post | Di, G | Di | Di |
| | E | G, Post | D, Post | Gl, Post | G, Gr | D, Gr | Di, Post | D, Gr | D, Gr | G, D | Di, Gr | Post | Gr |
| | F | Gr, Post | Gr, Post | Gr, Post | G, Gr | D, Gr | Gr, Post | D, Post | D, Post | G, Gr | Di, Post | G, D | Post |
| | G | G, Gr, Post | D, Gr, Post | Gl, Gr, Post | G, Post | D, Post | Di, Gr, Post | | | | | G, Gr | G, D |
| | H | | | | G, Gl, Gr | D, Gl, Gr | | D, G, Gr | D, Di, Gr | G, Gl | Di, G, Gr | G, D, Gl | G, Gl |
| | I | | | | G, Gl, Post | D, Gl, Post | | D, G, Post | D, Di, Post | G, Post | Di, G, Post | G, Post | G, Di |
| | J | | | | G, Gr, Post | D, Gr, Post | | D, Gr, Post | D, Gr, Post | G, D, Gr | Di, Gr, Post | G, D, Gr | G, Gr |
| | K | | | | G, Gr, Gl, Pot | D, Gr, Gl, Post | | D, Gr, G, Post | D, Gr, Di, Post | G, D, Gl | Di, Gr, G, Post | G, D, Di | G, Post |
| | L | | | | Gl, Gr | Gl, Gr | | G, Gr | Di, Gr | G, D, Post | G, Gr | G, D, Post | G, D, Gl |
| | M | | | | Gl, Post | Gl, Post | | G, Post | Di, Post | G, Gr, Gl | G, Post | G, Gr, Di | G, D, Di |
| | N | | | | Gr, Post | Gr, Post | | Gr, Post | Gr, Post | G, Gr, Post | Gr, Post | G, Gr, Post | G, D, Gr |
| | O | | | | Gr, Gl, Post | Gr, Gl, Post | | Gr, G, Post | Gr, Di, Post | G, Gl, Post | Gr, G, Post | G, Di, Post | G, D, Post |
| | P | | | | | | | | | G, D, Gr, Gl | | G, D, Gr, Di | G, Gl, Di |
| | Q | | | | | | | | | G, D, Gr, Post | | G, D, Gr, Post | G, Gl, Gr |
| | R | | | | | | | | | G, D, Gl, Post | | G, D, Di, Post | G, Gl, Post |
| | S | | | | | | | | | G, Gr, Gl, Post | | G, Gr, Di, Post | G, Di, Gr |
| | T | | | | | | | | | G, D, Gr, Gl, Post | | G, D, Gr, Di, Post | G, Di, Post |

TABLE 3-continued

Treatments and various options provided for managing weeds in exemplary cropping systems I-XII of the present invention. G-glyphosate, Gl-glufosinate, Pre-a preemergence herbicide, D-dicamba, Di-2,4-D, Post-a postemergent herbicide, P-paraquat. A graminicide is not used with corn unless the corn has tolerance to the class of herbicides used for controlling grasses, such as a fops herbicide.

| Treatment & Timing | Options | glyphosate tolerant I | dicamba tolerant II | glufosinate tolerant III | glyphosate and glufosinate tolerant IV | dicamba and glufosinate tolerant V | 2,4-D tolerant VI | glyphosate and dicamba tolerant VII | dicamba and 2,4-D tolerant VIII | glyphosate, dicamba and glufosinate tolerant IX | glyphosate and 2,4-D tolerant X | glyphosate, dicamba and 2,4-D tolerant XI | glyphosate, dicamba, glufosinate and 2,4-D tolerant XII |
|---|---|---|---|---|---|---|---|---|---|---|---|---|---|
| | U | | | | | | | | | D, Gr | | D, Gr | G, Gr, Post |
| | V | | | | | | | | | D, Gl | | D, Di | G, D, Gl, Di |
| | W | | | | | | | | | D, Post | | D, Post | G, D, Gl, Gr |
| | X | | | | | | | | | Gr, Gl | | Gr, Di | G, D, Gl, Post |
| | Y | | | | | | | | | Gr, Post | | Gr, Post | G, Gl, Di, Gr |
| | Z | | | | | | | | | Gl, Post | | Di, Post | G, Gl, Di, Post |
| | AA | | | | | | | | | D, Gr, Gl | | D, Gr, Di | G, Gl, Gr, Post |
| | AS | | | | | | | | | | | | D, Gl, Di |
| | AT | | | | | | | | | | | | D, Gl, Gr |
| | AU | | | | | | | | | | | | D, Gl, Post |
| | AV | | | | | | | | | | | | D, Di, Gr |
| | AW | | | | | | | | | | | | Gl, Di, Post |
| | AX | | | | | | | | | | | | Gl, Gr, Post |
| | AY | | | | | | | | | | | | Di, Gr, Post |
| | AZ | | | | | | | | | | | | D, Gl, Di, Gr |
| | BA | | | | | | | | | | | | D, Gl, Di, Post |
| | BB | | | | | | | | | | | | Gl, Di, Gr, Post |
| | BC | | | | | | | | | | | | D, Di, Gr, Post |
| | BD | | | | | | | | | | | | D, Gl, Gr, Post |
| | BE | | | | | | | | | | | | D, Gl, Di, Gr, Post |
| | BF | | | | | | | | | | | | Gl, Di, Gr |
| | BG | | | | | | | | | | | | Gl, Di, Post |
| | BH | | | | | | | | | | | | Gl, Di, Gr, Post |
| | BI | | | | | | | | | | | | Di, Gr, Post |
| | BJ | | | | | | | | | | | | Gl, Gr, Post |
| | BK | | | | | | | | | | | | Gl, Di, Post |
| Third (3) Late post-emerge | A-BK | Same options as for the second treatment | Same options as for the second treatment | Same options as for the second treatment | Same options as for the second treatment | Same options as for the second treatment | Same options as for the second treatment | Same options as for the second treatment | Same options as for the second treatment | Same options as for the second treatment | Same options as for the second treatment | Same options as for second treatment | Same options as for the second treatment |

TABLE 3-continued

Treatments and various options provided for managing weeds in exemplary cropping systems I-XII of the present invention. G-glyphosate, Gl-glufosinate, Pre-a preemergence herbicide, D-dicamba, Di-2,4-D, Post-a postemergent herbicide, P-paraquat. A graminicide is not used with corn unless the corn has tolerance to the class of herbicides used for controlling grasses, such as a fops herbicide.

| Treatment & Timing | Options | glyphosate tolerant I | dicamba tolerant II | glufosinate tolerant III | glyphosate and glufosinate tolerant IV | dicamba and glufosinate tolerant V | 2,4-D tolerant VI | glyphosate and dicamba tolerant VII | dicamba and 2,4-D tolerant VIII | glyphosate, dicamba and glufosinate tolerant IX | glyphosate and 2,4-D tolerant X | glyphosate, dicamba and 2,4-D tolerant XI | glyphosate, dicamba, glufosinate and 2,4-D tolerant XII |
|---|---|---|---|---|---|---|---|---|---|---|---|---|---|
| Fourth (4) pre-harvest | A | G | G | G | G | G | G | G | G | G | G | G | G |
| | B | D | D | D | D | D | D | D | D | D | D | D | D |
| | C | Di | Di | Di | Di | Di | Di | Di | Di | Di | Di | Di | Di |
| | D | Gl | Gl | Gl | Gl | Gl | Gl | Gl | Gl | Gl | Gl | Gl | Gl |
| | E | Post | Post | Post | Post | Post | Post | Post | Post | Post | Post | Post | Post |
| | F | G, D | G, D | G, D | G, D | G, D | G, D | G, D | G, D | G, D | G, D | G, D | G, D |
| | G | G, Di | G, Di | G, Di | G, Di | G, Di | G, Di | G, Di | G, Di | G, Di | G, Di | G, Di | G, Di |
| | H | G, Gl | G, Gl | G, Gl | G, Gl | G, Gl | G, Gl | G, Gl | G, Gl | G, Gl | G, Gl | G, Gl | G, Gl |
| | I | G, Post | G, Post | G, Post | G, Post | G, Post | G, Post | G, Post | G, Post | G, Post | G, Post | G, Post | G, Post |
| | J | G, D, Di | G, D, Di | G, D, Di | G, D, Di | G, D, Di | G, D, Di | G, D, Di | G, D, Di | G, D, Di | G, D, Di | G, D, Di | G, D, Di |
| | K | G, D, Gl | G, D, Gl | G, D, Gl | G, D, Gl | G, D, Gl | G, D, Gl | G, D, Gl | G, D, Gl | G, D, Gl | G, D, Gl | G, D, Gl | G, D, Gl |
| | L | G, D, Post | G, D, Post | G, D, Post | G, D, Post | G, D, Post | G, D, Post | G, D, Post | G, D, Post | G, D, Post | G, D, Post | G, D, Post | G, D, Post |
| | M | G, Di, Gl | G, Di, Gl | G, Di, Gl | G, Di, Gl | G, Di, Gl | G, Di, Gl | G, Di, Gl | G, Di, Gl | G, Di, Gl | G, Di, Gl | G, Di, Gl | G, Di, Gl |
| | N | G, Di, Post | G, Di, Post | G, Di, Post | G, Di, Post | G, Di, Post | G, Di, Post | G, Di, Post | G, Di, Post | G, Di, Post | G, Di, Post | G, Di, Post | G, Di, Post |
| | O | G, Gl, Post | G, Gl, Post | G, Gl, Post | G, Gl, Post | G, Gl, Post | G, Gl, Post | G, Gl, Post | G, Gl, Post | G, Gl, Post | G, Gl, Post | G, Gl, Post | G, Gl, Post |
| | P | G, D, Di, Gl | G, D, Di, Gl | G, D, Di, Gl | G, D, Di, Gl | G, D, Di, Gl | G, D, Di, Gl | G, D, Di, Gl | G, D, Di, Gl | G, D, Di, Gl | G, D, Di, Gl | G, D, Di, Gl | G, D, Di, Gl |
| | Q | G, D, Di, Post | G, D, Di, Post | G, D, Di, Post | G, D, Di, Post | G, D, Di, Post | G, D, Di, Post | G, D, Di, Post | G, D, Di, Post | G, D, Di, Post | G, D, Di, Post | G, D, Di, Post | G, D, Di, Post |
| | R | G, D, Gl, Post | G, D, Gl, Post | G, D, Gl, Post | G, D, Gl, Post | G, D, Gl, Post | G, D, Gl, Post | G, D, Gl, Post | G, D, Gl, Post | G, D, Gl, Post | G, D, Gl, Post | G, D, Gl, Post | G, D, Gl, Post |
| | S | G, Di, Gl, Post | G, Di, Gl, Post | G, Di, Gl, Post | G, Di, Gl, Post | G, Di, Gl, Post | G, Di, Gl, Post | G, Di, Gl, Post | G, Di, Gl, Post | G, Di, Gl, Post | G, Di, Gl, Post | G, Di, Gl, Post | G, Di, Gl, Post |
| | T | G, D, Di, Gl, Post | G, D, Di, Gl, Post | G, D, Di, Gl, Post | G, D, Di, Gl, Post | G, D, Di, Gl, Post | G, D, Di, Gl, Post | G, D, Di, Gl, Post | G, D, Di, Gl, Post | G, D, Di, Gl, Post | G, D, Di, Gl, Post | G, D, Di, Gl, Post | G, D, Di, Gl, Post |
| | U | D, Di | D, Di | D, Di | D, Di | D, Di | D, Di | D, Di | D, Di | D, Di | D, Di | D, Di | D, Di |
| | V | D, Gl | D, Gl | D, Gl | D, Gl | D, Gl | D, Gl | D, Gl | D, Gl | D, Gl | D, Gl | D, Gl | D, Gl |
| | W | D, Post | D, Post | D, Post | D, Post | D, Post | D, Post | D, Post | D, Post | D, Post | D, Post | D, Post | D, Post |
| | X | Di, Gl | Di, Gl | Di, Gl | Di, Gl | Di, Gl | Di, Gl | Di, Gl | Di, Gl | Di, Gl | Di, Gl | Di, Gl | Di, Gl |
| | Y | Di, Post | Gl, Post | Gl, Post | Gl, Post | Gl, Post | Gl, Post | Gl, Post | Gl, Post | Gl, Post | Gl, Post | Gl, Post | Gl, Post |
| | Z | Gl, Post | Gl, Post | Gl, Post | Gl, Post | Gl, Post | Gl, Post | Gl, Post | Gl, Post | Gl, Post | Gl, Post | Gl, Post | Gl, Post |
| | AA | D, Di, Gl | D, Di, Gl | D, Di, Gl | D, Di, Gl | D, Di, Gl | D, Di, Gl | D, Di, Gl | D, Di, Gl | D, Di, Gl | D, Di, Gl | D, Di, Gl | D, Di, Gl |
| | AB | D, Di, | D, Di, | D, Di, | D, Di, | D, Di, | D, Di, | D, Di, | D, Di, | D, Di, | D, Di, | D, Di, | D, Di, |
| | AC | D, Gl, Post | D, Gl, Post | D, Gl, Post | D, Gl, Post | D, Gl, Post | D, Gl, Post | D, Gl, Post | D, Gl, Post | D, Gl, Post | D, Gl, Post | D, Gl, Post | D, Gl, Post |
| | AD | D, Di, Gl, Post | D, Di, Gl, Post | D, Di, Gl, Post | D, Di, Gl, Post | D, Di, Gl, Post | D, Di, Gl, Post | D, Di, Gl, Post | D, Di, Gl, Post | D, Di, Gl, Post | D, Di, Gl, Post | D, Di, Gl, Post | D, Di, Gl, Post |

TABLE 3-continued

Treatments and various options provided for managing weeds in exemplary cropping systems I-XII of the present invention. G-glyphosate, Gl-glufosinate, Pre-a preemergence herbicide, D-dicamba, Di-2,4-D, Post-a postemergent herbicide, P-paraquat. A graminicide is not used with corn unless the corn has tolerance to the class of herbicides used for controlling grasses, such as a fops herbicide.

| Treatment & Timing | Options | glyphosate tolerant I | dicamba tolerant II | glufosinate tolerant III | glyphosate and glufosinate tolerant IV | dicamba and glufosinate tolerant V | 2,4-D tolerant VI | glyphosate and dicamba tolerant VII | dicamba and 2,4-D tolerant VIII | glyphosate, dicamba and glufosinate tolerant IX | glyphosate and 2,4-D tolerant X | glyphosate, dicamba, and 2,4-D tolerant XI | glyphosate, dicamba, glufosinate and 2,4-D tolerant XII |
|---|---|---|---|---|---|---|---|---|---|---|---|---|---|
| | AE | Di, Gl, Post | Di, Gl, Post | Di, Gl, Post | Di, Gl, Post | Di, Gl, Post | Di, Gl, Post | Di, Gl, Post | Di, Gl, Post | Di, Gl, Post | Di, Gl, Post | Di, Gl, Post | Di, Gl, Post |
| Fifth (5) post-harvest | A | G | G | G | G | G | G | G | G | G | G | G | G |
| | B | G, D | G, D | G, D | G, D | G, D | G, D | G, D | G, D | G, D | G, D | G, D | G, D |
| | C | G, Di | G, Di | G, Di | G, Di | G, Di | G, Di | G, Di | G, Di | G, Di | G, Di | G, Di | G, Di |
| | D | G, Gl | G, Gl | G, Gl | G, Gl | G, Gl | G, Gl | G, Gl | G, Gl | G, Gl | G, Gl | G, Gl | G, Gl |
| | E | G, Post | G, Post | G, Post | G, Post | G, Post | G, Post | G, Post | G, Post | G, Post | G, Post | G, Post | G, Post |
| | F | G, Pre | G, Pre | G, Pre | G, Pre | G, Pre | G, Pre | G, Pre | G, Pre | G, Pre | G, Pre | G, Pre | G, Pre |
| | G | G, P | G, P | G, P | G, P | G, P | G, P | G, P | G, P | G, P | G, P | G, P | G, P |
| | H | G, D, Di | G, D, Di | G, D, Di | G, D, Di | G, D, Di | G, D, Di | G, D, Di | G, D, Di | G, D, Di | G, D, Di | G, D, Di | G, D, Di |
| | I | G, D, Gl | G, D, Gl | G, D, Gl | G, D, Gl | G, D, Gl | G, D, Gl | G, D, Gl | G, D, Gl | G, D, Gl | G, D, Gl | G, D, Gl | G, D, Gl |
| | J | G, D, Post | G, D, Post | G, D, Post | G, D, Post | G,D, Post | G, D, Post | G, D, Post | G, D, Post | G, D, Post | G, D, Post | G, D, Post | G, D, Post |
| | K | G, D, Pre | G, D, Pre | G, D, Pre | G, D, Pre | G, D, Pre | G, D, Pre | G, D, Pre | G, D, Pre | G, D, Pre | G, D, Pre | G, D, Pre | G, D, Pre |
| | L | G, D, P | G, D, P | G, D, P | G, D, P | G, D, P | G, D, P | G, D, P | G, D, P | G, D, P | G, D, P | G, D, P | G, D, P |
| | M | G, Di, Gl | G, Di, Gl | G, Di, Gl | G, Di, Gl | G, Di, Gl | G, Di, Gl | G, Di, Gl | G, Di, Gl | G, Di, Gl | G, Di, Gl | G, Di, Gl | G, Di, Gl |
| | N | G, Di, Post | G, Di, Post | G, Di, Post | G, Di, Post | G, Di, Post | G, Di, Post | G, Di, Post | G, Di, Post | G, Di, Post | G, Di, Post | G, Di, Post | G, Di, Post |
| | O | G, Di, Pre | G, Di, Pre | G, Di, Pre | G, Di, Pre | G, Di, Pre | G, Di, Pre | G, Di, Pre | G, Di, Pre | G, Di, Pre | G, Di, Pre | G, Di, Pre | G, Di, Pre |
| | P | G, Di, P | G, Di, P | G, Di, P | G, Di, P | G, Di, P | G, Di, P | G, Di, P | G, Di, P | G, Di, P | G, Di, P | G, Di, P | G, Di, P |
| | Q | G, Gl | G, Gl | G, Gl | G, Gl | G, Gl | G, Gl | G, Gl | G, Gl | G, Gl | G, Gl | G, Gl | G, Gl, Post |
| | R | G, Gl, Pre | G, Gl, Pre | G, Gl, Pre | G, Gl, Pre | G, Gl, Pre | G, Gl, Pre | G, Gl, Pre | G, Gl, Pre | G, Gl, Pre | G, Gl, Pre | G, Gl, Pre | G, Gl, Pre |
| | S | G, Post, P | G, Post, P | G, Post, P | G, Post, P | G, Post, P | G, Post, P | G, Post, P | G, Post, P | G, Post, P | G, Post, P | G, Post, P | G, Gl, P |
| | T | G, Post, | G, Post, | G, | G, D, Di, | G, D, Di, | G, Pre, P | G, Pre, P | G, Pre, P | G, Pre, P | G, Pre, P | G, Pre, P | G, Post, Pre |
| | U | G, D, Di, | G, D, Di, | G, D, Di, | G, D, Di, | G, D, Di, | G, D, Di, | G, D, Di, | G, D, Di, | G, D, Di, | G, D, Di, | G, D, Di, | G, D, Di, Gl |
| | V | Gl | Pre | Pre | Pre | Pre | Pre | Pre | Pre | Pre | Pre | Pre | |
| | W | G, D, Di, | G, D, Di, | G, D, Di, | G, D, Di, | G, D, Di, | G, D, Di, | G, D, Di, | G, D, Di, | G, D, Di, | G, D, Di, | G, D, Di, | G, D, Di, |
| | X | Post | Post | Post | Post | Post | Post | Post | Post | Post | Post | Post | Post |
| | Y | G, D, Di, | G, D, Di, | G, D, Di, | G, D, Di, | G, D, Di, | G, D, Di, | G, D, Di, | G, D, Di, | G, D, Di, | G, D, Di, | G, D, Di, | G, D, Di, Pre |
| | Z | G, D, Di, P | G, D, Di, P | G, D, Di, P | G, D, Di, P | G, D, Di, P | G, D, Di, P | G, D, Di, P | G, D, Di, P | G, D, Di, P | G, D, Di, P | G, D, Di, P | G, D, Di, P |
| | AA | G, D, Gl, | G, D, Gl, | G, D, Gl, | G, D, Gl, | G, D, Gl, | G, D, Gl, | G, D, Gl, | G, D, Gl, | G, D, Gl, | G, D, Gl, | G, D, Gl, | G, D, Gl, |
| | | Post | Post | Post | Post | Post | Post | Post | Post | Post | Post | Post | Post |
| | AB | G, D, Gl | G, D, Gl | G, D, Gl | G, D, Gl | G, D, Gl | G, D, Gl | G, D, Gl | G, D, Gl | G, D, Gl | G, D, Gl | G, D, Gl | G, D, Gl |
| | AC | G, D, Gl, P | G, D, Gl, P | G, D, Gl, P | G, D, Gl, P | G, D, Gl, P | G, D, Gl, P | G, D, Gl, P | G, D, Gl, P | G, D, Gl, P | G, D, Gl, P | G, D, Gl, P | G, D, Gl, P |
| | AD | G, D, Post, Pre | G, D, Post, Pre | G, D, Post, Pre | G, D, Post, Pre | G, D, Post, Pre | G, D, Post, Pre | G, D, Post, Pre | G, D, Post, Pre | G, D, Post, Pre | G, D, Post, Pre | G, D, Post, Pre | G, D, Post, Pre |

TABLE 3-continued

Treatments and various options provided for managing weeds in exemplary cropping systems I-XII of the present invention. G-glyphosate, Gl-glufosinate, Pre-a preemergence herbicide, D-dicamba, Di-2,4-D, Post-a postemergent herbicide, P-paraquat. A graminicide is not used with corn unless the corn has tolerance to the class of herbicides used for controlling grasses, such as a fops herbicide.

| Treatment & Timing | Options | glyphosate tolerant I | dicamba tolerant II | glufosinate tolerant III | glyphosate and glufosinate tolerant IV | dicamba and glufosinate tolerant V | 2,4-D tolerant VI | glyphosate and dicamba tolerant VII | dicamba and 2,4-D tolerant VIII | glyphosate, dicamba and glufosinate tolerant IX | glyphosate and 2,4-D tolerant X | glyphosate, dicamba and 2,4-D tolerant XI | glyphosate, dicamba, glufosinate and 2,4-D tolerant XII |
|---|---|---|---|---|---|---|---|---|---|---|---|---|---|
| | AE | G, D, Post, P | G, D, Post, P | G, D, Post, P | G, D, Post, P | G, D, Post, P | G, D, Post, P | G, D, Post, P | G, D, Post, P | G, D, Post, P | G, D, Post, P | G, D, Post, P | G, D, Post, P |
| | AF | G, D, Pre, P | G, D, Pre, P | G, D, Pre, P | G, D, Pre, P | G, D, Pre, P | G, D, Pre, P | G, D, Pre, P | G, D, Pre, P | G, D, Pre, P | G, D, Pre, P | G, D, Pre, P | G, D, Pre, P |
| | AG | G, Di, Gl | G, Di, Gl | G, Di, Gl | G, Di, Gl | G, Di, Gl | G, Di, Gl | G, Di, Gl | G, Di, Gl | G, Di, Gl | G, Di, Gl | G, Di, Gl | G, Di, Gl |
| | AH | Post | Post | Post | Post | Post | Post | Post | Post | Post | Post | Post | Post |
| | AH | G, Di, Gl, | G, Di, Gl, | G, Di, Gl, | G, Di, Gl, | G,Di, Gl, | G, Di, Gl, | G, Di, Gl, | G, Di, Gl, | G, Di, Gl, | G, Di, Gl, | G, Di, Gl, | G, Di, Gl, |
| | AI | Pre | Pre | Pre | Pre | Pre | Pre | Pre | Pre | Pre | Pre | Pre | Pre |
| | AI | G, Di, Gl, P | G, Di, Gl, P | G, Di, Gl, P | G, Di, Gl, P | G, Di, Gl, P | G, Di, Gl, P | G, Di, Gl, P | G, Di, Gl, P | G, Di, Gl, P | G, Di, Gl, P | G, Di, Gl, P | G, Di, Gl, P |
| | AJ | G, Di, Post, | G, Di, Post, | G, Di, Post, | G, Di, Post, | G, Di, | G, Di, | G, Di, | G, Di, | G, Di, | G, Di, | G, Di, | G, Di, Post, |
| | AJ | Pre | Pre | Pre | Pre | Pre | Pre | Pre | Pre | Pre | Pre | Pre | Pre |
| | AK | G, Di, | G, Di, | G, Di, | G, Di, | G, Di, | G, Di, | G, Di, | G, Di, | G, Di, | G, Di, | G, Di, | G, Di, Post, P |
| | AK | Post, P | Post, P | Post, P | Post, P | Post, P | Post, P | Post, P | Post, P | Post, P | Post, P | Post, P | Pre |
| | AL | G, Di, | G, Di, | G, Di, | G, Di, | G, Di, | G, Di, | G, Di, | G, Di, | G, Di, | G, Di, | G, Di, | G, Di, Pre, P |
| | AL | Pre, P | Pre, P | Pre, P | Pre, P | Pre, P | Pre, P | Pre, P | Pre, P | Pre, P | Pre, P | Pre, P | |
| | AM | G, Gl, | G, Gl, | G, Gl, | G, Gl, | G, Gl, | G, Gl, | G, Gl, | G, Gl, | G, Gl, | G, Gl, | G, Gl, | G, Gl, Post, Pre |
| | AM | Post, Pre | Post, Pre | Post, Pre | Post, Pre | Post, Pre | Post, Pre | Post, Pre | Pos | Post, Pre | Post, Pre | Post, Pre | |
| | AN | G, Gl, | G, Gl, | G, Gl, | G, Gl, | G, Gl, | G, Gl, | G, Gl, | G, Gl, | G, Gl, | G, Gl, | G, Gl, | G, Gl, Post, P |
| | AN | Post, P | Post, P | Post, P | Post, P | Post, P | Post, P | Post, P | Post, P | Post, P | Post, P | Post, P | |
| | AO | G, Gl, Pre, P | G, Gl, Pre, P | G, Gl, Pre, P | G, Gl, Pre, P | G, Gl, Pre, P | G, Gl, Pre, P | G, Gl, Pre, P | G, Gl, Pre, P | G, Gl, Pre, P | G, Gl, Pre, P | G, Gl, Pre, P | G, Gl, Pre, P |
| | AP | G, Post, Pre, P | G, Post, Pre, P | G, Post, Pre, P | G, Post, Pre, P | G, Post, Pre, P | G, Post, Pre, P | G, Post, Pre, P | G, Post, Pre, P | G, Post, Pre, P | G, Post, Pre, P | G, Post, Pre, P | G, Post, Pre, P |
| | AQ | G, D, Di, Gl, Post | G, D, Di, Gl, Post | G, D, Di, Gl, Post | G, D, Di, Gl, Post | G, D, Di, Gl, Post | G, D, Di, Gl, Post | G, D, Di, Gl, Post | G, D, Di, Gl, Post | G, D, Di, Gl, Post | G, D, Di, Gl, Post | G, D, Di, Gl, Post | G, D, Di, Gl, Post |
| | AR | G, D, Di, Gl, Pre | G, D, Di, Gl, Pre | G, D, Di, Gl, Pre | G, D, Di, Gl, Pre | G, D, Di, Gl, Pre | G, D, Di, Gl, Pre | G, D, Di, Gl, Pre | G, D, Di, Gl, Pre | G, D, Di, Gl, Pre | G, D, Di, Gl, Pre | G, D, Di, Gl, Pre | G, D, Di, Gl, Pre |
| | AS | G, D, Di, Gl, P | G, D, Di, Gl, P | G, D, Di, Gl, P | G, D, Di, Gl, P | G, D, Di, Gl, P | G, D, Di, Gl, P | G, D, Di, Gl, P | G, D, Di, Gl, P | G, D, Di, Gl, P | G, D, Di, Gl, P | G, D, Di, Gl, P | G, D, Di, Gl, P |
| | AT | G, D, Di, Post, Pre | G, D, Di, Post, Pre | G, D, Di, Post, Pre | G, D, Di, Post, Pre | G, D, Di, Post, Pre | G, D, Di, Post, Pre | G, D, Di, Post, Pre | G, D, Di, Post, Pre | G, D, Di, Post, Pre | G, D, Di, Post, Pre | G, D, Di, Post, Pre | G, D, Di, Post, Pre |
| | AU | G, D, Di, Post, P | G, D, Di, Post, P | G, D, Di, Post, P | G, D, Di, Post, P | G, D, Di, Post, P | G, D, Di, Post, P | G, D, Di, Post, P | G, D, Di, Post, P | G, D, Di, Post, P | G, D, Di, Post, P | G, D, Di, Post, P | G, D, Di, Post, P |
| | AV | G, D, Di, Pre, P | G, D, Di, Pre, P | G, D, Di, Pre, P | G, D, Di, Pre, P | G, D, Di, Pre, P | G, D, Di, Pre, P | G, D, Di, Pre, P | G, D, Di, Pre, P | G, D, Di, Pre, P | G, D, Di, Pre, P | G, D, Di, Pre, P | G, D, Di, Pre, P |
| | AW | G, D, Gl, Post, Pre | G, D, Gl, Post, Pre | G, D, Gl, Post, Pre | G, D, Gl, Post, Pre | G, D, Gl, Post, Pre | G, D, Gl, Post, Pre | G, D, Gl, Post, Pre | G, D, Gl, Post, Pre | G, D, Gl, Post, Pre | G, D, Gl, Post, Pre | G, D, Gl, Post, Pre | G, D, Gl, Post, Pre |
| | AX | G, D, Gl, Post, P | G, D, Gl, Post, P | G, D, Gl, Post, P | G, D, Gl, Post, P | G, D, Gl, Post, P | G, D, Gl, Post, P | G, D, Gl, Post, P | G, D, Gl, Post, P | G, D, Gl, Post, P | G, D, Gl, Post, P | G, D, Gl, Post, P | G, D, Gl, Post, P |
| | AY | G, D, Gl, Pre, P | G, D, Gl, Pre, P | G, D, Gl, Pre, P | G, D, Gl, Pre, P | G, D, Gl, Pre, P Pre, P | G, D, Gl, Pre, P | G, D, Gl, Pre, P | G, D, Gl, Pre, P | G, D, Gl, Pre, P | G, D, Gl, Pre, P | G, D, Gl, Pre, P | G, D, Gl, Pre, P |

TABLE 3-continued

Treatments and various options provided for managing weeds in exemplary cropping systems I-XII of the present invention. G-glyphosate, Gl-glufosinate, Pre-a preemergence herbicide, D-dicamba, Di-2,4-D, Post-a postemergent herbicide, P-paraquat. A graminicide is not used with corn unless the corn has tolerance to the class of herbicides used for controlling grasses, such as a fops herbicide.

| Treatment & Timing | Options | glyphosate tolerant I | dicamba tolerant II | glufosinate tolerant III | glyphosate and glufosinate tolerant IV | dicamba and glufosinate tolerant V | 2,4-D tolerant VI | glyphosate and dicamba tolerant VII | dicamba and 2,4-D tolerant VIII | glyphosate, dicamba and glufosinate tolerant IX | glyphosate and 2,4-D tolerant X | glyphosate, dicamba and 2,4-D tolerant XI | glyphosate, dicamba, glufosinate and 2,4-D tolerant XII |
|---|---|---|---|---|---|---|---|---|---|---|---|---|---|
| | AZ | G, D, Post, Pre, P | G, D, Post, Pre, P | G, D, Post, Pre, P | G, D, Post, Pre, P | G, D, Post, Pre, P | G, D, Post, Pre, P | G, D, Post, Pre, P | G, D, Post, Pre, P | G, D, Post, Pre, P | G, D, Post, Pre, P | G, D, Post, Pre, P | G, D, Post, Pre, P |
| | BA | G, Di, Gl, Post, Pre | G, Di, Gl, Post, Pre | G, Di, Gl, Post, Pre | G, Di, Gl, Post, Pre | G, Di, Gl, Post, Pre | G, Di, Gl, Post, Pre | G, Di, Gl, Post, Pre | G, Di, Gl, Post, Pre | G, Di, Gl, Post, Pre | G, Di, Gl, Post, Pre | G, Di, Gl, Post, Pre | G, Di, Gl, Post, Pre |
| | BB | G, Di, Gl, Post, P | G, Di, Gl, Post, P | G, Di, Gl, Post, P | G, Di, Gl, Post, P | G, Di, Gl, Post, P | G, Di, Gl, Post, P | G, Di, Gl, Post, P | G, Di, Gl, Post, P | G, Di, Gl, Post, P | G, Di, Gl, Post, P | G, Di, Gl, Post, P | G, Di, Gl, Post, P |
| | BC | G, Di, Gl, Pre, P | G, Di, Gl, Pre, P | G, Di, Gl, Pre, P | G, Di, Gl, Pre, P | G, Di, Gl, Pre, P | G, Di, Gl, Pre, P | G, Di, Gl, Pre, P | G, Di, Gl, Pre, P | G, Di, Gl, Pre, P | G, Di, Gl, Pre, P | G, Di, Gl, Pre, P | G, Di, Gl, Pre, P |
| | BD | G, Di, Post, Pre, P | G, Di, Post, Pre, P | G, Di, Post, Pre, P | G, Di, Post, Pre, P | G, Di, Post, Pre, P | G, Di, Post, Pre, P | G, Di, Post, Pre, P | G, Di, Post, Pre, P | G, Di, Post, Pre, P | G, Di, Post, Pre, P | G, Di, Post, Pre, P | G, Di, Post, Pre, P |
| | BE | G, Gl, Post, Pre, P | G, Gl, Post, Pre, P | G, Gl, Post, Pre, P | G, Gl, Post, Pre, P | G, Gl, Post, Pre, P | G, Gl, Post, Pre, P | G, Gl, Post, Pre, P | G, Gl, Post, Pre, P | G, Gl, Post, Pre, P | G, Gl, Post, Pre, P | G, Gl, Post, Pre, P | G, Gl, Post, Pre, P |
| | BF | G, D, Di, Gl, Post, Pre | G, D, Di, Gl, Post, Pre | G, D, Di, Gl, Post, Pre | G, D, Di, Gl, Post, Pre | G, D, Di, Gl, Post, Pre | G, D, Di, Gl, Post, Pre | G, D, Di, Gl, Post, Pre | G, D, Di, Gl, Post, Pre | G, D, Di, Gl, Post, Pre | G, D, Di, Gl, Post, Pre | G, D, Di, Gl, Post, Pre | G, D, Di, Gl, Post, Pre |
| | BG | G, D, Di, Gl, Post, P | G, D, Di, Gl, Post, P | G, D, Di, Gl, Post, P | G, D, Di, Gl, Post, P | G, D, Di, Gl, Post, P | G, D, Di, Gl, Post, P | G, D, Di, Gl, Post, P | G, D, Di, Gl, Post, P | G, D, Di, Gl, Post, P | G, D, Di, Gl, Post, P | G, D, Di, Gl, Post, P | G, D, Di, Gl, Post, P |
| | BH | G, D, Di, Gl, Pre, P | G, D, Di, Gl, Pre, P | G, D, Di, Gl, Pre, P | G, D, Di, Gl, Pre, P | G, D, Di, Gl, Pre, P | G, D, Di, Gl, Pre, P | G, D, Di, Gl, Pre, P | G, D, Di, Gl, Pre, P | G, D, Di, Gl, Pre, P | G, D, Di, Gl, Pre, P | G, D, Di, Gl, Pre, P | G, D, Di, Gl, Pre, P |
| | BI | G, D, Di, Post, Pre, P | G, D, Di, Post, Pre, P | G, D, Di, Post, Pre, P | G, D, Di, Post, Pre, P | G, D, Di, Post, Pre, P | G, D, Di, Post, Pre, P | G, D, Di, Post, Pre, P | G, D, Di, Post, Pre, P | G, D, Di, Post, Pre, P | G, D, Di, Post, Pre, P | G, D, Di, Post, Pre, P | G, D, Di, Post, Pre, P |
| | BJ | G, D, Gl, Post, Pre, P | G, D, Gl, Post, Pre, P | G, D, Gl, Post, Pre, P | G, D, Gl, Post, Pre, P | G, D, Gl, Post, Pre, P | G, D, Gl, Post, Pre, P | G, D, Gl, Post, Pre, P | G, D, Gl, Post, Pre, P | G, D, Gl, Post, Pre, P | G, D, Gl, Post, Pre, P | G, D, Gl, Post, Pre, P | G, D, Gl, Post, Pre, P |
| | BK | G, Di, Gl, Post, Pre, P | G, Di, Gl, Post, Pre, P | G, Di, Gl, Post, Pre, P | G, Di, Gl, Post, Pre, P | G, Di, Gl, Post, Pre, P | G, Di, Gl, Post, Pre, P | G, Di, Gl, Post, Pre, P | G, Di, Gl, Post, Pre, P | G, Di, Gl, Post, Pre, P | G, Di, Gl, Post, Pre, P | G, Di, Gl, Post, Pre, P | G, Di, Gl, Post, Pre, P |
| | BL | G, D, Di, Gl, Post, Pre, P | G, D, Di, Gl, Post, Pre, P | G, D, Di, Gl, Post, Pre, P | G, D, Di, Gl, Post, Pre, P | G, D, Di, Gl, Post, Pre, P | G, D, Di, Gl, Post, Pre, P | G, D, Di, Gl, Post, Pre, P | G, D, Di, Gl, Post, Pre, P | G, D, Di, Gl, Post, Pre, P | G, D, Di, Gl, Post, Pre, P | G, D, Di, Gl, Post, Pre, P | G, D, Di, Gl, Post, Pre, P |
| | BM | D | D | D | D | D | D | D | D | D | D | D | D |
| | BN | D, Di | D, Di | D, Di | D, Di | D, Di | D, Di | D, Di | D, Di | D, Di | D, Di | D, Di | D, Di |
| | BO | D, Gl | D, Gl | D, Gl | D, Gl | D, Gl | D, Gl | D, Gl | D, Gl | D, Gl | D, Gl | D, Gl | D, Gl |
| | BP | D, Post | D, Post | D, Post | D, Post | D, Post | D, Post | D, Post | D, Post | D, Post | D, Post | D, Post | D, Post |
| | BQ | D, Pre | D, Pre | D, Pre | D, Pre | D, Pre | D, Pre | D, Pre | D, Pre | D, Pre | D, Pre | D, Pre | D, Pre |
| | BR | D, P | D, P | D, P | D, P | D, P | D, P | D, P | D, P | D, P | D, P | D, P | D, P |
| | BS | D, Di, Gl | D, Di, Gl | D, Di, Gl | D, Di, Gl | D, Di, Gl | D, Di, Gl | D, Di, Gl | D, Di, Gl | D, Di, Gl | D, Di, Gl | D, Di, Gl | D, Di, Gl |
| | BT | D, Di, Post | D, Di, Post | D, Di, Post | D, Di, Post | D, Di, Post | D, Di, Post | D, Di, Post | D, Di, Post | D, Di, Post | D, Di, Post | D, Di, Post | D, Di, Post |
| | BU | D, Di, Pre | D, Di, Pre | D, Di, Pre | D, Di, Pre | D, Di, Pre | D, Di, Pre | D, Di, Pre | D, Di, Pre | D, Di, Pre | D, Di, Pre | D, Di, Pre | D, Di, Pre |
| | BV | D, Di, P | D, Di, P | D, Di, P | D, Di, P | D, Di, P | D, Di, P | D, Di, P | D, Di, P | D, Di, P | D, Di, P | D, Di, P | D, Di, P |
| | BW | D, Gl, Post | D, Gl, Post | D, Gl, Post | D, Gl, Post | D, Gl, Post | D, Gl, Post | D, Gl, Post | D, Gl, Post | D, Gl, Post | D, Gl, Post | D, Gl, Post | D, Gl, Post |

TABLE 3-continued

Treatments and various options provided for managing weeds in exemplary cropping systems I-XII of the present invention. G-glyphosate, Gl-glufosinate, Pre-a preemergence herbicide, D-dicamba, Gr-a graminicide, Di-2,4-D, Post-a postemergent herbicide, P-paraquat. A graminicide is not used with corn unless the corn has tolerance to the class of herbicides used for controlling grasses, such as a fops herbicide.

| Treatment & Timing | Options | glyphosate tolerant I | dicamba tolerant II | glufosinate tolerant III | glyphosate and glufosinate tolerant IV | dicamba and glufosinate tolerant V | 2,4-D tolerant VI | glyphosate and dicamba tolerant VII | dicamba and 2,4-D tolerant VIII | glyphosate, dicamba and glufosinate tolerant IX | glyphosate and 2,4-D tolerant X | glyphosate, dicamba and 2,4-D tolerant XI | glyphosate, dicamba, glufosinate and 2,4-D tolerant XII |
|---|---|---|---|---|---|---|---|---|---|---|---|---|---|
| | BX | D, Gl, Pre | D, Gl, Pre | D, Gl, Pre | D, Gl, Pre | D, Gl, Pre | D, Gl, Pre | D, Gl, Pre | D, Gl, Pre | D, Gl, Pre | D, Gl, Pre | D, Gl, Pre | D, Gl, Pre |
| | BY | D, Gl, P | D, Gl, P | D, Gl, P | D, Gl, P | D, Gl, P | D, Gl, P | D, Gl, P | D, Gl, P | D, Gl, P | D, Gl, P | D, Gl, P | D, Gl, P |
| | BZ | D, Post, Pre | D, Post, Pre | D, Post, Pre | D, Post, Pre | D, Post, Pre | D, Post, Pre | D, Post, Pre | D, Post, Pre | D, Post, Pre | D, Post, Pre | D, Post, Pre | D, Post, Pre |
| | CA | D, Post, P | D, Post, P | D, Post, P | D, Post, P | D, Post, P | D, Post, P | D, Post, P | D, Post, P | D, Post, P | D, Post, P | D, Post, P | D, Post, P |
| | CB | D, Pre, P | D, Pre, P | D, Pre, P | D, Pre, P | D, Pre, P | D, Pre, P | D, Pre, P | D, Pre, P | D, Pre, P | D, Pre, P | D, Pre, P | D, Pre, P |
| | CC | D, Di, Gl | D, Di, Gl | D, Di, Gl | D, Di, Gl | D, Di, Gl | D, Di, Gl | D, Di, Gl | D, Di, Gl | D, Di, Gl | D, Di, Gl | D, Di, Gl | D, Di, Gl |
| | CD | Post | Post | Post | Post | Post | Post | Post | Post | Post | Post | Post | Post |
| | | D, Di, Gl | D, Di, Gl | D, Di, Gl | D, Di, Gl | D, Di, Gl | D, Di, Gl | D, Di, Gl | D, Di, Gl | D, Di, Gl | D, Di, Gl | D, Di, Gl | D, Di, Gl |
| | | Pre | Pre | Pre | Pre | Pre | Pre | Pre | Pre | Pre | Pre | Pre | Pre |
| | CE | D, Di, Gl, P | D, Di, Gl, P | D, Di, Gl, P | D, Di, Gl, P | D, Di, Gl, P | D, Di, Gl, P | D, Di, Gl, P | D, Di, Gl, P | D, Di, Gl, P | D, Di, Gl, P | D, Di, Gl, P | D, Di, Gl, P |
| | CF | D, Di, | | | | | | | | | | | |
| | | Post, Pre | Post, Pre | Post, Pre | Post, Pre | Post, Pre | Post, Pre | Post, Pre | Post, Pre | Post, Pre | Post, Pre | Post, Pre | Pre |
| | CG | D, Di, | D, Di, | D, Di, | D, Di, | D, Di, | D, Di, | D, Di, | D, Di, | D, Di, | D, Di, | D, Di, | D, Di, Post, P |
| | CH | D, Di, | D, Di, | D, Di, | D, Di, | D, Di, | D, Di, | D, Di, | D, Di, | D, Di, | D, Di, | D, Di, | D, Di, |
| | | Post, P | Post, P | Post, P | Post, P | Post, P | Post, P | Post, P | Post, P | Post, P | Post, P | Post, P | Pre, P |
| | CI | Pre, P | Pre, P | Pre, P | Pre, P | Pre, P | Pre, P | Pre, P | Pre, P | Pre, P | Pre, P | Pre, P | D, Gl, Post, Pre |
| | CJ | D, Gl, | D, Gl, | D, Gl, | D, Gl, | D, Gl, | D, Gl, | D, Gl, | D, Gl, | D, Gl, | D, Gl, | D, Gl, | D, Gl, |
| | | Post, Pre | Post, Pre | Post, Pre | Post, Pre | Post, Pre | Post, Pre | Post, Pre | Post, Pre | Post, Pre | Post, Pre | Post, Pre | D, Gl, Post, P |
| | CK | D, Gl, | D, Gl, | D, Gl, | D, Gl, | D, Gl, | D, Gl, | D, Gl, | D, Gl, | D, Gl, | D, Gl, | D, Gl, | D, Gl, Pre, P |
| | | Post, P | Post, P | Post, P | Post, P | Post, P | Post, P | Post, P | Post, P | Post, P | Post, P | Post, P | |
| | CL | D, Gl, | D, Gl, | D, Gl, | D, Gl, | D, Gl, | D, Gl, | D, Gl, | D, Gl, | D, Gl, | D, Gl, | D, Gl, | D, Post, Pre, P |
| | | Pre, P | Pre, P | Pre, P | Pre, P | Pre, P | Pre, P | Pre, P | Pre, P | Pre, P | Pre, P | Pre, P | |
| | CM | D, Post, | D, Post, | D, Post, | D, Post, | D, Post, | D, Post, | D, Post, | D, Post, | D, Post, | D, Post, | D, Post, | |
| | | Pre, P | Pre, P | Pre, P | Pre, P | Pre, P | Pre, P | Pre, P | Pre, P | Pre, P | Pre, P | Pre, P | |
| | CN | D, Di, Gl, | D, Di, Gl, | D, Di, Gl, | D, Di, Gl, | D, Di, Gl, | D, Di, Gl, | D, Di, Gl, | D, Di, Gl, | D, Di, Gl, | D, Di, Gl, | D, Di, Gl, | D, Di, Gl, |
| | | Post, Pre | Post, Pre | Post, Pre | Post, Pre | Post, Pre | Post, Pre | Post, Pre | Post, Pre | Post, Pre | Post, Pre | Post, Pre | Post, Pre |
| | CO | D, Di, Gl, | D, Di, Gl, | D, Di, Gl, | D, Di, Gl, | D, Di, Gl, | D, Di, Gl, | D, Di, Gl, | D, Di, Gl, | D, Di, Gl, | D, Di, Gl, | D, Di, Gl, | D, Di, Gl, |
| | | Post, P | Post, P | Post, P | Post, P | Post, P | Post, P | Post, P | Post, P | Post, P | Post, P | Post, P | Post, P |
| | CP | D, Di, Gl, | D, Di, Gl, | D, Di, Gl, | D, Di, Gl, | D, Di, Gl, | D, Di, Gl, | D, Di, Gl, | D, Di, Gl, | D, Di, Gl, | D, Di, Gl, | D, Di, Gl, | D, Di, Gl, |
| | | Pre, P | Pre, P | Pre, P | Pre, P | Pre, P | Pre, P | Pre, P | Pre, P | Pre, P | Pre, P | Pre, P | Pre, P |
| | CQ | D, Di, | D, Di, | D, Di, | D, Di, | D, Di, | D, Di, | D, Di, | D, Di, | D, Di, | D, Di, | D, Di, | D, Di, |
| | | Post, Pre, P | Post, Pre, P | Post, Pre, P | Post, Pre, P | Post, Pre, P | Post, Pre, P | Post, Pre, P | Post, Pre, P | Post, Pre, P | Post, Pre, P | Post, Pre, P | Post, Pre, P |
| | CR | D, Gl, | D, Gl, | D, Gl, | D, Gl, | D, Gl, | D, Gl, | D, Gl, | D, Gl, | D, Gl, | D, Gl, | D, Gl, | D, Gl, Post, Pre, P |
| | | Post, Pre, P | Post, Pre, P | Post, Pre, P | Post, Pre, P | Post, Pre, P | Post, Pre, P | Post, Pre, P | Post, Pre, P | Post, Pre, P | Post, Pre, P | Post, Pre, P | |
| | CS | Di | Di | Di | Di | Di | Di | Di | Di | Di | Di | Di | Di |
| | CT | Di, Gl | Di, Gl | Di, Gl | Di, Gl | Di, Gl | Di, Gl | Di, Gl | Di, Gl | Di, Gl | Di, Gl | Di, Gl | Di, Gl |
| | CU | Di, Post | Di, Post | Di, Post | Di, Post | Di, Post | Di, Post | Di, Post | Di, Post | Di, Post | Di, Post | Di, Post | Di, Post |
| | CV | Di, Pre | Di, Pre | Di, Pre | Di, Pre | Di, Pre | Di, Pre | Di, Pre | Di, Pre | Di, Pre | Di, Pre | Di, Pre | Di, Pre |

TABLE 3-continued

Treatments and various options provided for managing weeds in exemplary cropping systems I-XII of the present invention. G-glyphosate, Gl-glufosinate, Pre-a preemergence herbicide, D-dicamba, Di-2,4-D, Post-a postemergent herbicide, P-paraquat. A graminicide is not used with corn unless the corn has tolerance to the class of herbicides used for controlling grasses, such as a fops herbicide.

| Treatment & Timing | Options | glyphosate tolerant I | dicamba tolerant II | glufosinate tolerant III | glyphosate and glufosinate tolerant IV | dicamba and glufosinate tolerant V | 2,4-D tolerant VI | glyphosate and dicamba tolerant VII | dicamba and 2,4-D tolerant VIII | glyphosate, dicamba and glufosinate tolerant IX | glyphosate and 2,4-D tolerant X | glyphosate, dicamba and 2,4-D tolerant XI | glyphosate, dicamba, glufosinate and 2,4-D tolerant XII |
|---|---|---|---|---|---|---|---|---|---|---|---|---|---|
| | CW | Di, P | Di, P | Di, P | Di, P | Di, P | Di, P | Di, P | Di, P | Di, P | Di, P | Di, P | Di, P |
| | CX | Di, Gl, Post | Di, Gl, Post | Di, Gl, Post | Di, Gl, Post | Di, Gl, Post | Di, Gl, Post | Di, Gl, Post | Di, Gl, Post | Di, Gl, Post | Di, Gl, Post | Di, Gl, Post | Di, Gl, Post |
| | CY | Di, Gl, Pre | Di, Gl, Pre | Di, Gl, Pre | Di, Gl, Pre | Di, Gl, Pre | Di, Gl, Pre | Di, Gl, Pre | Di, Gl, Pre | Di, Gl, Pre | Di, Gl, Pre | Di, Gl, Pre | Di, Gl, Pre |
| | CZ | Di, Gl, P | Di, G | | | | | | | | | | |
| | DA | Di, Post, Pre | Di, Post, Pre | Di, Post, Pre | Di, Post, Pre | Di, Post, Pre | Di, Post, Pre | Di, Post, Pre | Di, Post, Pre | Di, Post, Pre | Di, Post, Pre | Di, Post, Pre | Di, Post, Pre |
| | DB | Di, Post, P | Di, Post, P | Di, Post, P | Di, Post, P | Di, Post, P | Di, Post, P | Di, Post, P | Di, Post, P | Di, Post, P | Di, Post, P | Di, Post, P | Di, Post, P |
| | DC | Di, Pre, P | Di, Pre, P | Di, Pre, P | Di, Pre, P | Di, Pre, P | Di, Pre, P | Di, Pre, P | Di, Pre, P | Di, Pre, P | Di, Pre, P | Di, Pre, P | Di, Pre, P |
| | DD | Di, Gl, Post, Pre | Di, Gl, Post, Pre | Di, Gl, Post, Pre | Di, Gl, Post, Pre | Di, Gl, Post, Pre | Di, Gl, Post, Pre | Di, Gl, Post, Pre | Di, Gl, Post, Pre | Di, Gl, Post, Pre | Di, Gl, Post, Pre | Di, Gl, Post, Pre | Di, Gl, Post, Pre |
| | DE | Di, Gl, Post, P | Di, Gl, Post, P | Di, Gl, Post, P | Di, Gl, Post, P | Di, Gl, Post, P | Di, Gl, Post, P | Di, Gl, Post, P | Di, Gl, Post, P | Di, Gl, Post, P | Di, Gl, Post, P | Di, Gl, Post, P | Di, Gl, Post, P |
| | DF | Di, Gl, Pre, P | Di, Gl, Pre, P | Di, Gl, Pre, P | Di, Gl, Pre, P | Di, Gl, Pre, P | Di, Gl, Pre, P | Di, Gl, Pre, P | Di, Gl, Pre, P | Di, Gl, Pre, P | Di, Gl, Pre, P | Di, Gl, Pre, P | Di, Gl, Pre, P |
| | DG | Di, Post, Pre, P | Di, Post, Pre, P | Di, Post, Pre, P | Di, Post, Pre, P | Di, Post, Pre, P | Di, Post, Pre, P | Pot, Pre, P | Di, Post, Pre, P | Di, Post, Pre, P | Di, Post, Pre, P | Di, Post, Pre, P | Di, Post, Pre, P |
| | DH | Di, Gl, Post, Pre, P | Di, Gl, Post, Pre, P | Di, Gl, Post, Pre, P | Di, Gl, Post, Pre, P | Di, Gl, Post, Pre, P | Di, Gl, Post, Pre, P | Di, Gl, Post, Pre, P | Di, Gl, Post, Pre, P | Di, Gl, Post, Pre, P | Di, Gl, Post, Pre, P | Di, Gl, Post, Pre, P | Di, Gl, Post, Pre, P |
| | DI | Gl | Gl | Gl | Gl | Gl | Gl | Gl | Gl | Gl | Gl | Gl | Gl |
| | DJ | Gl, Post | Gl, Post | Gl, Post | Gl, Post | Gl, Post | Gl, Post | Gl, Post | Gl, Post | Gl, Post | Gl, Post | Gl, Post | Gl, Post |
| | DK | Gl, Pre | Gl, Pre | Gl, Pre | Gl, Pre | Gl, Pre | Gl, Pre | Gl, Pre | Gl, Pre | Gl, Pre | Gl, Pre | Gl, Pre | Gl, Pre |
| | DL | Gl, P | Gl, P | Gl, P | Gl, P | Gl, P | Gl, P | Gl, P | Gl, P | Gl, P | Gl, P | Gl, P | Gl, P |
| | DM | Gl, Post, Pre | Gl, Post, Pre | Gl, Post, Pre | Gl, Post, Pre | Gl, Post, Pre | Gl, Post, Pre | Gl, Post, Pre | Gl, Post, Pre | Gl, Post, Pre | Gl, Post, Pre | Gl, Post, Pre | Gl, Post, Pre |
| | DN | Gl, Post, P | Gl, Post, P | Gl, Post, P | Gl, Post, P | Gl, Post, P | Gl, Post, P | Gl, Post, P | Gl, Post, P | Gl, Post, P | Gl, Post, P | Gl, Post, P | Gl, Post, P |
| | DO | Gl, Post, P | Gl, Post, P | Gl, Post, P | Gl, Post, P | Gl, Post, P | Gl, Post, P | Gl, Post, P | Gl, Post, P | Gl, Post, P | Gl, Post, P | Gl, Post, P | Gl, Post, P |
| | DP | Gl, Pre, P | Gl, Pre, P | Gl, Pre, P | Gl, Pre, P | Gl, Pre, P | Gl, Pre, P | Gl, Pre, P | Gl, Pre, P | Gl, Pre, P | Gl, Pre, P | Gl, Pre, P | Gl, Pre, P |
| | DQ | Post | Post | Post | Post | Post | Post | Post | Post | Post | Post | Post | Post |
| | DR | Post, Pre | Post, Pre | Post, Pre | Post, Pre | Post, Pre | Post, Pre | Post, Pre | Post, Pre | Post, Pre | Post, Pre | Post, Pre | Post, Pre |
| | DS | Post, P | Post, P | Post, P | Post, P | Post, P | Post, P | Post, P | Post, P | Post, P | Post, P | Post, P | Post, P |
| | DT | Post, Pre, P | Post, Pre, P | Post, Pre, P | Post, Pre, P | Post, Pre, P | Post, Pre, P | Post, Pre, P | Post, Pre, P | Post, Pre, P | Post, Pre, P | Post, Pre, P | Post, Pre, P |
| | DU | Pre | Pre | Pre | Pre | Pre | Pre | Pre | Pre | Pre | Pre | Pre | Pre |

TABLE 3-continued

Treatments and various options provided for managing weeds in exemplary cropping systems I-XII of the present invention. G—glyphosate, Gl—glufosinate, D—dicamba, Pre-a preemergence herbicide, Di-2,4-D, Post-a postemergent herbicide, P—paraquat. A graminicide is not used with corn unless the corn has tolerance to the class of herbicides used for controlling grasses, such as a fops herbicide.

| Treatment & Timing | Options | glyphosate tolerant I | dicamba tolerant II | glufosinate tolerant III | glyphosate and glufosinate tolerant IV | dicamba and glufosinate tolerant V | 2,4-D tolerant VI | glyphosate and dicamba tolerant VII | dicamba and 2,4-D tolerant VIII | glyphosate, dicamba and glufosinate tolerant IX | glyphosate and 2,4-D tolerant X | glyphosate, dicamba and 2,4-D tolerant XI | glyphosate, dicamba, glufosinate and 2,4-D tolerant XII |
|---|---|---|---|---|---|---|---|---|---|---|---|---|---|
| | DV | Pre, P | Pre, P | Pre, P | Pre, P | Pre, P | Pre, P | Pre, P | Pre, P | Pre, P | Pre, P | Pre, P | Pre, P |
| | DW | P | P | P | P | P | P | P | P | P | P | P | P |

G—glyphosate,
Pre-a preemergence herbicide,
D—dicamba,
Gr-a graminicide,
Di-2,4-D, Post-a postemergent herbicide,
P—paraquat.

TABLE 4

Examples of herbicides and rates for use in soybean cropping systems.

| Family | Common name | Trade name | Supplier | Rate/Acre | Maximum a.i./Acre/season |
|---|---|---|---|---|---|
| | | Herbicides suitable for the first treatment | | | |
| EPSPS inhibitors | Glyphosate | Roundup Weathermax | Monsanto | 11-44 oz/A | 7.2875 lbs/A |
| Auxin-like herbicides | Dicamba | Clarity | BASF | 4-24 oz/A | 2 lbs/A |
| | 2,4-D | | | | |
| Acetanilide | alachlor | Intrro | Monsanto | 4-6 pts/A | 3 lbs/A |
| | alachlor | Lasso | Monsanto | 4-6 pts/A | 3 lbs/A |
| | alachlor | Micro Tech | Monsanto | 5-6 pts/A | 3 lbs/A |
| | dimethanamid-P | Establish | Tenkoz | 12-21 oz/A | 0.9844 lbs/A |
| | dimethanamid-P | Outlook | BASF | 12-21 oz/A | 0.9844 lbs/A |
| | flufenacet | Define | Bayer | 8-14 oz/A | 0.4375 lbs/A |
| | metolachlor | Stalwart | Sipcam Agro | 1-2.75 pts/A | 2.75 lbs/A |
| | s-metolachlor | Brawl | Tenkoz | 1-2.6 pt/A | 2.48 lbs/A |
| | s-metolachlor | Dual II Magnum | Syngenta | 1-2.5 pts/A | 2.38 lbs/A |
| ALS | chlorimuron-ethyl | Classic | Dupont | 1.25-3 oz/A | 0.0468 lbs/A |
| | chlorimuron-ethyl + tribenuron-methyl | Canopy EX | Dupont | 1.1-3.3 oz/A | 0.0608 lbs/A |
| | cloransulam-methyl | FirstRate | Dow | 0.6-0.75 oz/A | 0.055125 lb/A |
| | flumetsulam | Python | Dow | 0.8-1.33 oz/A | 0.07 lbs/A |
| | imazaquin | Scepter | BASF | 2.15-2.8 oz/A | 0.245 lbs/A |
| | imazethapyr | Pursuit | BASF | 4 oz/A | 0.063 lbs/A |
| | thifensulfuron + tribenuron + metsulfuron | Affinity | Dupont | 0.6-1.0 oz/A | 0.05625 lb/A |
| | thifensulfuron-methyl | Harmony GT XP | Dupont | 0.083 oz/A | 0.046875 lbs/A |
| ALS + DiNA | imazethapyr + pendimethalin | Pursuit Plus | BASF | 2.5 pts/A | 0.063 lbs/A + 1.48 lbs/A |
| ALS + PPO | chlorimuron-ethyl + sulfentrazone | Canopy XL | Dupont | 2.5-7.0 oz/A | 0.3167 lb/A |
| BLEACHER | clomazone | Command | FMC | 1.33-3.33 pt/A | 1.25 lb/A |
| | norflurazon | Solicam | Syngenta | 1.9-2.5 lbs/A | 1.96 lb/A |
| DiNA | ethalfluralin | Sonilan | Dow | 1.5-3 pts/A | 1.125 lb/A |
| | pendimethalin | Acumen | Tenkoz | 1.2-3.6 pt/A | 1.48 lb/A |
| | pendimethalin | Helena pendimethalin | Helena | 1.2-3.6 pts/A | 1.48 lb/A |
| | pendimethalin | Pendimax | Dow | 1.2-3.6 pts/A | 1.48 lb/A |
| | pendimethalin | Prowl | BASF | 1.2-3.6 pts/A | 1.48 lb/A |
| | pendimethalin | Prowl H2O | BASF | 1.5-3 pts/A | 1.5 lb/A |
| | trifluralin | Bayonet | Helena | 5-10 lbs/A | 1 lb/A |
| | trifluralin | Treflan | Dow | 1-2.5 pts/A | 1.25 lb/A |
| | trifluralin | Trilin | Griffin | 1-2.5 pts/A | 1.25 lb/A |
| Glycine + ALS | glyphosate + imazethapyr | Extreme | BASF | 3 pts/A | 0.56 lbs ae/A glyphosate + 3 lbs + 0.06375 lbs/A imazethapyr |
| PPO | carfentrazone-ethyl | Aim | FMC | 0.5-1.6 oz/A | 0.025 lb/A |
| | flumioxazin | Encompass | Tenkoz | 2-3 oz/A | 0.095625 lb/A |
| | flumioxazin | Valor | Valent | 2-3 oz/A | 0.09562 lbs/A |
| | fomesafen | Flexstar | Syngenta | 0.75-1.5 pt/A | 0.375 lb/A |
| | oxyfluorfen | Galigan | Makhteshim Agan | 0.5-2 pts/A | 0.75 lbs/A |
| | sulfentrazone | Blanket | Tenkoz | 3-8 oz/A | 0.375 lb/A |
| | sulfentrazone | Spartan | FMC | 4.5-12 oz/A | 0.375 lbs/A |
| Triazine | linuron | Linex | Griffin | 1-2 pts/A | 1 lb/A |
| | linuron | Lorox | Griffin | 0.67-2 lbs/A | 1 lb/A |
| | metribuzin | Metribuzin | Makhteshim Agan | 0.33-1.17 lbs/A | 0.8775 lb/A |
| | metribuzin | Metribuzin | AgValue | 0.33-1.17 lbs/A | 0.8775 lb/A |
| | metribuzin | Sencor | Bayer | 0.33-1.17 lbs/A | 0.8775 lbs/A |
| Triazine + Acetanilide | metribuzin + flufenacet | Axiom DF | Bayer | 7-13 oz/A | 0.5525 lb/A |
| Bipyridiliums | Paraquat | Gramoxone Inteon | Syngenta | 8-16 oz/A | 0/75 lb/A |
| | | Herbicides suitable for the second and third treatment | | | |
| ESPS inhibitors | Glyphosate | Roundup Weathermax | Monsanto | 11-44 oz/A | 7.2875 lbs/A |
| GS inhibitors | glufosinate-ammonium | Liberty | Bayer | 28-34 oz/A | 0.809 lbs ai/A |

TABLE 4-continued

Examples of herbicides and rates for use in soybean cropping systems.

| Family | Common name | Trade name | Supplier | Rate/Acre | Maximum a.i./Acre/season |
|---|---|---|---|---|---|
| Auxin-like herbicides | Dicamba | Clarity | BASF | 4-24 oz/A | 2 lbs/A |
|  | 2,4-D |  |  |  |  |
| Acetanilide | s-metolachlor | Dual II Magnum | Syngenta | 1-2.5 pts/A | 2.38 lbs/A |
| ACCase (Graminicides) | clethodim | Trigger | Albaugh | 4-16 oz/A | 0.5 lbs/A |
|  | clethodim | Volunteer | Tenkoz | 4-16 oz/A | 0.5 lbs/A |
|  | clethodim | Select | Valent | 4-16 oz/A | 0.5 lbs/A |
|  | clethodim | Select MAX | Valent | 8-32 oz/A | 0.5 lbs/A |
|  | fluazifop-p-butyl | Fusilade DX | Syngenta | 6-24 oz/A | 0.51 lb/A |
|  | fluazifop-p-butyl + fenoxyprop-p-ethyl | Fusion | Syngenta | 6-12 oz/A | 0.48 lb/A |
|  | quizalofop-ethyl | Assure II | Dupont | 5-12 oz/A | 0.12375 lb/A |
|  | sethoxydim | Poast | BASF | 0.5-2.5 pts/A | 0.9375 lbs/A |
|  | sethoxydim | Poast Herbicide | Micro Flo | 0.5-2.5 pts/A | 0.9375 lbs/A |
| ALS | imazamox | Raptor | BASF | 4-5 oz/A | 0.04 lb ae/A |
|  | imazethapyr | Pursuit | BASF | 4 oz/A | 0.063 lbs/A |
| PPO | acifluorfen | Ultra Blazer | UPI | 0.5-1.5 pt/A | 0.5 lbs/A |
|  | fomesafen | Reflex | Syngenta | 0.75-1.5 pt/A | 0.375 lb/A |
|  | fomesafen | Flexstar | Syngenta | 0.75-1.5 pt/A | 0.375 lb/A |
|  | lactofen | Cobra | Valent | 6-12.5 oz/A | 0.4 lbs/A |
|  | lactofen | Phoenix | Valent | 6-12.5 oz/A | 0.4 lbs/A |
| PSII Site B | bentazon | Basagran | Micro Flo | 1-3 pts/A | 2 lbs/A |
|  | bentazon | Basagran | BASF | 1-3 pts/A | 2 lbs/A |
| Herbicides suitable for the fourth treatment | | | | | |
|  | And/or one or more herbicides suitable for $2^{nd}$ and $3^{rd}$ treatment |  |  |  |  |
| Herbicides suitable for the fifth treatment | | | | | |
| Bipyridiliums | Paraquat Inteon | Gramoxone | Syngenta | 8-16 oz/A | 0/75 lb/A |
|  | And/or one or more herbicides suitable for the Ist treatment |  |  |  |  |

TABLE 5

Examples of herbicides and rates for use in cotton cropping systems. Granular (G), Wettable powders (W or WP), Dry flowable (DF), Water dispersible granules (WDG), Soluble Powder (S), Water soluble (SL), Liquid (L), Aqueous solution (AS), Emulsifiable concentrate (E or EC), Microencapsulated Emulsion (ME), Flowable (F), fluid ounce (fl oz), and pints (pt).

| Family | Chemical | Trade | Supplier | Formulation | Use Rates/Acre of Formulation |
|---|---|---|---|---|---|
| Herbicides suitable for the first treatment | | | | | |
| EPSPS inhibitors | glyphosate | Roundup | Monsanto | 5.5 SL | 11 to 32 fl oz |
| Auxin-like | 2,4-D | Various | Dow | 4 L | 12 to 24 fl oz |
|  | dicamba | Clarity | Syngenta | 4.5 L | 8 fl oz |
| Bipyridiliums | paraquat | Gramoxone | Syngenta | 3 SL | 11 to 21 fl oz |
| DiNA | pendimethalin | Prowl | BASF | 3.3 EC | 1.2 to 3.6 pt |
|  | pendimethalin | Prowl | BASF | 3.3 EC | 1.2 to 2.4 pt |
|  | trifuralin | Treflan | Dow | 4 EC | 1 to 2 pt |
|  | pendimethalin | Prowl | BASF | 3.3 EC | 1.8 to 3.6 pt |
| GS inhibitors | glufosinate-ammonium | Ignite | Bayer | 2.34 L | 22 to 29 fl oz |
| Organoarsenicals | MSMA | Various | Helena | 6 L | 2.67 pt |
| PPO inhibitors | carfentrazone | Aim | FMC | 2 EC | 0.8 to 1.6 fl oz |
|  | flumioxazin | Valor | Valent | 51 WP | 1 to 2 oz |

TABLE 5-continued

Examples of herbicides and rates for use in cotton cropping systems. Granular (G), Wettable powders (W or WP), Dry flowable (DF), Water dispersible granules (WDG), Soluble Powder (S), Water soluble (SL), Liquid (L), Aqueous solution (AS), Emulsifiable concentrate (E or EC), Microencapsulated Emulsion (ME), Flowable (F), fluid ounce (fl oz), and pints (pt).

| Family | Chemical | Trade | Supplier | Formulation | Use Rates/Acre of Formulation |
|---|---|---|---|---|---|
| Pyrimidinylthio-benzoate | pyrithiobac | Staple | DuPont | 85 SP | 0.5 to 1.0 oz |
| Sulfonylurea | thifensulfuron + tribenuron | Harmony Extra | DuPont | 75 WDG | 0.5 oz |
| Triazole | clomazone | Command | FMC | 3 ME | 1.3 to 3.3 pt |
| Ureas and amides | diuron | Direx | Griffin | 4 F | 1.5 to 2 pt |
| | diuron | Direx | DuPont | 4 L | 1.6 to 2 pt |
| | flumeturon | Cotoran | Griffin | 4 F | 2 to 3 pt |
| | Norflurazon | Solicam | Syngenta | DF | 1.25 to 2.5 lb |
| Herbicides suitable for the second and third treatments | | | | | |
| Aryloxyphenoxy propionate | fluazifop p-butyl | Fusilade | Syngenta | 2 EC | 8 to 12 fl oz |
| | quizalofop p-ethyl | Assure | DuPont | 0.88 EC | 7 to 8 fl oz |
| | Fenoxaprop | Whip 360 | Bayer | 0.66 EC | 0.7 to 1 pt |
| Auxin-like | dicamba | Clarity | BASF | 4SL | 8 to 48 fl oz |
| | 2,4-D | Barrage | Helena | 4.7 EC | 1 to 2 pt |
| Bipyridiliums | paraquat | Gramoxone | Syngenta | 3 SL | 13 to 26 fl oz |
| Chloroacetamide | s-metolachlor | Dual | Syngenta | 7.6 EC | 1 to 1.33 pt |
| | s-metolachlor | Dual | Syngenta | 7.6 EC | 1 to 1.33 pt |
| Cyclohexanedione | clethodim | Select | Valent | 2 EC | 6 to 8 fl oz |
| | sethoxydim | Poast | BASF | 1.53 EC | 16 fl oz |
| DiNA | pendimethalin | Prowl | BASF | 3.3 EC | 1.8 to 2.4 pt |
| EPSPS inhibitors | glyphosate | Roundup | Monsanto | 5.5 SL | 22 fl oz |
| GS inhibitors | glufosinate-ammonium | Ignite | Bayer | 2.34 L | 22 to 29 fl oz |
| Organoarsenicals | MSMA | Various | Helena | 6 L | 1 pt |
| | DSMA | Various | Helena | 3.6 L | 1 gal |
| | MSMA | Various | Helena | 6 L | 2.67 pt |
| PPO inhibitors | carfentrazone | Aim | FMC | 2 EC | 0.8 to 1.6 fl oz |
| | flumioxazin | Valor | Valent | 51 WDG | 2 oz |
| | lactofen | Cobra | Valent | 2 EC | 6 to 12 fl oz |
| Protox inhibitors | Oxyflourfen | Goal 2XL | DowAgro | 2EC | 1 to 2 pt |
| PS II inhibitors | prometryn | Caparol | Syngenta | 4 F | 1.3 to 2.4 pt |
| Pyrimidinylthio-benzoate | pyrithiobac | Staple | DuPont | 85 SP | 1.2 oz |
| Sulfonylurea | trifloxysulfuron-sodium | Envoke | Syngenta | 75 WDG | 0.1 oz |
| Ureas and amides | fluometuron | Cotoran | Griffin | 4 L | 2 to 3.2 pt |
| | diuron | Direx | Griffin | 4 L | 1.6 to 2.4 pt |
| | linuron | Linex | Griffin | 4 L | 2 pt |
| Herbicides suitable for the fourth treatment | | | | | |
| EPSPS inhibitors | glyphosate | Roundup | Monsanto | 5.5 SL | 16 to 22 fl oz |
| Auxin-like | dicamba | Clarity | BASF | 4SL | 8 to 48 fl oz |
| | 2,4-D | Barrage | Helena | 4.7 EC | 1 to 2 pt |
| Defoliant | dimethipin | Harvade | Chemtura | 5 F | 8 to 10 fl oz |
| GS inhibitors | glufosinate-ammonium | Ignite | Bayer | 2.34 L | 22 to 29 fl oz |
| PPO | carfentrazone-ethyl | Aim | FMC | 2 EC | 1 to 1.5 fl oz |
| Herbicides suitable for the fifth treatment | | | | | |
| Bipyridiliums One or more herbicides suitable for the first treatment | paraquat | Gramoxone | Syngenta | 2.5 L | 2.5 to 4.0 pt |

TABLE 6

Exemplary pre-emergence and post-emergence herbicides and combinations for use with dicamba on corn in cropping systems of the present invention. Pre-emergence includes the first and/or fifth treatment. Post-emergence includes the second, third, fourth treatments, and/or fifth treatment.

| Chemical Family | Common name | Trade Name | Pre- or Post-emergent treatment |
|---|---|---|---|
| Chloroacetamides-acetanilides | Acetochlor Metolachlor/ S-metolachlor Alachlor | Dual Magnum | Pre (can also be used Post) |
| Triazines | Atrazine Simazine | | Pre and Post |
| 4HPPD | Isoxazoles + mesotrione mesotrione | CONVERGE Callisto | Pre |
| ALS/Growth Regulator | Flumetsulam Clopyralid Clopyralid + Flumetsulam | Python Stinger Hornet | Pre |
| Dinitroanilines | Pendimethalin | Prowl | Pre |
| EPSPS inhibitor | Glyphosate | Roundup | Post |
| ALS | Sulfonylureas (Rimsulfuron, nicosulfuron) & Imidazolinones (imazethapyr) | Accent Lightning (can also be applied pre) | Post |
| Phosphonic acid | Glufosinate | Liberty | Post |
| Semicarbazones | Diflufenzopyr | Distinct (+dicamba) | Post |
| 4-HPPD | Mesotrione + Isoxazole | Callisto Balance | Post |
| Triazine | atrazine | | Post |
| Auxins: | | | Post |
| Phenoxyacetic acids | 2,4-D | | |
| Pyridine carboxylic acids | clopyralid | Lontrel, Stinger | |
| PS2 inhibitors | | | Post |
| Nitriles | Bromoxynil | Buctril, Pardner | |
| benzothiadiazinones | Bentazon | Basagran | |
| PPO's | | | Post |
| N-phenylphthalamides | Flumiclorac | Resource | |
| Triazolinones | Carfentrazone | Aim EW | |

Example 2

A Method for Minimizing the Development of Herbicide Resistant Weeds

As shown in Table 7, a method for minimizing the development of a herbicide resistant weed population is exemplified by rotating a first cropping system (I to XII; Table 3) in a first year comprising a crop tolerant to one or more low-risk herbicides and accompanying herbicidal treatments with a second cropping system (I to XII; Table 3) in a second year comprising a crop tolerant to one or more low-risk herbicides and accompanying herbicidal treatments. For example, if the crop in the first cropping system is tolerant to glyphosate then the crop in the second cropping system can be tolerant to an auxin like herbicide or tolerant to glyphosate and an auxin like herbicides. Herbicide rates are given in Table 4 and Table 5 for soybean and cotton, respectively. Equipments and methods known in the art are used for applying various herbicide treatments.

TABLE 7

Examples of methods for minimizing the development of herbicide resistant weeds by rotating a first cropping system with a second cropping system.

| | | \multicolumn{12}{c}{Second Cropping System Options} |
|---|---|---|---|---|---|---|---|---|---|---|---|---|---|

| | | I | II | III | IV | V | VI | VII | VIII | IX | X | XI | XII |
|---|---|---|---|---|---|---|---|---|---|---|---|---|---|
| First Cropping System Options | I | | X | X | X | X | X | X | X | X | X | X | X |
| | II | X | | X | X | X | X | X | X | X | X | X | X |
| | III | X | X | | X | X | X | X | X | X | X | X | X |
| | IV | X | X | X | | X | X | X | X | X | X | X | X |
| | V | X | X | X | X | | X | X | X | X | X | X | X |
| | VI | X | X | X | X | X | | X | X | X | X | X | X |
| | VII | X | X | X | X | X | X | | X | X | X | X | X |
| | VIII | X | X | X | X | X | X | X | | X | X | X | X |
| | IX | X | X | X | X | X | X | X | X | | X | X | X |
| | X | X | X | X | X | X | X | X | X | X | | X | X |
| | XI | X | X | X | X | X | X | X | X | X | X | | X |
| | XII | X | X | X | X | X | X | X | X | X | X | X | |

Example 3

Production of Transgenic Soybean Having Dicamba and Glyphosate Tolerances for Use in Cropping Systems for Manging Weeds Methods for producing transgenic seeds having glyphosate tolerance are known in the art and such seeds can be produced by persons of skill in the art by using a polynucleotide encoding glyphosate resistant 5-enolpyruvylshikimate-3-phosphate synthase (EPSPS) as described in U.S. Pat. No. 5,627,061, U.S. Pat. No. RE39,247, U.S. Pat. No. 6,040,497 and in U.S. Pat. No. 5,094,945, WO04074443 and WO04009761, all of which are hereby incorporated by reference. Soybean breeding lines containing the Roundup Ready® trait event 40-3-2 (Padgette et al., 1995) have been produced. Seeds from soybean plant designated as MON19788 have been deposited under ATCC Accession No. PTA-6708.

Glyphosate tolerant plants can also be produced by incorporating polynucleotides encoding glyphosate degrading enzymes such as glyphosate oxidoreductase (GOX, U.S. Pat. No. 5,463,175, herein incorporated by reference), a glyphosate-N-acetyl transferase (GAT, U.S. Patent Publ. 20030083480, herein incorporated by reference), and a glyphosate decarboxylase (WO05003362; US Patent Application 20040177399, herein incoroporated by reference).

Dicamba tolerant soybean plants have been described in U.S. provisional application Ser. No. 60/811,276, filed Jun. 6, 2006. A suitable line from each was crossed and progeny seeds were screened with herbicide applications of glyphosate and dicamba to obtain progeny expressing both genes and exhibiting tolerance to both dicamba and glyphosate. Alternatively, coding sequences conferring tolerance to one or both of the herbicides can be directly introduced into a given line.

Transgenic seeds having dicamba and glyphosate tolerances were tested for their tolerance to dicamba, glyphosate, or both herbicides. Table 8 shows tolerance of transgenic soybeans carrying glyphosate and dicamba tolerance transgenes to glyphosate, dicamba, and glyphosate and dicamba at various stages of plant growth. Injury was not seen on plants when either or both herbicides were applied at pre-emergence stage. Post-emergence treatments of either or both herbicides at V3, R1, and R3-4 showed only little injury.

TABLE 8

Tolerance of transgenic soybeans carrying glyphosate and dicamba tolerance transgenes to glyphosate, dicamba, and glyphosate and dicamba.

| Plant Line | Herbicide Applied | Rate gm ae/ha | Pre-emergence treatment 20 DAT | Post-emergence treatment | | |
|---|---|---|---|---|---|---|
| | | | | V3 8 DAT | R1 7 DAT | R3-4 18 DAT |
| | | | | % injury (Average of 4 replications) | | |
| Non-transgenic Control | CLARITY | 561 | 99.0 | 83.8 | 71.3 | 85.0 |
| | RWMax | 841 | 0.0 | 81.3 | 66.3 | 67.5 |
| | CLARITY + RWMax | 561 + 841 | 99.5 | 93.8 | 81.3 | 99.0 |
| RR1 + DMO Line1 | CLARITY | 561 | 0.0 | 7.0 | 6.3 | 4.5 |
| | RWMax | 841 | 0.0 | 3.5 | 3.5 | 11.3 |
| | CLARITY + RWMax | 561 + 841 | 0.0 | 3.0 | 4.0 | 10.0 |
| RR1 + DMO Line 2 | CLARITY | 561 | 0.0 | 5.3 | 6.3 | 5.3 |
| | RWMax | 841 | 0.0 | 4.5 | 4.5 | 11.7 |
| | CLARITY + RWMax | 561 + 841 | 0.0 | 5.0 | 4.0 | 8.8 |
| RR1 + DMO Line 3 | CLARITY | 561 | 0.0 | 9.0 | 8.8 | 7.5 |
| | RWMax | 841 | 0.0 | 3.5 | 4.0 | 11.3 |
| | CLARITY + RWMax | 561 + 841 | 0.0 | 4.5 | 3.5 | 10.0 |
| RR1 + DMO Line 4 | CLARITY | 561 | 0.0 | 8.5 | 8.8 | 3.5 |
| | RWMax | 841 | 0.0 | 3.5 | 3.5 | 11.3 |
| | CLARITY + RWMax | 561 + 841 | 0.0 | 4.5 | 4.5 | 8.8 |
| RR2 + DMO Line1 | CLARITY | 561 | 0.0 | 8.5 | 6.3 | 5.3 |
| | RWMax | 841 | 0.0 | 3.5 | 3.5 | 3.0 |
| | CLARITY + RWMax | 561 + 841 | 0.0 | 5.0 | 4.5 | 5.0 |
| RR2 + DMO Line 2 | CLARITY | 561 | 0.0 | 9.0 | 6.3 | 3.0 |
| | RWMax | 841 | 0.0 | 3.5 | 6.3 | 3.0 |
| | CLARITY + RWMax | 561 + 841 | 0.0 | 9.5 | 7.0 | 3.0 |
| RR2 + DMO Line 3 | CLARITY | 561 | 0.0 | 9.5 | 7.5 | 3.5 |
| | RWMax | 841 | 0.0 | 3.5 | 6.3 | 4.5 |
| | CLARITY + RWMax | 561 + 841 | 0.0 | 8.5 | 3.5 | 3.3 |
| RR2 + DMO Line 4 | CLARITY | 561 | 0.0 | 5.3 | 5.8 | 3.0 |
| | RWMax | 841 | 0.0 | 16.5 | 17.0 | 4.0 |
| | CLARITY + RWMax | 561 + 841 | 0.0 | 11.0 | 3.5 | 5.3 |

Example 4

Production of Transgenic Soybean Having Dicamba and Glufosinate Tolerances for Use in Cropping Systems for Managing Weeds Soybean transgenic event 469-13-19 carrying a transgene for dicamba tolerance and glufosinate tolerance was produced by transforming soybean according to Zhang et al. (1999) with a plant transformation vector carrying a gene encoding DMO, and a gene for phosphinothricin acetyltransferase. The transgenic plants were grown and sprayed with either CLARITY (dicamba) and LIBERTY (glufosinate) herbicides alone or both as a tank mixture at an application rate of 561 g/ha (0.5 lb/a) as a postemergence treatment at V3 and evaluated for tolerance. The results shown in the Table 9 indicate that transgenic plants carrying a transgene for both glufosinate and dicamba are tolerant to either or both herbicides.

TABLE 9

Transgenic soybean carrying a transgene for both glufosinate and dicamba shows tolerance to either or both herbicides.

| Treatment | Rate gm ae/ha | % injury (15 DAT) (Mean of 6 replications) |
|---|---|---|
| UNTREATED CHECK NE3001 | 0 | 0.0 |
| LIBERTY | 561 | 98.3 |
| CLARITY | 561 | 88.3 |
| LIBERTY | 561 | |
| CLARITY | 561 | 98.3 |
| UNTREATED CHECK 469-13-19 | 0 | 0.0 |
| LIBERTY | 561 | 19.2 |
| CLARITY | 561 | 2.7 |
| LIBERTY | 561 | 25.0 |
| CLARITY | 561 | |

Example 5

Production of Transgenic Soybean Having Dicamba, Glufosinate, and Glyphosate Tolerances for Use in Cropping Systems for Managing Weeds A soybean transformation event comprising transgenes for dicamba tolerance and glufosinate tolerance was produced by transforming soybean according to Zhang et al. (1999) with a plant transformation vector carrying a gene encoding DMO, and a gene for phosphinothricin acetyltransferase. A soybean plant comprising this event was crossed with a soybean plant comprising a transgenic event produced as above carrying a gene specifying tolerance to glyphosate. Plants comprising transgenic event (A19788) and carrying genes for tolerance to all three herbicides were tested for their tolerance to these herbicides, applied individually and in combination. A wild type soybeans control (A3525, Asgrow) showed 80-83% injury at 14 DAT with Clarity and RWMax (Roundup WeatherMAX), whereas Liberty and various tank mix combinations of three herbicides caused greater than 95% injury. The transgenic event showed less than 5% injury for Clarity, RWMax, or Clarity+RWMax treatment. Injury was between 15% and 18% for Liberty, Liberty+Clarity, or Liberty+Clarity+RWMax treatment.

Example 6

Use of Transgenic Soybean Having Dicamba and Glyphosate Tolerance in Cropping Systems In this example, use of dicamba and glyphosate tolerant soybean in managing glyphosate tolerant or resistant weeds is demonstrated. Transgenic seeds are planted using a four row planter in 30" rows in a field infested naturally with weeds disclosed below. The plots are 25 feet long and replicated 3 times with the center two rows sprayed and the outside rows left as running checks (unsprayed, used to rate weed control). The plots are rated for pre-emergence weed control compared to the ROUNDUP only plot. The plots are rated for post-emergence weed control compared to the running check 21 days after each post-emergence application. Injury to the transgenic soybean is rated 7 days after each post-emergence treatment. Plots are subjected to the treatments specified in Table 10. Treatments 11 through 14 are varied depending upon the target weed species. POSTin treatment 11 and 12 refers to application on 3" weeds and POST in treatment 13, 14 refers to application on 6" weeds.

Herbicide rates are as follows unless otherwise noted in Table 10: Roundup (Rup; Roundup WeatherMAX): 1.12 lbs ae/A; Clarity: 16 oz/A; INTRRO: 2 qts/A; Authority First: 3 oz/A; FirstRate: 0.3 oz/A; Scepter: 2.8 oz/A; Classic: 1.25 oz/A; Boundary: 2.1 pints/A; Valor: 2 oz/A; Gangster: 1.8 oz/A; Synchrony XP: 0.375 oz/A; Pursuit: 4 oz/A; Flexstar: 12 oz/A; Prowl H2O: 2 pts/A; Cobra 12.5: oz/A; Raptor: 4 oz/A. AMS at 2% w/w added to all treatments containing Roundup. 3 WAT is 3 weeks after treatment.

TABLE 10

Herbicide application regimes.

| PRE | Early POST (usually on 6" weed) | Late POST (V5 to R1) |
|---|---|---|
| 1) Roundup | Roundup on 6" weeds | Roundup (3 WAT) |
| 2) Roundup | Roundup + Clarity 3" weeds | Roundup + Clarity |
| 3) Roundup | Roundup + Clarity 6" weeds | Roundup + Clarity |
| 4) Roundup | Roundup + 4 oz Clarity 3" weeds | Roundup + Clarity |
| 5) Roundup | Roundup + 4 oz Clarity 6" weeds | Roundup + Clarity |
| 6) Roundup + Clarity | Roundup | Roundup |
| 7) Roundup + Clarity | Roundup + Clarity | Roundup |
| 8) Roundup + Clarity | Roundup + Clarity | Roundup + Clarity |
| 9) Roundup + Clarity | Roundup | Rup1.5 + Clarity1.5 |
| 10) Rup + Authority First | Roundup | Roundup |
| 11) Treatment to determine if weeds are resistant to ALS inhibiting herbicides | | |
| 12) Current commercial standard | | |
| 13) Treatment 1 | | |
| 14) Treatment 2 | | |

If the weed is a Palmer pigweed or waterhemp then treatments 11-14 are as follows: 11) Roundup+Classic PRE fb Pursuit POST; 12) Roundup+Valor+2,4-D PRE fb Roundup+ Cobra POST; 13) Roundup+INTRRO PRE fb Roundup+ Clarity POST; 14) Roundup+Prowl H2O PRE fb Roundup+ Clarity POST.

If the weed is a common or giant ragweed then treatments 11-14 are as follows: 11) Roundup+Scepter PRE fb FirstRate POST; 12) Roundup+FirstRate PRE fb Roundup+Flexstar POST; 13) Roundup+FirstRate PRE fb Roundup+Clarity POST; 14) Roundup+Boundary PRE fb Roundup+Clarity POST.

If the weed is lambsquarters or morningglory then treatments 11-14 are as follows: 11) Roundup+Scepter PRE fb Synchrony XP POST; 2) Roundup+FirstRate PRE fb Roundup+Raptor POST; 13) Roundup+Valor PRE fb Roundup+Clarity POST; 14) Roundup+Gangster PRE fb Roundup+Clarity POST.

If the weed is marestail then treatments 11-14 are as follows: 11) Roundup+Classic PRE fb FirstRate POST; 12) Roundup+Valor+2,4-D PRE fb Roundup+FirstRate POST; 13) Roundup+Boundary+2,4-D PRE fb Roundup+Clarity POST; 14) Roundup+Gangster+2,4-D PRE fb Roundup+Clarity POST.

It is expected that target weeds that are known to be resistant to glyphosate will not be controlled well by glyphosate alone. A mixture of glyphosate and dicamba is expected to provide good control of broadleaf weeds that are resistant to glyphosate. Treatments that include a pre-emergence herbicide at planting and a mixture of glyphosate and dicamba post-emergence is expected to provide good control of glyphosate resistant broadleaf weeds.

Example 7

Use of Dicamba for Treatment of Glyphosate-Resistant and Hard to Control Weed Populations In this example, use of dicamba tolerance in managing weeds is demonstrated. Herbicide treatments are applied to homogeneous well drained fields, preferably no till fields, having a uniform population of weeds such as glyphosate resistant broadleaf weeds and other tough-to-control broadleaf weeds such as pigweed sp., morningglory sp., *sesbania*, sicklepod, prickly sida using a randomized complete block design (RCBD) format with 3 replications in several locations. The following treatments at the rate indicated are applied prior to the emergence of the weeds. Weed control rating by each species (i.e., % of control) are taken at 7 and 21 days after application to determine weed control.

TABLE 11

Treatments for control of weed populations.

| | Treatment | Rate (lb/Ac) |
|---|---|---|
| 1 | Clarity | 0.25 |
| 2 | Clarity | 0.5 |
| 3 | Clarity | 0.75 |
| 4 | Clarity | 1.0 |
| 5 | Acetochlor | 1.5 |
| 6 | Clarity + Acetochlor | 0.25 + 1.5 |
| 7 | Clarity + Acetochlor | 0.5 + 1.5 |
| 8 | pendimethalin | 0.825 |
| 9 | Clarity + pendimethalin | 0.25 + 0.825 |
| 10 | Clarity + pendimethalin | 0.5 + 0.825 |
| 11 | Reflex | 0.25 |
| 12 | Clarity + Reflex | 0.25 + 0.25 |
| 13 | Clarity + Reflex | 0.5 + 0.25 |
| 14 | Untreated | |

Treatments as shown below in Table 12 may be applied after weed emergence in fields having populations of target weeds such as glyphosate resistant broadleaf weeds and other tough-to-control broadleaf weeds such as pigweed sp., morningglory sp., *sesbania*, sicklepod, prickly sida in an RCBD format with 3-4 replications in several locations. The following treatments at the rate indicated are applied when weeds are 4-8 inches tall. Weed control rating by each species (i.e., % of control) at 10 and 21 DAT is noted to estimate post emergence burndown of existing weeds and to determine length of residual control.

TABLE 12

Additional exemplary herbicide treatment regimes for hard to control weeds.

| | Treatments | Rate (lb/A) |
|---|---|---|
| 1 | Clarity | 0.125 |
| 2 | Clarity | 0.25 |
| 3 | Clarity | 0.5 |
| 4 | Clarity + | 0.25 |
| | Roundup WeatherMax | 0.56 |
| 5 | Clarity + | 0.25 |
| | Roundup WeatherMax | 0.75 |
| 6 | Clarity + | 0.25 |
| | Roundup WeatherMax | 1.12 |
| 7 | Clarity + | 0.5 |
| | Roundup WeatherMax | 0.75 |
| 8 | Clarity + | 0.25 |
| | Ignite | 0.31 |
| 9 | Clarity + | 0.25 |
| | Ignite | 0.42 |
| 10 | Clarity + | 0.25 |
| | Ignite | 0.53 |
| 11 | Roundup WeatherMax + | 0.75 |
| | Ignite | 0.21 |
| 12 | Roundup WeatherMax + | 0.375 |
| | Ignite | 0.42 |
| 13 | Roundup WeatherMax + | 0.75 |
| | Ignite | 0.42 |
| 14 | Roundup WeatherMax + | 0.75 |
| | Ignite + | 0.42 |
| | Clarity | 0.25 |
| 15 | Nontreated | |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,554,101; U.S. Pat. No. 4,581,847; U.S. Pat. No. 4,761,373; U.S. Pat. No. 4,810,648; U.S. Pat. No. 5,004,863; U.S. Pat. No. 5,013,659; U.S. Pat. No. 5,015,580; U.S. Pat. No. 5,094,945; U.S. Pat. No. 5,141,870; U.S. Pat. No. 5,159,135; U.S. Pat. No. 5,273,894; U.S. Pat. No. 5,276,268; U.S. Pat. No. 5,322,938; U.S. Pat. No. 5,322,938; U.S. Pat. No. 5,352,605; U.S. Pat. No. 5,352,605; U.S. Pat. No. 5,359,142; U.S. Pat. No. 5,359,142; U.S. Pat. No. 5,362,865; U.S. Pat. No. 5,362,865; U.S. Pat. No. 5,378,

619; U.S. Pat. No. 5,378,824; U.S. Pat. No. 5,384,253; U.S. Pat. No. 5,445,962; U.S. Pat. No. 5,463,175; U.S. Pat. No. 5,508,184; U.S. Pat. No. 5,530,196; U.S. Pat. No. 5,530,196; U.S. Pat. No. 5,538,880; U.S. Pat. No. 5,550,318; U.S. Pat. No. 5,561,236; U.S. Pat. No. 5,591,616; U.S. Pat. No. 5,597,717; U.S. Pat. No. 5,605,011; U.S. Pat. No. 5,627,061; U.S. Pat. No. RE39,247; U.S. Pat. No. 5,633,437; U.S. Pat. No. 5,633,444; U.S. Pat. No. 5,635,055; U.S. Pat. No. 5,637,489; U.S. Pat. No. 5,641,876; U.S. Pat. No. 5,646,024; U.S. Pat. No. 5,659,122; U.S. Pat. No. 5,719,046; U.S. Pat. No. 5,728,925; U.S. Pat. No. 5,750,871; U.S. Pat. No. 5,767,366; U.S. Pat. No. 5,824,877; U.S. Pat. No. 5,846,797; U.S. Pat. No. 5,850,019; U.S. Pat. No. 5,939,602; U.S. Pat. No. 5,981,840; U.S. Pat. No. 6,040,497; U.S. Pat. No. 6,051,753; U.S. Pat. No. 6,140,078; U.S. Pat. No. 6,160,208; U.S. Pat. No. 6,175,060; U.S. Pat. No. 6,177,611; U.S. Pat. No. 6,225,105; U.S. Pat. No. 6,232,526; U.S. Pat. No. 6,252,138; U.S. Pat. No. 6,268,549; U.S. Pat. No. 6,294,714; U.S. Pat. No. 6,376,754; U.S. Pat. No. 6,384,301; U.S. Pat. No. 6,384,301; U.S. Pat. No. 6,388,170; U.S. Pat. No. 6,399,861; U.S. Pat. No. 6,403,865; U.S. Pat. No. 6,414,222; U.S. Pat. No. 6,426,446; U.S. Pat. No. 6,429,357; U.S. Pat. No. 6,429,362; U.S. Pat. No. 6,433,252; U.S. Pat. No. 6,437,217; U.S. Pat. No. 6,586,367; U.S. Pat. No. 6,613,963; U.S. Pat. No. 6,624,344; U.S. Pat. No. 6,635,806; U.S. Pat. No. 6,677,503; U.S. Pat. No. 7,022,896; U.S. Pat. No. 7,060,876.
U.S. Patent Publn. 20030115626; U.S. Patent Publn. 20030135879; U.S. Patent Publn. 20040177399; U.S. Patent Publn. 20030083480; U.S. Patent Publn. 20070079393.
U.S. Patent application Ser. No. 09/757,089; U.S. Prov. Patent Applic. Ser. No. 60/811,276; U.S. Provisional Appln. Ser. No. 60/891,675.
Bevan et al., *Nature*, 304:184-187, 1983.
Carrington and Freed, *J. of Virology* 64:1590-1597, 1990.
Chandler et al., *Plant Cell*, 1:1175-1183, 1989.
Chandler, In: *CRC Handbook of Pest Management in Agriculture*, Pimentel (Ed.), 1:95-109, 1981.
Comai et al., *Nature*, 317:741, 1985.
Cork and Khalil, *Adv. Appl. Microbiol.*, 40:289-321, 1995.
Cork and Krueger, *Adv. Appl. Microbiol.*, 36:1-66, 1991.
Coruzzi et al., *EMBO J.*, 3: 1671, 1984.
Creissen et al., *Plant J.*, 8(2):167-175, 1995.
Crop Protection Chemicals Reference, Chemical & Pharmaceutical Press, Inc., NY, 11$^{th}$ Ed., 1803-1821, 1995
De Block et al., *EMBO J.*, 6(9):2513-2518, 1987.
della-Cioppa et al., *Proc. Natl. Acad. Sci. USA*, 83:6873-6877, 1986.

Depicker et al., *J. Mol. Appl. Genet.* 1:561-573, 1982.
Ebert et al., *Proc. Natl. Acad. Sci. USA*, 84:5745-5749, 1987.
European Patent Appln. 275,957
Fraley et al., *Proc. Natl. Acad. Sci. USA*, 80:4803-4807, 1983.
Herbicide Handbook, In: *Weed Science Society of America*, 8th Ed., Vencill (Ed.), 2002.
Herman et al., *J. Biol. Chem.*, 280:24759-24767, 2005.
Hirschberg et al., *Science*, 222:1346-1349, 1983.
Ingelbrecht et al., *Plant Cell*, 1:671-680, 1989.
Japanese Patent Appln. 06343473
Klee et al., *Mol. Gen. Genet.*, 210:437-442, 1987.
Kyte and Doolittle, *J. Mol. Biol.*, 157(1):105-132, 1982.
Lawton et al., *Plant Mol. Biol.* 9:315-324, 1987.
Légère et al., *Weed Technol.* 20:485-493, 2006.
Mallory-Smith and Retzinger Jr., *Weed Technology*, 17:605-619, 2003.
Mazur, et al., *Nucleic Acids Res.*, 13(7):2373-2386, 1985.
McWilliams et al., *Soybean Growth and Management Quick Guide*, North Dakota State Univ. Extension Publ. A-1174, 1999.
Miki et al., In: *Methods in Plant Molecular Biology and Biotechnology*, Glick and Thompson (Eds.), CRC Press, 67-88, 1993.
Odell et al., *Nature*, 313:810-812, 1985.
PCT Appln. WO07/053,482; PCT Appln. WO 04/009761; PCT Appln. WO 04/074443; PCT Appln. WO 05/003362; PCT Appln. WO 05/107437; PCT Appln. WO 87/04181; PCT Appln. WO 89/00193; PCT Appln. WO 89/11789; PCT Appln. WO 96/38567; PCT Appln. WO 97/41228; PCT Appln. WO95/06722.
Schmidt, In *HRAC Classification of Herbicides according to Mode of Action*, Brighton Crop Protection Conference— Weeds 1133-1140, 1997.
Stalker et al., *Science*, 242:419, 1988.
Streber and Willmitzer, *Bio/Technology*, 7:811, 1989.
Turner and Foster, *Molecular Biotech.*, 3:225, 1995. Becker et al., *Plant Mol. Biol.*, 20(1):49-60, 1992.
VanGessel and Majek, In: *Soybean Weed Management Guide: for Delaware and New Jersey*, University of Delaware and Rutgers University, 2005.
Walker et al., *Proc. Natl. Acad. Sci. USA*, 84:6624, 1987.
Wang et al., *Appl. Env. Microbiol.* 63:1623-1626, 1997.
Wang, In: *Characterization of Cellular and Enzymatic Degradation of Dicamba by Pseudomonas maltophilia, Strain DI-6*, Ph.D. Thesis, University of Nebraska-Lincoln, 1996.
Yang and Russell, *Proc. Natl. Acad. Sci. USA*, 87:4144-4148, 1990.
Zhang et al. *Plant Cell, Tissue and Organ Culture* 56: 37-46, 1999.

What is claimed is:

1. A cropping system for managing weed growth in a crop-growing environment comprising:
   a) planting in a crop growing environment a crop seed that germinates into a crop plant comprising tolerance to a benzoic acid herbicide; and
   b) applying at least a first herbicide treatment to the crop growing environment to control weed growth, wherein the herbicide treatment is selected from the group consisting of the first, second, third, fourth and fifth treatment set forth in Table 3, wherein the treatment comprises an amount of herbicide effective to control weed growth without significantly damaging the crop seed or crop plant, and wherein at least one herbicide treatment is applied which comprises an herbicidally effective amount of a benzoic acid herbicide selected from the group consisting of the first, second, third, and fourth treatment set forth in Table 3.

2. The system of claim 1, further comprising applying at least two of said herbicide treatments.

3. The system of claim 1, further comprising applying at least three of said herbicide treatments.

4. The system of claim 1, further comprising applying at least four of said herbicide treatments.

5. The system of claim 1, further comprising applying each of said herbicide treatments.

6. The system of claim 1, wherein the plant further comprises a transgene conferring herbicide tolerance to glyphosate or glufosinate.

7. The system of claim 6, wherein the transgene conferring herbicide tolerance to glyphosate encodes a polypeptide selected from the group consisting of glyphosate resistant 5-enolpyruvylshikimate-3-phosphate synthase (EPSPS), glyphosate oxidoreductase (GOX), glyphosate-N-acetyl transferase (GAT) and glyphosate decarboxylase.

8. The system of claim 7, wherein the plant comprises a glyphosate-N-acetyl transferase (GAT) polypeptide.

9. The system of claim 8, wherein the GAT polypeptide comprises SEQ ID NO:2.

10. The system of claim 6, wherein herbicide tolerance to glufosinate is provided by a gene encoding phosphinothricin acetyltransferase.

11. The system of claim 1, wherein the crop plant comprising tolerance to a benzoic acid herbicide comprises a transgene encoding DMO.

12. The system of claim 1 or 6, defined as comprising the step of applying a second herbicide treatment at the early post-emergence stage comprising a herbicidally effective amount of a herbicide selected from the group consisting of glyphosate, an auxin-like herbicide, glufosinate, a graminicide, a post-emergent selective herbicide, and a combination thereof.

13. The system of claim 1 or 6, defined as comprising the step of applying a third herbicide treatment at the late post-emergence stage comprising a herbicidally effective amount of a herbicide selected from the group consisting of glyphosate, an auxin-like herbicide, glufosinate, a graminicide, a post-emergent selective herbicide, and a combination thereof.

14. The system of claim 1, defined as comprising the step of applying a fourth herbicide treatment at the pre-harvest stage comprising a herbicidally effective amount of a herbicide selected from the group consisting of glyphosate, an auxin-like herbicide, glufosinate, a post-emergent selective herbicide, and a combination thereof.

15. The system of claim 14, further comprising the step of harvesting the seeds from the crop plant after fourth treatment.

16. The system of claim 15, further comprising the step of applying a fifth herbicide treatment at the post-harvest stage comprising a herbicidally effective amount of a herbicide selected from the group consisting of glyphosate, an auxin-like herbicide, glufosinate, paraquat, a pre-emergent selective herbicide, a post emergent selective herbicide, and a combination thereof.

17. The system of claim 1, wherein benzoic acid herbicide is selected from the group consisting of dicamba, tricamba, and chloramben, and a combination thereof.

18. The system of claim 1, wherein the crop plant is a dicot plant.

19. The system of claim 18, wherein the crop plant is soybean.

20. The system of claim 19, wherein the at least a first herbicide treatment comprises an active ingredient selected from the group consisting of: glyphosate, 2,4-D, chlorimuron-ethyl, clethodim, fluazifop P-butyl, flumioxazin, fomesafen, imazethapyr, metribuzin, glufosinate, dicamba, and pendimethalin.

21. The system of claim 19, wherein the amount of herbicide comprises an amount set forth in Table 4 for the respective herbicide(s).

22. The system of claim 18, wherein the crop plant is cotton.

23. The system of claim 22, wherein the at least a first herbicide treatment comprises an active ingredient selected from the group consisting of: glyphosate, 2,4-D, carfentrazone-ethyl, trifloxysulfuron, diuron, fluometuron, MSMA, prometryn, pyrithiobac-sodium, metolachlor, acetochlor, fomesafen, flumioxazin, sethoxydim, glufosinate, dicamba, and pendimethalin.

24. The system of claim 22, wherein the amount of herbicide comprises an amount set forth in Table 5 for the respective herbicide(s).

25. The system of claim 1, wherein the crop plant is a monocot plant.

26. The system of claim 25, wherein the crop plant is corn.

27. The system of claim 26 wherein the at least a first herbicide treatment comprises an active ingredient selected from the group consisting of a chloroacetamide herbicide, a triazine herbicide, a 4HPPD herbicide, an ALS/Growth Regulator herbicide, a dinitroaniline herbicide, an EPSPS inhibitor, an ALS herbicide, a Phosphonic acid herbicide, a semicarbazone, an auxin-like herbicide, a Phenoxyacetic acid herbicide, a Pyridine carboxylic acid herbicide, a PS2 inhibitor, a nitrile, a benzothiadiazinone, a PPO, a N-phenylphthalamides, and a triazolinone.

28. The system of claim 19 or claim 22, further comprising the step of applying a third herbicide treatment at the late post-emergence stage comprising a herbicidally effective amount of a herbicide selected from the group consisting of glyphosate, an auxin-like herbicide, a graminicide, a post-emergent selective herbicide, and a combination thereof.

29. The system of claim 28, further comprising the step of applying a fourth herbicide treatment at the pre-harvest stage comprising a herbicidally effective amount of a herbicide selected from the group consisting of glyphosate, an auxin-like herbicide, a post-emergent selective herbicide, and a combination thereof.

30. The system of claim 29, further comprising the step of harvesting the seeds from the crop plant after a fourth treatment.

31. The system of claim 19 or claim 22, wherein the benzoic acid herbicide is selected from the group consisting of dicamba, tricamba, and chloramben, and a combination thereof.

32. The cropping system of claim 1, wherein the herbicide treatment controls the growth of a herbicide resistant weed selected from the group consisting of: *Alopecurus myosuroides, Avena fatua, Avena sterilis, Avena sterilis ludoviciana, Brachiaria plantaginea, Bromus diandrus, Bromus rigidus, Cynosurus echinatus, Digitaria ciliaris, Digitaria ischaemum, Digitaria sanguinalis, Echinochloa colona, Echinochloa crus-galli, Echinochloa oryzicola, Echinochloa phyllopogon, Eleusine indica, Eriochloa punctata, Hordeum glaucum, Hordeum leporinum, Ischaemum rugosum, Leptochloa chinensis, Lolium multiflorum, Lolium perenne, Lolium persicum, Lolium rigidum, Phalaris minor, Phalaris paradoxa, Rottboellia exalta, Setaria faberi, Setaria viridis, Setaria viridis var, robusta-alba schreiber, Setaria viridis var, robusta-purpurea, Snowdenia polystachea, Sorghum halepense, Sorghum sudanese, Alisma plantago-aquatica, Amaranthus blitoides, Amaranthus hybridus, Amaranthus lividus, Amaranthus palmeri, Amaranthus powellii, Amaranthus quitensis, Amaranthus retroflexus, Amaranthus rudis, Amaranthus tuberculatus, Ambrosia artemisiifolia, Ambrosia trifida, Ammania auriculata, Ammania coccinea, Anthemis cotula, Apera spica-venti, Bacopa rotundifolia, Bidens pilosa, Bidens subalternans, Brassica tournefortii, Bromus tectorum, Camelina microcarpa, Chenopodium album, Chrysanthemum coronarium, Conyza bonariensis, Conyza canadensis, Cuscuta campestris, Cyperus difformis, Damasonium minus, Descurainia sophia, Diplotaxis tenuifolia, Echium plantagineum, Elatine triandra var, pedicellata, Euphorbia heterophylla, Fallopia convolvulus, Fimbristylis miliacea, Galeopsis tetrahit, Galium spurium, Helianthus annuus, Iva xanthifolia, Ixophorus unisetus, Kochia scoparia, Lactuca serriola, Limnocharis flava, Limnophila erecta, Limnophila sessiliflora, Lindernia dubia, Lindernia dubia var, major, Lindernia micrantha, Lindernia procumbens, Mesembryanthemum crystallinum, Monochoria korsakowii, Monochoria vaginalis, Neslia paniculata, Papaver rhoeas, Parthenium hysterophorus, Pentzia suffruticosa, Phalaris minor, Raphanus raphanistrum, Raphanus sativus, Rapistrum rugosum, Rotala indica var, uliginosa, Sagittaria guyanensis, Sagittaria montevidensis, Sagittaria pygmaea, Salsola iberica, Scirpus juncoides var, ohwianus, Scirpus mucronatus, Setaria lutescens, Sida spinosa, Sinapis arvensis, Sisymbrium orientale, Sisymbrium thellungii, Solanum ptycanthum, Sonchus asper, Sonchus oleraceus, Sorghum bicolor, Stellaria media, Thlaspi arvense, Xanthium strumarium, Arctotheca calendula, Conyza sumatrensis, Crassocephalum crepidiodes, Cuphea carthagenenis, Epilobium adenocaulon, Erigeron philadelphicus, Landoltia punctata, Lepidium virginicum, Monochoria korsakowii, Poa annua, Solanum americanum, Solanum nigrum, Vulpia bromoides, Youngia japonica, Hydrilla verticillata, Plantago lanceolata, Carduus nutans, Carduus pycnocephalus, Centaurea solstitialis, Cirsium arvense, Commelina diffusa, Convolvulus arvensis, Daucus carota, Digitaria ischaemum, Echinochloa crus-pavonis, Fimbristylis miliacea, Galeopsis tetrahit, Galium spurium, Limnophila erecta, Matricaria perforate, Papaver rhoeas, Ranunculus acris, Soliva sessilis, Sphenoclea zeylanica, Stellaria media, Nassella trichotoma, Stipa neesiana, Agrostis stolonifera, Polygonum aviculare, Alopecurus japonicus, Beckmannia syzigachne, Bromus tectorum, Chloris inflate, Echinochloa erecta, Portulaca oleracea,* and *Senecio vulgaris.*

33. The cropping system of claim 1, further comprising the step of identifying a tough weed in the crop growing region and applying a herbicide treatment effective to control the tough weed, wherein tough weed is selected from the group consisting of *Abutilon theophrasti, Amaranthus* sp., *Amaranthus palmeri, Ambrosia artemisiifolia, Ambrosia trifida, Chenopodium album, Convolvulus arvensis, Conyza canadensis, Commelina* sp., *Commelina benghalensis, Ipomoea* sp., *Kochia* sp., *Polygonum convolvulus, Lolium rigidum, Sida spinosa,* and *Solanum ptycanthum.*

34. The cropping system of claim 33, wherein the crop seed is a seed of a soybean or cotton plant.

35. The cropping system of claim 1, further comprising:
  a) identifying within the crop growing region a herbicide-resistant weed tolerant to at least the first herbicide treatment; and
  b) applying an amount of an auxin-like herbicide, glufosinate, and/or glyphosate effective to control the herbicide resistant weed.

36. A method for minimizing the development of an herbicide resistant weed comprising: rotating a first cropping system in a first growing season with a second cropping system in a subsequent growing season, wherein the first or second cropping system comprises the steps of:
- a) planting in a crop growing environment a crop seed that germinates into a crop plant comprising tolerance to benzoic acid herbicide; and
- b) applying at least a first herbicide treatment to the crop growing environment to control weed growth, wherein the herbicide treatment is selected from the group consisting of the first, second, third, fourth and fifth treatment set forth in Table 3, wherein the treatment comprises an amount of herbicide effective to control weed growth without significantly damaging the crop seed or crop plant, and wherein at least one herbicide treatment is applied which comprises an herbicidally effective amount of a benzoic acid herbicide selected from the group consisting of the first, second, third, and fourth treatment set forth in Table 3.

37. The method of claim 36, wherein the crop plant in the first cropping system possesses at least one different herbicide tolerance relative to the crop plant in the second cropping system.

38. The method of claim 36, wherein the crop plant in the first cropping system and the crop plant in the second cropping system comprise herbicide tolerances as set forth in Table 7.

39. The method of claim 36, wherein the crop plant in the first and second cropping systems are tolerant to at least one herbicide selected from the group consisting of glyphosate, glufosinate, dicamba, 2,4-D and a combination thereof.

40. The method of claim 36, wherein the crop plant in selected from the group consisting of corn, cotton and soybean.

41. The method of claim 40, wherein the crop plant in the first cropping system and crop plant in the second cropping system are the same species.

42. The method of claim 40, wherein the crop plant in the first cropping system and crop plant in the second cropping system are different species.

* * * * *

UNITED STATES PATENT AND TRADEMARK OFFICE
CERTIFICATE OF CORRECTION

PATENT NO. : 7,939,721 B2  
APPLICATION NO. : 11/758660  
DATED : May 10, 2011  
INVENTOR(S) : Arnevik et al.

Page 1 of 1

It is certified that error appears in the above-identified patent and that said Letters Patent is hereby corrected as shown below:

Title page, item [75] for Inventors, delete "Creve Coecer" and insert --Creve Coeur--.

In claim 32, column 84, line 11, delete "*var,*" and insert --*var.*--.

In claim 32, column 84, line 17, delete "*var,* major" and insert --*var. major*--.

In claim 32, column 84, line 22, delete "*var, uliginosa*" and insert --*var. uliginosa*--.

In claim 32, column 84, line 24, delete "*var,*" and insert --*var. ohwianus*--.

In claim 33, column 84, line 50, delete "sp." and insert --*sp.*--.

In claim 33, column 84, line 11, delete "*var,*" and insert --*var.*--.

In claim 33, column 84, line 53, delete "*Commelina* sp." and insert --*Commelina sp.*--.

In claim 33, column 84, line 53, delete "*Ipomoea* sp." and insert --*Ipomoea sp.*--.

In claim 33, column 84, line 54, delete "*Kochia* sp." and insert --*Kochia sp.*--.

In claim 40, column 86, line 9, delete "plant in" and insert --plant is--.

Signed and Sealed this  
Twenty-sixth Day of July, 2011

David J. Kappos  
*Director of the United States Patent and Trademark Office*

UNITED STATES PATENT AND TRADEMARK OFFICE
CERTIFICATE OF CORRECTION

Page 1 of 1

PATENT NO. : 7,939,721 B2
APPLICATION NO. : 11/758660
DATED : May 10, 2011
INVENTOR(S) : Cindy L. Arvenik et al.

It is certified that error appears in the above-identified patent and that said Letters Patent is hereby corrected as shown below:

In column 65, line 54, delete "MON19788" and insert --MON89788--.

Signed and Sealed this
Twenty-first Day of February, 2012

David J. Kappos
*Director of the United States Patent and Trademark Office*

SEQUENCE LISTING

```
<160> NUMBER OF SEQ ID NOS: 15

<210> SEQ ID NO 1
<211> LENGTH: 441
<212> TYPE: DNA
<213> ORGANISM: Artificial
<220> FEATURE:
<223> OTHER INFORMATION: Synthetic construct
<220> FEATURE:
<221> NAME/KEY: CDS
<222> LOCATION: (1)..(441)

<400> SEQUENCE: 1 atg ata gag gtg aaa ccg att aac gca gag gat acc tat gaa cta agg      48
```

```
Met Ile Glu Val Lys Pro Ile Asn Ala Glu Asp Thr Tyr Glu Leu Arg
1               5                   10                  15 cat aga ata ctc aga cca aac cag ccg ata gaa gcg tgt atg ttt gaa      96
His Arg Ile Leu Arg Pro Asn Gln Pro Ile Glu Ala Cys Met Phe Glu
                20                  25                  30 agc gat tta ctt cgt ggt gca ttt cac tta ggc ggc ttt tac agg ggc     144
Ser Asp Leu Leu Arg Gly Ala Phe His Leu Gly Gly Phe Tyr Arg Gly
            35                  40                  45 aaa ctg att tcc ata gct tca ttc cac cag gcc gag cac tcg gaa ctc     192
Lys Leu Ile Ser Ile Ala Ser Phe His Gln Ala Glu His Ser Glu Leu
        50                  55                  60 caa ggc cag aaa cag tac cag ctc cga ggt atg gct acc ttg gaa ggt     240
Gln Gly Gln Lys Gln Tyr Gln Leu Arg Gly Met Ala Thr Leu Glu Gly
65                  70                  75                  80 tat cgt gag cag aaa gcg gga tca act cta gtt aaa cac gct gaa gaa     288
Tyr Arg Glu Gln Lys Ala Gly Ser Thr Leu Val Lys His Ala Glu Glu
                85                  90                  95 atc ctt cgt aag agg ggg gcg gac atg ctt tgg tgt aat gcg agg aca     336
Ile Leu Arg Lys Arg Gly Ala Asp Met Leu Trp Cys Asn Ala Arg Thr
                100                 105                 110 tcc gcc tca ggc tac tac aaa aag tta ggc ttc agc gag cag gga gag     384
Ser Ala Ser Gly Tyr Tyr Lys Lys Leu Gly Phe Ser Glu Gln Gly Glu
            115                 120                 125 ata ttt gac acg ccg cca gta gga cct cac atc ctg atg tat aaa agg     432
Ile Phe Asp Thr Pro Pro Val Gly Pro His Ile Leu Met Tyr Lys Arg
        130                 135                 140 atc aca taa                                                         441
Ile Thr
145
```

<210> SEQ ID NO 2
<211> LENGTH: 146
<212> TYPE: PRT
<213> ORGANISM: Artificial
<220> FEATURE:
<223> OTHER INFORMATION: Synthetic Construct

<400> SEQUENCE: 2

```
Met Ile Glu Val Lys Pro Ile Asn Ala Glu Asp Thr Tyr Glu Leu Arg
1               5                   10                  15

His Arg Ile Leu Arg Pro Asn Gln Pro Ile Glu Ala Cys Met Phe Glu
                20                  25                  30

Ser Asp Leu Leu Arg Gly Ala Phe His Leu Gly Gly Phe Tyr Arg Gly
            35                  40                  45

Lys Leu Ile Ser Ile Ala Ser Phe His Gln Ala Glu His Ser Glu Leu
        50                  55                  60

Gln Gly Gln Lys Gln Tyr Gln Leu Arg Gly Met Ala Thr Leu Glu Gly
65                  70                  75                  80

Tyr Arg Glu Gln Lys Ala Gly Ser Thr Leu Val Lys His Ala Glu Glu
                85                  90                  95

Ile Leu Arg Lys Arg Gly Ala Asp Met Leu Trp Cys Asn Ala Arg Thr
                100                 105                 110

Ser Ala Ser Gly Tyr Tyr Lys Lys Leu Gly Phe Ser Glu Gln Gly Glu
            115                 120                 125

Ile Phe Asp Thr Pro Pro Val Gly Pro His Ile Leu Met Tyr Lys Arg
        130                 135                 140

Ile Thr
145
```

```
<210> SEQ ID NO 3
<211> LENGTH: 57
<212> TYPE: PRT
<213> ORGANISM: Pisum sativum

<400> SEQUENCE: 3

Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Cys
    50                  55

<210> SEQ ID NO 4
<211> LENGTH: 85
<212> TYPE: PRT
<213> ORGANISM: Arabidopsis thaliana

<400> SEQUENCE: 4

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Glu Lys
    50                  55                  60

Lys Lys Phe Glu Thr Leu Ser Tyr Leu Pro Asp Leu Thr Asp Ser Gly
65                  70                  75                  80

Gly Arg Val Asn Cys
            85

<210> SEQ ID NO 5
<211> LENGTH: 76
<212> TYPE: PRT
<213> ORGANISM: Arabidopsis thaliana

<400> SEQUENCE: 5

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75

<210> SEQ ID NO 6
<211> LENGTH: 76
<212> TYPE: PRT
<213> ORGANISM: Arabidopsis thaliana

<400> SEQUENCE: 6

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
```

```
            20                  25                  30
Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75

<210> SEQ ID NO 7
<211> LENGTH: 72
<212> TYPE: PRT
<213> ORGANISM: Petunia hybrida

<400> SEQUENCE: 7

Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Ser Phe Leu
            20                  25                  30

Val Phe Gly Ser Lys Lys Leu Lys Asn Ser Ala Asn Ser Met Leu Val
        35                  40                  45

Leu Lys Lys Asp Ser Ile Phe Met Gln Lys Phe Cys Ser Phe Arg Ile
    50                  55                  60

Ser Ala Ser Val Ala Thr Ala Cys
65                  70

<210> SEQ ID NO 8
<211> LENGTH: 69
<212> TYPE: PRT
<213> ORGANISM: Triticum aestivum

<400> SEQUENCE: 8

Met Ala Ala Leu Val Thr Ser Gln Leu Ala Thr Ser Gly Thr Val Leu
1               5                   10                  15

Ser Val Thr Asp Arg Phe Arg Arg Pro Gly Phe Gln Gly Leu Arg Pro
            20                  25                  30

Arg Asn Pro Ala Asp Ala Ala Leu Gly Met Arg Thr Val Gly Ala Ser
        35                  40                  45

Ala Ala Pro Lys Gln Ser Arg Lys Pro His Arg Phe Asp Arg Arg Cys
    50                  55                  60

Leu Ser Met Val Val
65

<210> SEQ ID NO 9
<211> LENGTH: 171
<212> TYPE: DNA
<213> ORGANISM: Pisum sativum

<400> SEQUENCE: 9
atggcttcta tgatatcctc ttccgctgtg acaacagtca gccgtgcctc tagggggcaa      60
tccgccgcaa tggctccatt cggcggcctc aaatccatga ctggattccc agtgaggaag     120
gtcaacactg acattacttc cattacaagc aatggtggaa gagtaaagtg c              171

<210> SEQ ID NO 10
<211> LENGTH: 255
<212> TYPE: DNA
<213> ORGANISM: Arabidopsis thaliana

<400> SEQUENCE: 10
atggcttcct ctatgctctc ttccgctact atggttgcct ctccggctca ggccactatg      60
```

-continued

```
gtcgctcctt tcaacggact taagtcctcc gctgccttcc cagccacccg caaggctaac    120
aacgacatta cttccatcac aagcaacggc ggaagagtta actgtatgca ggtgtggcct    180
ccgattgaaa agaagaagtt tgagactctc tcttaccttc ctgaccttac cgattccggt    240
ggtcgcgtca actgc                                                    255
```

<210> SEQ ID NO 11
<211> LENGTH: 228
<212> TYPE: DNA
<213> ORGANISM: Arabidopsis thaliana

<400> SEQUENCE: 11

```
atggcgcaag ttagcagaat ctgcaatggt gtgcagaacc catctcttat ctccaatctc     60
tcgaaatcca gtcaacgcaa atctcccttca tcggtttctc tgaagacgca gcagcatcca    120
cgagcttatc cgatttcgtc gtcgtgggga ttgaagaaga gtgggatgac gttaattggc    180
tctgagcttc gtcctcttaa ggtcatgtct tctgtttcca cggcgtgc                 228
```

<210> SEQ ID NO 12
<211> LENGTH: 228
<212> TYPE: DNA
<213> ORGANISM: Artificial sequence
<220> FEATURE:
<223> OTHER INFORMATION: Synthetic primer

<400> SEQUENCE: 12

```
atggcgcaag ttagcagaat ctgcaatggt gtgcagaacc catctcttat ctccaatctc     60
tcgaaatcca gtcaacgcaa atctcccttca tcggtttctc tgaagacgca gcagcatcca    120
cgagcttatc cgatttcgtc gtcgtgggga ttgaagaaga gtgggatgac gttaattggc    180
tctgagcttc gtcctcttaa ggtcatgtct tctgtttcca cggcgtgc                 228
```

<210> SEQ ID NO 13
<211> LENGTH: 216
<212> TYPE: DNA
<213> ORGANISM: Artificial sequence
<220> FEATURE:
<223> OTHER INFORMATION: Synthetic primer

<400> SEQUENCE: 13

```
atggcccaga tcaacaacat ggcccagggc atccagaccc tgaaccctaa ctctaacttc     60
cacaagccgc aagtgcccaa gtctagctcc ttcctcgtgt tcggctccaa gaagctcaag    120
aatagcgcca attccatgct ggtcctgaag aaagactcga tcttcatgca gaagttctgc    180
tcctttcgca tcagtgcttc ggttgcgact gcctgc                             216
```

<210> SEQ ID NO 14
<211> LENGTH: 207
<212> TYPE: DNA
<213> ORGANISM: Artificial sequence
<220> FEATURE:
<223> OTHER INFORMATION: Synthetic primer

<400> SEQUENCE: 14

```
atggcggcac tggtgacctc ccagctcgcg acaagcggca ccgtcctgtc ggtgacggac     60
cgcttccggc gtcccggctt ccaggactg aggccacgga acccagccga tgccgctctc    120
gggatgagga cggtgggcgc gtccgcggct cccaagcaga gcaggaagcc acaccgtttc    180
gaccgccggt gcttgagcat ggtcgtc                                       207
```

```
<210> SEQ ID NO 15
<211> LENGTH: 433
<212> TYPE: DNA
<213> ORGANISM: Artificial
<220> FEATURE:
<223> OTHER INFORMATION: Synthetic primer

<400> SEQUENCE: 15
agatcttgag ccaatcaaag aggagtgatg tagacctaaa gcaataatgg agccatgacg      60
taagggctta cgcccatacg aaataattaa aggctgatgt gacctgtcgg tctctcagaa     120
cctttacttt ttatgtttgg cgtgtatttt taaatttcca cggcaatgac gatgtgaccc    180
aacgagatct tgagccaatc aaagaggagt gatgtagacc taaagcaata atggagccat    240
gacgtaaggg cttacgccca tacgaaataa ttaaaggctg atgtgacctg tcggtctctc    300 agaacccttta cttttatat ttggcgtgta tttttaaatt tccacggcaa tgacgatgtg    360
acctgtgcat ccgctttgcc tataaataag ttttagtttg tattgatcga cacggtcgag    420
aagacacggc cat                                                      433
```